United States Patent
Lindsey et al.

(10) Patent No.: US 6,603,070 B2
(45) Date of Patent: *Aug. 5, 2003

(54) CONVERGENT SYNTHESIS OF MULTIPORPHYRIN LIGHT-HARVESTING RODS

(75) Inventors: Jonathan S. Lindsey, Raleigh, NC (US); Robert S. Loewe, Morrisville, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/939,010

(22) Filed: Aug. 24, 2001

(65) Prior Publication Data

US 2003/0111108 A1 Jun. 19, 2003

Related U.S. Application Data

(63) Continuation-in-part of application No. 09/852,560, filed on May 10, 2001, which is a continuation-in-part of application No. 09/670,463, filed on Sep. 26, 2000, which is a continuation-in-part of application No. 09/621,797, filed on Jul. 21, 2000, now Pat. No. 6,420,648.

(51) Int. Cl.[7] ............... H01L 31/0248; H01L 31/04; C07D 487/22

(52) U.S. Cl. ............ 136/263; 136/252; 136/256; 257/40; 257/431; 540/145; 429/111

(58) Field of Search ............... 136/263, 252, 136/256; 257/40, 431; 429/111; 540/145

(56) References Cited

U.S. PATENT DOCUMENTS

| | | | | |
|---|---|---|---|---|
| 5,371,199 A | * | 12/1994 | Therien et al. | 534/11 |
| 6,208,553 B1 | * | 3/2001 | Gryko et al. | 365/151 |
| 6,212,093 B1 | * | 4/2001 | Lindsey | 365/151 |
| 6,235,895 B1 | * | 5/2001 | McEwan et al. | 540/145 |
| 6,272,038 B1 | * | 8/2001 | Clausen et al. | 365/151 |
| 6,407,330 B1 | * | 6/2002 | Lindsey et al. | 136/263 |
| 6,420,648 B1 | * | 7/2002 | Lindsey | 136/263 |
| 2002/0033192 A1 | * | 3/2002 | Lindsey et al. | 136/263 |
| 2002/0137925 A1 | * | 9/2002 | Lindsey et al. | 540/145 |

OTHER PUBLICATIONS

Balasubramanian et al, "Rational Synthesis of J–Substituted Building Blocks," J. Org. Chem. (2000), vol. 65, pp. 7919–7929.*

Balasubramanian, Thiagarajan, et al., *Rational Synthesis of β–Substituted Chlorin Building Blocksl, J. Org. Chem.*, vol. 65, pp. 7919–7929 (2000).

Burrell, Anthony K., et al.; *Synthetic Routes to Multiporphyrin Arrays, Chem. Rev.*, vol. 101, pp. 2751–2796 (2001).

Henze, Oliver, et al., *Synthesis and an X–ray Structure of Soluble Phenylacetylene Macrocycles with Two Opposing Bipyridine Donor Sites, Chem. Eur. J.*, vol. 6, No. 13, pp. 2362–2367 (2000).

Höger, Sigurd, et al., *Synthesis and Properties of Shape–Persistent Macrocyclic Amphiphiles with Switchable Amphiphilic Portions, Chem. Eur. J.*, vol. 4, No. 12, pp. 2423–2434 (1998).

(List continued on next page.)

Primary Examiner—Alan Diamond
(74) Attorney, Agent, or Firm—Myers Bigel Sibley & Sajovec

(57) ABSTRACT

The present invention provides a convergent method for the synthesis of light harvesting rods. The rods are oligomers of the formula $A^1(A^{b+1})_b$, wherein b is at least 1, $A^1$ through $A^{b+1}$ are covalently coupled rod segments, and each rod segment $A^1$ through $A^{1+b}$ comprises a compound of the formula $X^1(X^{m+1})_m$ wherein m is at least 1 and $X^1$ through $X^{m+1}$ are covalently coupled porphyrinic macrocycles. Light harvesting arrays and solar cells containing such light harvesting rods are also described, along with intermediates useful in such methods and rods produced by such methods.

60 Claims, 3 Drawing Sheets-

OTHER PUBLICATIONS

Kotora, Matin, et al., *Highly Efficient and Selective Procedures for the Synthesis of y–Alkylidenebutenolides via Palladium–Catalyzed Ene–Yne Coupling and Palladium– or Silver–Catalyzed Lactonization of (Z)–2–En–4–ynoic Acids. Synthesis of Rubrolides A, C, D, and E, Synthesis*, pp. 121–128 (1997).

Sharman, W. M., et al., *Use of palladium catalysis in the synthesis of novel porphyrins and phthalocyanines, Journal of Porphyrins and Phthalocyanines*, vol. 4, pp. 441–453 (2000).

Tobe, Yoshito, et al., *Synthesis and Association Behavior of [4.4.4.4.4.4] Metacyclophanedodecayne Derivatives with Interior Binding Groups, Angew. Chem. Int. Ed.*, vol. 37, No. 9, pp. 1285–1287 (1998).

U.S. patent Publication No. US 2002/0033192 A1 published Mar. 21, 2002.

U.S. patent Publication No. US 2002/0137925 A1 published Sep. 26, 2002.

Wong, Man Shing, et al., *Synthesis and Computational Studies of Hyperpolarizable Zig–Zag Chromophores, Tetrahedron Letters*, vol. 35, No. 33, pp. 6113–6116 (1994).

* cited by examiner

CONVERGENT SYNTHESIS OF MULTIPORPHYRIN LIGHT-HARVESTING RODS

RELATED APPLICATIONS

This application is a continuation-in-part of commonly owned, U.S. patent application Ser. No. 09/852,560, filed May 10, 2001, allowed which is a continuation-in-part of Ser. No. 09/670,463, filed Sep. 26, 2000, which is a continuation-in-part of Ser. No. 09/621,797, filed Jul. 21, 2000, now U.S. Pat. No. 6,420,648 the disclosures of all of which are incorporated by reference herein in their entirety.

GOVERNMENT SUPPORT

This invention was made with Government support under Grant No. DE-FG02-96ER14632 from the Department of Energy. The Government has certain rights to this invention.

FIELD OF THE INVENTION

The present invention concerns solar cells, particularly regenerative solar cells, light harvesting arrays useful in such solar cells, light harvesting rods for use therein, methods of making light-harvesting rods, and intermediates useful for the manufacture of light-harvesting rods.

BACKGROUND OF THE INVENTION

Molecular approaches for converting sunlight to electrical energy have a rich history with measurable "photoeffects" reported as early as 1887 in Vienna (Moser, J. *Montash. Chem.* 1887, 8, 373.). The most promising designs were explored in considerable detail in the 1970's (Gerischer, H. *Photochem. Photobiol.* 1972, 16, 243; Gerischer, H. *Pure Appl. Chem.* 1980, 52, 2649; Gerischer, H.; Willig, F. *Top. Curr. Chem.* 1976, 61, 31). Two common approaches incorporate molecules that selectively absorb sunlight, termed photosensitizers or simply sensitizers, covalently bound to conductive electrodes. Light absorption by the sensitizer creates an excited state, that injects an electron into the electrode and then oxidizes a species in solution. Such a photoelectrosynthetic cell produces both electrical power and chemical products. Many of the molecular approaches over the past few decades were designed to operate in the manner shown with the goal of splitting water into hydrogen and oxygen. In contrast, a regenerative cell converts light into electricity with no net chemistry. In the regenerative solar cell, the oxidation reactions that take place at the photoanode are reversed at the dark cathode.

The principal difficulty with these solar cell designs is that a monolayer of a molecular sensitizer on a flat surface does not absorb a significant fraction of incident visible light. As a consequence, even if the quantum yields of electron transfer are high on an absorbed photon basis, the solar conversion efficiency will be impractically low because so little light is absorbed. Early researchers recognized this problem and tried to circumvent it by utilizing thick films of sensitizers. This strategy of employing thick absorbing layers was unsuccessful as intermolecular excited-state quenching in the thick sensitizer film decreased the yield of electron injection into the electrode.

A number of additional approaches have been taken. One class of thick film sensitizers is provided by the so-called organic solar cells (Tang, C. W. and Albrecht, A. C. *J. Chem. Phys.* 1975, 63, 953–961). The state-of-the-art organic solar cells are multilayer organic "heterojunction" films or doped organic layers that yield ~2% efficiencies under low irradiance, but the efficiency drops markedly as the irradiance approaches that of one sun (Forrest, S. R. et al., *J. Appl. Phys.* 1989, 183, 307; Schon, J. H. et al., *Nature* 2000, 403, 408). Another class of molecular-based solar cells are the so-called photogalvanic cells that were the hallmark molecular level solar energy conversion devices of the 1940's–1950's (Albery, W. J. *Acc. Chem. Res.* 1982, 15, 142). However, efficiencies realized to date are typically less than 2%.

In 1991, a breakthrough was reported by Gratzel and O'Regan (O'Regan, B. et al., *J. Phys. Chem.* 1990, 94, 8720; O'Regan, B. and Grätzel, M. *Nature* 1991, 353, 737). By replacing the planar electrodes with a thick porous colloidal semiconductor film, the surface area for sensitizer binding increased by over 1000-fold. Gratzel and O'Regan demonstrated that a monolayer of sensitizer coating the semiconductor particles resulted in absorption of essentially all of the incident light, and incident photon-to-electron energy conversion efficiencies were unity at individual wavelengths of light in regenerative solar cells. Furthermore, a global efficiency of ~5% was realized under air-mass 1.5 illumination conditions; this efficiency has risen to a confirmed 10.69% today (Gratzel, M. in "Future Generation Photovoltaic Technologies" McConnell, R. D.; AIP Conference Proceedings 404, 1997, page 119). These "Gratzel" solar cells have already found niche markets and are commercially available in Europe.

These high surface area colloidal semiconductor films (Gratzel cells) achieve a high level of absorption but also have the following significant drawbacks. (1) A liquid junction is required for high efficiency (because the highly irregular surface structure makes deposition of a solid-state conductive layer essentially impossible). (2) The colloidal semiconductor films require high temperature annealing steps to reduce internal resistances. Such high temperatures impose severe limitations on the types of conductive substrates that can be used. For example, polymeric substrates that melt below the required annealing temperatures cannot be used. (3) Significant losses are associated with transporting charge through the thick semiconductor films. These losses do not appreciably decrease the photocurrent, but have a large effect on the voltage output and thus the power is decreased significantly (Hagfeldt, A.; Grätzel, M. *Chem. Rev.* 1995, 95, 49). Accordingly, there remains a need for new molecular approaches to the construction of solar cells.

SUMMARY OF THE INVENTION

A first aspect of the present invention is a light harvesting array, comprising:

(a) a first substrate comprising a first electrode; and
(b) a layer of light harvesting rods electrically coupled to the first electrode, the light harvesting rods comprising, consisting essentially of or consisting of an oligomer of Formula I:

$$A^1(A^{b+1})_b \quad (I)$$

wherein:
(i) b is at least 1;
(ii) $A^1$ through $A^{b+1}$ are covalently coupled rod segments, which segments are different and which segments have sequentially less positive electrochemical potentials; and
(iii) each segment $A^1$ through $A^{1+b}$ comprises a compound of Formula II:

$$X^1(X^{m+1})_m \quad (II)$$

and wherein:

m is at least 1; and $X^1$ through $X^{m+1}$ are covalently coupled porphyrinic macrocycles.

For example, $X^1$ through $X^{m+1}$ may be selected from the group consisting of chlorins, bacteriochlorins, and isobacteriochlorins; b may be from 1 to 2, 5 or 10; m may be from 1 or 2 to 5, 10, or 20; in some embodiments, at least one, or all, of $X^1$ through $X^{m+1}$ may be meso-linked porphyrinic macrocycles; in other embodiments, at least one, or all, of $X^1$ through $X^{m+1}$ may be β-linked porphyrinic macrocycle (and particularly trans β-linked porphyrinic macrocycles). In one embodiment, each porphyrinic macrocycle $X^1$ through $X^{m+1}$ is the same within each individual rod segment.

In general, the light harvesting rods are preferably linear, are preferably oriented substantially perpendicularly to the first electrode, and are preferably not greater than 500 nanometers in length. The light harvesting rods are preferably intrinsic rectifiers of excited-state energy, and are preferably intrinsic rectifiers of ground-state holes.

The substrate in the light harvesting array may be rigid or flexible, transparent or opaque, and may be substantially planar in shape. The electrode may comprise a metallic or nonmetallic conductor. Substrates and electrodes in solar cells as described below may be of the same materials as substrates and electrodes in the light harvesting arrays described herein.

A further aspect of the present invention is a solar cell comprising a light harvesting array as described above, and a second substrate comprising a second electrode, with the first and second substrate being positioned to form a space therebetween, and with at least one of (i) the first substrate and the first electrode and (ii) the second substrate and the second electrode being transparent. There is optionally but preferably an electrolyte in the space between the first and second substrates. The electrolyte may be aqueous or nonaqueous, polymeric or nonpolymeric, liquid or solid, etc. In one embodiment, the solar cell is devoid of (i.e., free of) liquid in the space between the first and second substrates. In some embodiments, the light harvesting rods may be electrically coupled to the second electrode. In some embodiments, a mobile charge carrier may be included in the electrolyte.

A further aspect of the present invention is a composition of light harvesting rods, the light harvesting rods comprising, consisting essentially of or consisting of an oligomer of Formula I as described above.

A still further aspect of the present invention is a method of making a composition of light harvesting rods, the light harvesting rods comprising, consisting essentially of or consisting of an oligomer of Formula I as given above. The method comprises the steps of:

(a) providing a first rod segment of Formula III and a second rod segment of Formula IV:

$$E[X^1(X^{m+1})_m]^1f \quad \text{(III)}$$

$$G[X^1(X^{m+1})_m]^2T \quad \text{(IV)}$$

wherein:

$X^1$, $X^{m+1}$, and m are as given above;

E is an end group;

one of f or G is an ethynyl group, and the other of f or G is a halo group (preferably not iodo); and T is an end group; and then (b) coupling, preferably by Sonogoshira coupling, the segment of Formula III to the segment of Formula IV to produce a compound of Formula I. In a particular embodiment, f is an ethynyl group; and G is a halo group. In a more particular embodiment, E is a bromo group; f is an ethynylphenyl group; G is an iodo group; and T is a protected ethynyl group.

In a further embodiment, E is a halo group (preferably different from whichever of f or G is a halo group) and the providing step (a) further comprises providing a compound of Formula V:

$$Z[X^1(X^{m+1})_m]^3J \quad \text{(V)}$$

wherein $X^1$, $X^{m+1}$, and m are as given above, Z is an end group and J is an ethynyl group; the method further comprising the step of: (c) coupling (preferably by Sonogashira coupling) the segment of Formula V to the product of the prior coupling step (b) to produce a compound of Formula I.

A still further aspect of the present invention is a rod segment useful for the production of light harvesting rods, the rod segment comprising a compound of Formula III:

$$E[X^1(X^{m+1})_m]^1f \quad \text{(III)}$$

wherein:

E is selected from the group consisting of bromo, chloro, and fluoro (preferably bromo);

f is an ethynyl group, preferably an ethynylphenyl group, which may be protected or unprotected;

m is as given above;

$X^1$ through $X^{m+1}$ are covalently coupled porphyrinic macrocycles; and each porphyrinic macrocycle $X^1$ through $X^{m+1}$ is the same.

A variety of different electrical devices comprised of a solar cell as described above having circuits (typically resistive loads) electrically coupled thereto can be produced with the solar cells of the invention.

The present invention is explained in greater detail in the drawings herein and the specification set forth below.

DETAILED DESCRIPTION OF THE PREFERRED EMBODIMENTS

Figure 1:
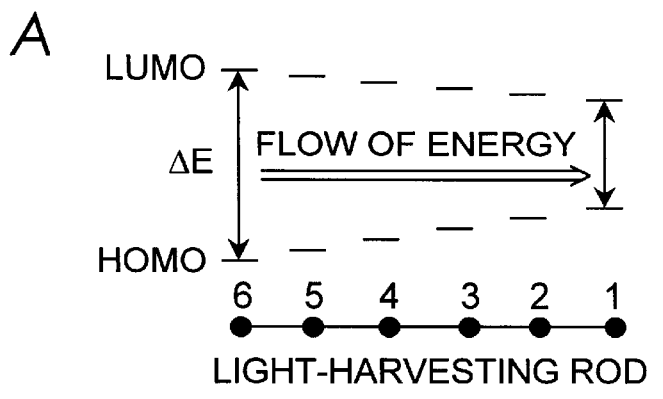
FIG. 1. Molecular physics considerations for designing light-harvesting rods. (A) The energy of the excited-state (ΔE) is given by the difference between the energies of the highest occupied molecular orbital (HOMO) and the lowest unoccupied molecular orbital (LUMO). Energy migration occurs from a pigment with large ΔE to a pigment with smaller ΔE. (B) The energy level of the ground-state hole is given by the electrochemical potential ($E_{1/2}$) for the one-electron oxidation, which depends only on the energy of the HOMO. Hole-hopping occurs from a pigment with high potential to a pigment with low potential. (C) A light-harvesting rod composed of pigments with appropriate energy levels supports the flow of excited-state energy and ground-state holes in opposite directions (i.e., intrinsic rectification).
Figure 1:
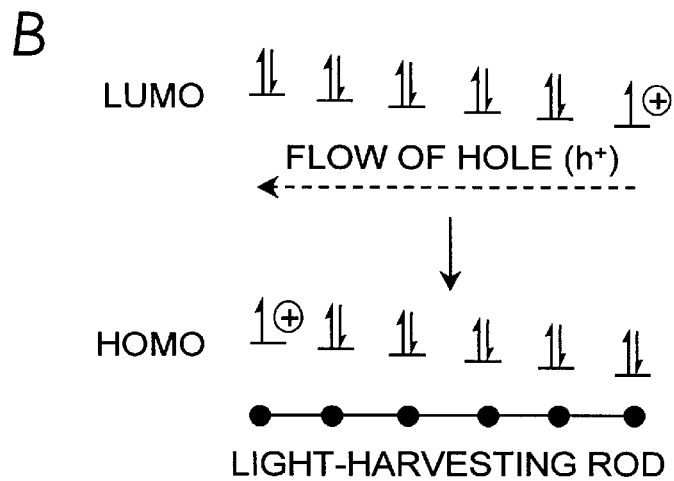
Figure 1:
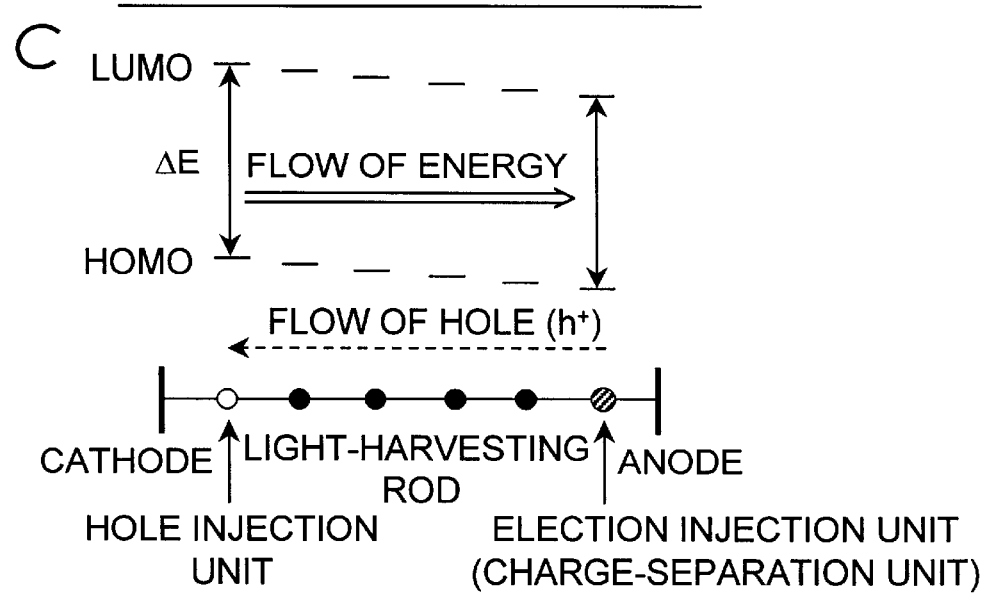

The following terms and phrases are used herein:

A substrate as used herein is preferably a solid material (which may be flexible or rigid) suitable for the attachment of one or more molecules. Substrates can be formed of materials including, but not limited to glass, organic polymers, plastic, silicon, minerals (e.g. quartz), semiconducting materials, ceramics, metals, etc. The substrate may be in any suitable shape, including flat, planar, curved, rod-shaped, etc. The substrate may be inherently conductive and serve itself as an electrode, or an electrode may be formed on or connected to the substrate by any suitable means (e.g., deposition of a gold layer or a conductive oxide layer). Either or both of the substrates in the solar cells may be transparent (that is, wavelengths of light that excite the chromophores can pass through the substrate and corresponding electrode, even if they are visually opaque). In light-harvesting arrays, the substrate and electrode may be of any suitable type. One of the substrates may be opaque with respect to the wavelengths of light that excite the chromophores. One of the substrates may be reflective or provided with a reflective coating so that light that passes through the arrays or rods is reflected back to the arrays or rods.

The term "electrode" refers to any medium capable of transporting charge (e.g. electrons) to and/or from a light harvesting rod. Preferred electrodes are metals (e.g., gold, aluminum), non-metals (e.g., conductive oxides, carbides, sulfide, selinides, tellurides, phosphides, and arsenides such as cadmium sulfide, cadmium telluride, tungsten diselinide, gallium arsenide, gallium phosphide, etc.), and conductive organic molecules. The electrodes can be manufactured to virtually any 2-dimensional or 3-dimensional shape.

The term "conductive oxide" as used herein refers to any suitable conductive oxide including binary metal oxides such as tin oxide, indium oxide, titanium oxide, copper oxide, and zinc oxide, or ternary metal oxides such as strontium titanate and barium titanate. Other examples of suitable conductive oxides include but are not limited to indium tin oxide, titanium dioxide, gallium indium oxide, and zinc indium oxide. The metal oxide semiconductors may be intrinsic or doped, with trace amounts of materials, to control conductivity.

The term "heterocyclic ligand" as used herein generally refers to any heterocyclic molecule consisting of carbon atoms containing at least one, and preferably a plurality of, heteroatoms (e.g., N, O, S, Se, Te), which heteroatoms may be the same or different, and which molecule is capable of forming a sandwich coordination compound with another heterocyclic ligand (which may be the same or different) and a metal. Such heterocyclic ligands are typically macrocycles, particularly tetrapyrrole derivatives such as the phthalocyanines, porphyrins, and porphyrazines.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring.

The term porphyrin refers to a cyclic structure typically composed of four pyrrole rings together with four nitrogen atoms and two replaceable hydrogens for which various metal atoms can readily be substituted. A typical porphyrin is hemin.

A "chlorin" is essentially the same as a porphyrin, but differs from a porphyrin in having one partially saturated pyrrole ring. The basic chromophore of chlorophyll, the green pigment of plant photosynthesis, is a chlorin.

A "bacteriochlorin" is essentially the same as a porphyrin, but differs from a porphyrin in having two partially saturated non-adjacent (i.e., trans) pyrrole rings.

An "isobacteriochlorin" is essentially the same as a porphyrin, but differs from a porphyrin in having two partially saturated adjacent (i.e., cis) pyrrole rings.

The terms "sandwich coordination compound" or "sandwich coordination complex" refer to a compound of the formula $L^n M^{n-1}$, where each L is a heterocyclic ligand such as a porphyrinic macrocycle, each M is a metal, n is 2 or more, most preferably 2 or 3, and each metal is positioned between a pair of ligands and bonded to one or more hetero atom (and typically a plurality of heteroatoms, e.g., 2, 3, 4, 5) in each ligand (depending upon the oxidation state of the metal). Thus sandwich coordination compounds are not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another). See, e.g., D. Ng and J. Jiang, Chem. Soc. Rev. 26, 433–442 (1997). Sandwich coordination compounds may be "homoleptic" (wherein all of the ligands L are the same) or "heteroleptic" (wherein at least one ligand L is different from the other ligands therein).

The term "double-decker sandwich coordination compound" refers to a sandwich coordination compound as described above where n is 2, thus having the formula $L^1—M^1—L^2$, wherein each of $L^1$ and $L^2$ may be the same or different. See, e.g., J. Jiang et al., J. Porphyrins Phthalocyanines 3, 322–328 (1999).

The term "multiporphyrin array" refers to a discrete number of two or more covalently linked porphyrinic macrocycles. The multiporphyrin arrays can be linear, cyclic, or branched, but are preferably linear herein. Light harvesting rods herein are preferably multiporphyrin arrays. The light harvesting rods or multiporphyrin arrays may be linear (that is, all porphyrinic macrocycles may be linked in trans) or may contain one or more bends or "kinks" (for example, by including one or more non-linear linkers in a light-harvesting rod, or by including one or more cis-substituted porphyrinic macrocycles in the light harvesting rod) Some of the porphyrinic macrocycles may further include additional ligands, particularly porphyrinic macrocycles, to form sandwich coordination compounds as described further below. The rods optionally but preferably are oriented substantially perpendicularly to either, and most preferably both, of the first and second electrodes.

"Chromophore" means a light-absorbing unit which can be a unit within a molecule or can comprise the entire molecule. Typically a chromophore is a conjugated system (alternating double and single bonds which can include non-bonded electrons but is not restricted to alternating double and single bonds since triple and single bonds, since mixtures of alternating triple/double and single bonds also constitute chromophores. A double or triple bond alone constitutes a chromophore. Heteroatoms can be included in a chromophore.). Examples of chromophores include the cyclic 18 pi-electron conjugated system that imparts color to porphyrinic pigments, the linear system of alternating double and single bonds in the visual pigment retinal, or the carbonyl group in acetone.

"Charge separation group" and "charge separation unit" refer to molecular entities that upon excitation (by direct absorption or energy transfer from another absorber) displace an electron to another part of the same molecule, or transfer an electron to a different molecule, semiconductor, or metal. The "charge separation group" and "charge separation unit" results in storage of some fraction of the excited-state energy upon displacement or transfer of an electron. Typically the "charge separation group" and "charge separation unit" is located at the terminus of a light-harvesting array or rod, from which excited-state energy is received. The "charge separation group" and "charge separation unit" facilitates or causes conversion of the excited-state energy into a separate electron and hole or an electron-hole pair. The electron can be injected into the semiconductor by the "charge separation group" or "charge separation unit". It is feasible that the "charge separation group" and "charge separation unit" could extract an electron from a different molecule or semiconductor, thereby creating a negative charge on the "charge separation group" and "charge separation unit" and a hole in the other molecule or semiconductor. The reaction center of bacterial photosynthesis is a premier example of a "charge separation group" or "charge separation unit". Synthetic porphyrin-quinone or porphyrin-buckyball molecules also function to absorb light and utilize the resulting energy to separate charge.

The term "substituent" as used in the formulas herein, particularly designated by S or $S^n$ where n is an integer, in a preferred embodiment refer to electron-rich or electron-deficient groups (subunits) that can be used to adjust the redox potential(s) of the subject compound. Preferred substituents include, but are not limited to, H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In certain embodiments, a substituted aryl group is attached to a porphyrin or a porphyrinic macrocycle, and the substituents on the aryl group are selected from the group consisting of aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. Additional substituents include, but are not limited to, 4-chlorophenyl, 4-trifluoromethylphenyl, and 4-methoxyphenyl. Preferred substituents provide a redox potential range of less than about 5 volts, preferably less than about 2 volts, more preferably less than about 1 volt.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl group, while acting as substituent can itself have additional substituents (e.g. the substituents provided for $S^n$ in the various formulas herein).

The term "alkyl" refers to a paraffinic hydrocarbon group, typically C1 to C4, which may be derived from an alkane by dropping one hydrogen from the formula. Examples are methyl ($CH_3$—), ethyl ($C_2H_5$—), propyl ($CH_3CH_2CH_2$—), isopropyl (($CH_3$)$_2$CH—).

The term "alkenyl" refers to a hydrocarbon group, typically C2 to C4, derived from the corresponding alkyl and which contains at least one double bond (e.g., butadienyl).

The term "alkynyl" refers to a hydrocarbon group, typically C2 to C4, derived from the corresponding alkyl and which contains at least one triple bond (e.g., butadiynyl).

The term "halogen" refers to one of the electronegative elements of group VIIA of the periodic table (fluorine, chlorine, bromine, iodine, astatine).

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CR unit is replaced with a nitrogen atom.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the —OH of the carboxyl group is replaced by some other substituent (RCO—). Examples are, but are not limited to acetyl, benzoyl, etc.

In preferred embodiments, when a metal is designated by "M" or "$M^n$", where n is an integer, it is recognized that the metal may be associated with a counterion.

A linker is a molecule used to couple two different molecules, two subunits of a molecule, or a molecule to a substrate. When all are covalently linked, they form units of a single molecule.

The term "electrically coupled" when used with reference to a light harvesting rod and electrode, or to chromophores, charge separation groups and electrodes, refers to an association between that group or molecule and the coupled group or electrode such that electrons move from the molecule to the electrode or from the electrode to the molecule and thereby alter the oxidation state of the storage molecule. Electrical coupling can include direct covalent linkage between the molecule and the electrode, indirect covalent coupling (e.g. via a linker), direct or indirect ionic bonding between the molecule and the electrode, or other bonding (e.g. hydrophobic bonding). In addition, no actual bonding may be required and the light harvesting rod may simply be contacted with the electrode surface. There also need not necessarily be any contact between the electrode and the light harvesting rod where the electrode is sufficiently close to the light harvesting rod to permit electron tunneling between the molecule and the electrode.

"Excited-state energy" refers to the energy stored in the chromophore in a metastable state following absorption of light (or transfer of energy from an absorber). For an excited singlet (triplet) state, the magnitude of the "excited-state energy" is estimated by energy of the shortest wavelength fluorescence (phosphorescence) band. The magnitude of the "excited-state energy" is greater than or equal to the energy of the separated electron and hole following charge separation.

Electrolytes used to carry out the present invention may be aqueous or non-aqueous electrolytes, including polymer electrolytes. The electrolyte may comprise or consist of a solid, in which latter case the solar cell can be produced devoid of liquid in the space between the first and second substrates. The electrolyte consists of or comprises a substance that increases the electrical conductivity of a carrier medium. Most electrolytes are salts or ionic compounds. Examples include sodium chloride (table salt), lithium iodide, or potassium bromide in water; tetrabutylammonium hexafluorophosphate or tetraethylammonium perchlorate in acetonitrile or dichloromethane; or an ionic polymer in a gel.

"Mobile charge carriers" refers to an ion, molecule, or other species capable of translating charges (electrons or holes) between the two electrodes in a solar cell. Examples include quinones in water, molten salts, and iodide in a polymer gel such as polyacrylonitrile. Examples of mobile charge carriers include, but are not limited to, iodide, bromide, tetramethyl-1,4-phenylenediamine, tetraphenyl-1,4-phenylenediamine, p-benzoquinone, $C_{60}$, $C_{70}$, pentacene, tetrathiafulvalene, and methyl viologen.

A. Monomers.

The primary requirements for pigment monomers which may serve as individual monomers in constructing the rod segments and light harvesting rods of the invention, are intense absorption in the visible region, a narrow distribution of energies of the excited state (marked by sharp absorption and fluorescence bands), an excited singlet-state lifetime sufficient: for energy transfer (typically a few nanoseconds), and compatibility with the synthetic building block approach giving rise to a linear architecture. The pigments of choice for use in the linear light harvesting rods are drawn from the porphyrinic family (tetrapyrrole macrocycles). Examples include porphyrins, chlorins, bacteriochlorins, tetraazaporphyrins (porphyrazines), phthalocyanines, naphthalocyanines, and derivatives of these compounds. The porphyrinic pigments can be supplemented with accessory pigments such as members of the perylene, lycopene, xanthene, and dipyrromethene families. The absorption spectra of such pigments are well known to those skilled in the art and can be looked up in various reference sources (Du, H. et al., *Photochem. Photobiol.* 1998, 68:141–142).

The important requirements for the linkers joining the pigments are as follows. (1) Support rapid excited-state energy-transfer processes (through-bond and/or through-space), (2) support ground-state hole-hopping processes in some cases, and (3) afford compatibility with the synthetic building block approach giving rise to a linear arrangement of pigments. The linkers of choice for joining the pigments in the linear light harvesting rods include 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, 4,4"-terphenyl, and no linker (i.e., a direct C—C bond). The p,p'-diphenylethyne and p-phenylene linkers have been shown to support rapid excited-state energy transfer and ground-state hole-hopping processes among porphyrinic molecules.

One important requirement for the charge-separation unit (CSU) is to have an excited-state of energy equal to or lower than that of the adjacent pigments in the light harvesting array (in other words, absorb light at wavelengths equal to or longer than that of the pigments in the light harvesting array). For semiconductor based solar cells the excited-state reduction potential must be greater than the conduction band edge. Additional requirements for the CSU are to undergo rapid excited-state electron transfer, have sufficient energy to inject an electron into the conduction band of the electrode, and afford a stable radical cation. Molecules of choice for the CSU also are drawn from the porphyrinic family, including porphyrins, chlorins, bacteriochlorins, tetraazaporphyrins (porphyrazines), phthalocyanines, naphthalocyanines, and derivatives of these compounds. A particularly attractive group of derivatives is comprised of the double-decker sandwich molecules with a central metal such as zirconium (Kim, K. et al., *Inorg. Chem.* 1991, 30, 2652–2656; Girolami, G. S. et al., *Inorg. Chem.* 1994, 33, 626–627; Girolami, G. S. et al., *Angew. Chem. Int. Ed. Engl.* 1996, 35, 1223–1225; Collman, J. P. et al., *Inorg. Chem.* 1997, 36, 5603–5608).

In the porphyrinic family the electrochemical potential of a given porphyrin can be tuned over quite a wide range by incorporation of electron-withdrawing or electron-releasing substituents (Yang, S. I. et al., *J. Porphyrins Phthalocyanines* 1999, 3, 117–147). Examples of such substituents include aryl, phenyl, cycloalkyl, alkyl, halogen, alkoxy, alkylthio, perfluoroalkyl, perfluoroaryl, pyridyl, cyano, thiocyanato, nitro, amino, N-alkylamino, acyl, sulfoxyl, sulfonyl, imido, amido, and carbamoyl. With monomeric porphyrins variation in electrochemical potential can also be achieved with different central metals (Fuhrhop, J.-H.; Mauzerall, D. *J. Am. Chem. Soc.* 1969, 91, 4174–4181). A wide variety of metals can be incorporated in porphyrins. Those metals that are photochemically active include Zn, Mg, Al, Sn, Cd, Au, Pd, and Pt. It is understood that some metals carry a counterion. Porphyrins generally form very stable radical cations (Felton, R. H. In *The Porphyrins*; Dolphin, D., Ed.; Academic Press: New York, 1978; Vol. V, pp 53–126).

The linkers joining the CSU to the electrode surface provide a linear architecture, support through-space and/or through-bond electron transfer, and have a functional group suitable for attachment to the electrode. Examples of suitable functional groups include ester, carboxylic acid, boronic acid, thiol, phenol, silane, hydroxy, sulfonic acid, phosphonic acid, alkylthiol, etc. The linkers can consist of 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, 4,4"-terphenyl, 1,3-phenyl, 3,4'-diphenylethyne, 3,4'-diphenylbutadiyne, 3,4'-biphenyl, 3,4'-stilbene, 3,4'-azobenzene, 3,4'-benzylideneaniline, 3,4"-terphenyl, etc.

Particular examples of porphyrinic macrocycles that may be used as ligands to carry out the present invention include compounds of Formula X, Formula XI, Formula XII, Formula XIII, Formula XIV, Formula XV, Formula XVI, and Formula XVII below (with formulas XII through XVII representing various chlorins, including bacteriochlorins and isobacteriochlorins).

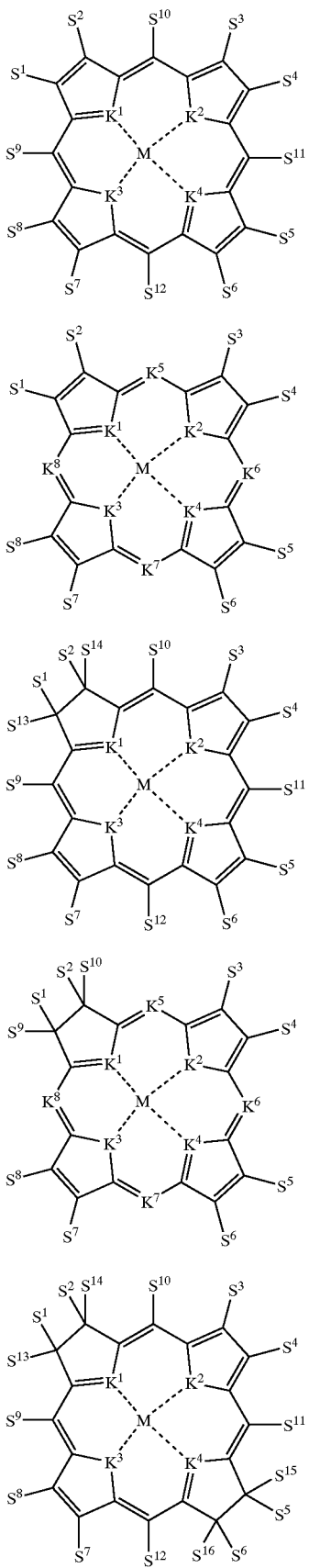

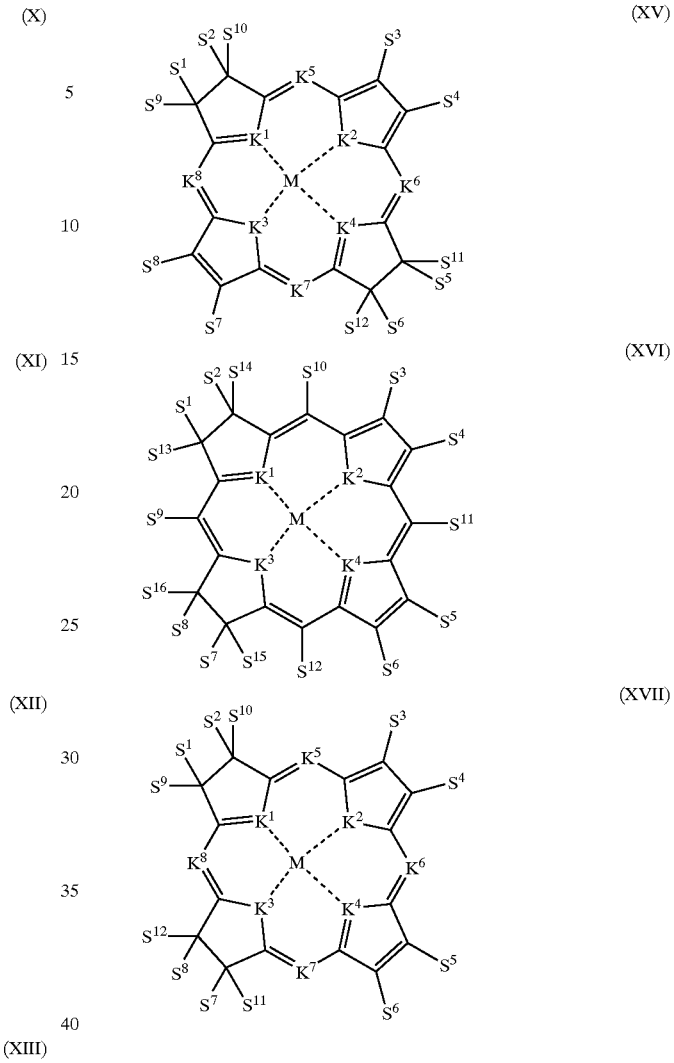

wherein:

M is a metal, such as a metal selected from the group consisting of Zn, Mg, Pt, Pd, Sn and Al, or M is absent (in which case the ring heteroatoms $K^1$ through $K^4$ are substituted with H,H as required to satisfy neutral valency);

$K^1$, $K^2$, $K^3$, $K^4$, $K^5$, $K^6$, $K^7$, and $K^8$ are heteroatoms, such as heteroatoms independently selected from the group consisting of N, O, S, Se, Te, and CH;

$S^1$, $S^2$, $S^3$, $S^4$, $S^5$, $S^6$, $S^7$, $S^8$, $S^9$, $S^{10}$, $S^{11}$, $S^{12}$, $S^{13}$, $S^{14}$, $S^{15}$ and $S^{16}$ are independently selected substituents that preferably provide a redox potential of less than about 5, 2 or even 1 volt. Example substituents $S^1$, $S^2$, $S^3$, $S^4$ include, but are not limited to, H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

In addition, $S^1$ through $S^{16}$ may comprise a linking group (—Q—) covalently linked to an adjacent porphyrinic macrocycle of $X^1$ through $X^{m+1}$ or a linking group covalently linked to said first electrode (—QY). In one embodiment of the invention, the linking groups of each porphyrinic macrocycle are oriented in trans; in another embodiment of the invention, one or more porphyrinic macrocycles contains linking groups that are oriented in cis to one another so that the the light harvesting rods contain bends or kinks, or the linker itself is non-linear or oblique.

In a particular embodiment of the foregoing, a trans-substituted chlorin that may be used to carry out the present invention comprises compounds of Formula XVIII:

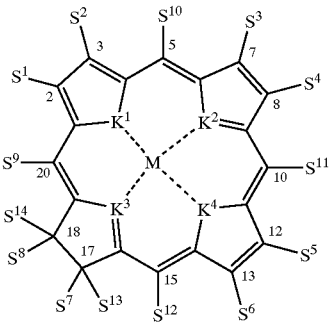

wherein:
- M is a metal, such as a metal selected from the group consisting of Zn, Mg, Pt, Pd, Sn and Al, or M is absent (in which case the ring heteroatoms $K^1$ through $K^4$ are substituted with H,H as required to satisfy neutral valency);
- $K^1$, $K^2$, $K^3$, and $K^4$, are heteroatoms, such as heteroatoms independently selected from the group consisting of N, O, S, Se, Te, and CH. Preferably, K is N.
- $S^1$, $S^2$, $S^3$, $S^4$, $S^5$, $S^6$, $S^7$, $S^8$, $S^9$, $S^{10}$, $S^{11}$, $S^{12}$, $S^{13}$, and $S^{14}$ are independently selected substituents (that may optionally provide a redox potential of less than about 5, 2 or even 1 volt). Example substituents include, but are not limited to, H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
- optionally but preferably, one, two three or four of S through $S^{14}$ are linking groups Q; and more preferably either $S^1$ and $S^5$ are the trans-substituted linking groups $Q^1$ and $Q^2$, or $S^2$ and $S^6$ are trans-substituted linking groups $Q^1$ and $Q^2$; and
- $S^7$ and $S^{13}$ together may optionally form =O (an oxochlorin).

Preferably, when $S^7$ and $S^{13}$ are an oxo group =O, then neither $S^8$ nor $S^{14}$ are H. Preferably, when $S^7$ and $S^{13}$ are not an oxo group, then not more than two of $S^7$, $S^8$, $S^{13}$, and $S^{14}$ are H, and then only when both H groups are bound to the same carbon.

Note numbering in Formula XVIII departs from the current IUPAC scheme to make clear the correct tautomer.

The trans-substituted linking groups $Q^1$ and $Q^2$ are independently selected linking groups of the formula:

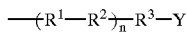

wherein:
- n is from 0 or 1 to 5 or 10;
- $R^3$ may be present or absent (in one embodiment when n is 0 then $R^3$ is present; in another embodiment, when n is 0 $R^3$ may also be absent);
- $R^1$, $R^2$, and $R^3$ are each independently selected from the group consisting of ethene, ethyne, aryl, and heteroaryl groups (e.g., phenyl, and derivatives of pyridine, thiophene, pyrrole, phenyl, etc.), which aryl and heteroaryl groups may be unsubstituted or substituted one or more times with H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

Y may be a protected or unprotected reactive site or group on the linker such as a hydroxy, thio, seleno, telluro, carboxy, ester, carboxylic acid, boronic acid, phenol, silane, sulfonic acid, phosphonic acid, alkylthiol, formyl, halo (e.g., iodo, bromo, chloro), alkenyl, alkynyl, haloalkyl, haloalkyl, alkyl phosphonate, alkyl sulfonate, alkyl carboxylate, and alkyl boronate groups.

Trans-substituted chlorins may be prepared in accordance with known procedures, or by the procedures described in copending application Ser. No. 09/852,560, filed May 10, 2001, the disclosure of which is incorporated herein by reference in its entirety.

Particular examples of sandwich coordination compounds that may be used to carry out the present invention (e.g., as charge separation groups) include those described in U.S. Pat. No. 6,212,093, the disclosure of which is incorporated by reference herein in its entirety.

To link the porphyrinic macrocycle (which may or may not be a component of a sandwich coordination comound) to a substrate, or to another compound such as another porphyrinic macrocycle in the manners described above, at least one ligand in the porphyrinic macrocycle will have to contain at least one and preferably two substituents $S^1$ through $S^n$ or S' which is a linker, particularly a linker containing a reactive group (where multiple linkers are substituted on the ligand, the linkers may be the same or independently selected). Such linkers are designated as Y—Q— herein, where: Q is a linker, and Y is a substrate, a reactive site or group that can covalently couple to a substrate, or a reactive site or group that can ionically couple to a substrate.

Q may be a linear linker or an oblique linker, with linear linkers currently preferred. Examples of oblique linkers include, but are not limited to, 4,3'-diphenylethyne, 4,3'-diphenylbutadiyne, 4,3'-biphenyl, 1,3-phenylene, 4,3'-stilbene, 4,3'-azobenzene, 4,3'-benzylideneaniline, and 4,3"-terphenyl. Examples of linear linkers include, but are not limited to, 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, 4,4"-terphenyl, 3-mercaptophenyl, 3-mercaptomethylphenyl, 3-(2-mercaptoethyl)phenyl, 3-(3-mercaptopropyl)phenyl, 3-(2-(4-mercaptophenyl)ethynyl) phenyl, 3-carboxyphenyl, 3-carboxymethylphenyl, etc.

Thus, examples of linear linkers for Y—Q— are: 4-[2-mercaptoethyl)phenyl, 4-[3-mercaptopropyl)phenyl, an ω-alkylthiol of form $HS(CH_2)_n$— where n=1–20, 4-carboxyphenyl, 4-carboxymethylphenyl, 4-(2-carboxyethyl)phenyl, an ω-alkylcarboxylic acid of form $HO_2C(CH_2)_n$— where n=1–20, 4-(2-(4-carboxyphenyl) ethynyl)phenyl, 4-(2-(4-carboxymethylphenyl)ethynyl) phenyl, 4-(2-(4-(2-carboxyethyl)phenyl)ethynyl)phenyl, 4-(2-(4-mercaptophenyl)ethynyl)phenyl, 4-mercaptomethylphenyl, 4-hydroselenophenyl, 3-(2-(4-hydroselenophenyl)ethynyl)phenyl, 4-hydrotellurophenyl, and 4-(2-(4-hydrotellurophenyl)ethynyl)phenyl.

Examples of oblique linkers for Y—Q— are: 3-(2-(4-mercaptophenyl)ethynyl)phenyl, 3-mercaptomethylphenyl, 3-hydroselenophenyl, 3-(2-(4-hydroselenopenyl)ethynyl) phenyl, 3-hydrotellurophenyl, and 3-(2-(4-hydrotellurophenyl)ethynyl)phenyl; etc.

Other suitable linkers include, but are not limited to, 2-(4-mercaptophenyl)ethynyl, 2-(4-hydroselenophenyl) ethynyl, and 2-(4-hydrotellurophenyl)ethynyl.

Thus, linkers between adjacent porphyrinic macrocycles within a light harvesting rod, or between a porphyrinic macrocycle and an electrode, are typically those that permit superexchange between the linked chromophores (mediated electronic communication between chromophores which permits or allows excited-state energy transfer and/or exchange of electrons and/or holes). Examples of suitable linkers may be generally represented by the formula —Q—, where Q may be a direct covalent bond or a linking group of the Formula:

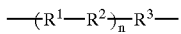

wherein:
- n is from 0 or 1 to 5 or 10;
- $R^3$ may be present or absent (yielding a direct covalent bond when $R^3$ is absent and n is 0); and
- $R^1$, $R^2$, and $R^3$ are each independently selected from the group consisting of ethene, ethyne, aryl, and heteroaryl groups (e.g., phenyl, and derivatives of pyridine, thiophene, pyrrole, phenyl, etc., which aryl and heteroaryl groups may be unsubstituted or substituted one or more times with the same substituents listed above with respect to porphyrinic macrocycles).

The geometry of the linkers with respect to the various chromophores and charge separation groups in the light harvesting rods can vary. In one embodiment, at least one of $X^2$ through $X^{m+1}$ comprises a meso-linked porphyrinic macrocycle. In another embodiment, at least one of $X^2$ through $X^{m+1}$ comprises a trans meso-linked porphyrinic macrocycle. In another embodiment, $X^2$ through $X^{m+1}$ consist of meso-linked porphyrinic macrocycles. In another embodiment, $X^2$ through $X^{m+1}$ consist of trans meso-linked porphyrinic macrocycles. In another embodiment, at least one of $X^2$ through $X^{m+1}$ comprises a β-linked porphyrinic macrocycle. In another embodiment, at least one of $X^2$ through $X^{m+1}$ comprises a trans β-linked porphyrinic macrocycle. In still another embodiment, $X^2$ through $X^{m+1}$ consist of β-linked porphyrinic macrocycles. In still another embodiment, $X^2$ through $X^{m+1}$ consist of trans β-linked porphyrinic macrocycles.

"End groups" that may be used in the present invention include, for example, halo groups as described herein, ethynyl groups as described herein (protected or unprotected as appropriate for the particular reaction or use), and any group including linking groups as described in conjunction with $S^1$ through $S^{16}$ herein.

D. Oligomer Synthesis.

The synthesis of rods comprised of multiple porphyrinic units presents a number of challenges. For the preparation of diphenylethyne-linked rods, an iodophenyl porphyrin and an ethynylphenyl porphyrin can be joined via the Sonogashira reaction. Through use of a porphyrin building block bearing one iodo group and one protected ethyne (e.g., a trimethylsilylethynyl unit), iterative coupling procedures enable the stepwise synthesis of multiporphyrin rods. An example is shown in Scheme 1. An end-capped mono-ethynyl porphyrin (E—$X^1$—CCH, where E denotes the cap, $X^1$ denotes the porphyrin, and CCH denotes the ethyne) is reacted with an iodo/trimethylsilylethynyl porphyrin (I—$X^2$—CCTMS, where I denotes the iodo group, $X^2$ denotes the porphyrin, and CCTMS denotes the trimethylsilylethyne) to give the diphenylethyne-linked dyad bearing the end cap and the protected ethyne (E—$X^1$—$X^2$—CCTMS). The trimethylsilylethyne can be deprotected by exposure to base (e.g., $K_2CO_3$ or NaOH, in methanolic tetrahydrofuran) or fluoride (e.g., tetra-n-butylammonium fluoride), affording the dyad with a free ethyne (E—$X^1$—$X^2$—CCH). Repetition of this sequence of reactions (coupling, deprotection) enables the synthesis of monodisperse rods of porphyrinic macrocycles. This iterative divergent route has been used in a number of applications (Wagner, R. W. and Lindsey, J. S. *J. Am. Chem. Soc.* 1994, 116, 9759–9760; Wagner, R. W. et al. *J. Am. Chem. Soc.* 1996, 118, 11166–11180).

Scheme 1

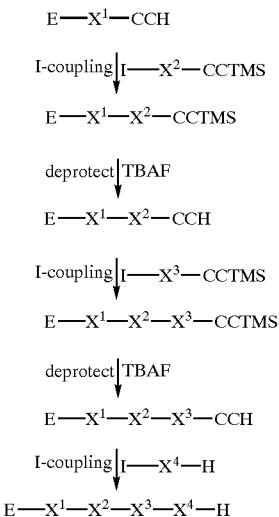

The Sonogashira reaction was initially described for reactions with relatively small, highly soluble compounds (Sonogashira, K. et al. *Tetrahedron Lett.* 1975, 4467–4470; Takahashi, S. et al. *Synthesis* 1980, 627–630). The conditions for the Sonogashira reaction with porphyrins differ substantially from those with smaller organic molecules (Wagner, R. W. et al. *J. Org. Chem.* 1995, 60, 5266–5273; Wagner, R. W. et al. *Chem. Mater.* 1999, 11, 2974–2983). Owing to the typically poor solubility of porphyrins, the reactions are done in dilute solution (e.g., 2.5 mM) instead of 0.1–1 M. Owing to the ability of free base porphyrins to chelate metals and metalloporphyrins to undergo transmetalation, the reactions are best done in the absence of copper cocatalysts. Owing to the value of both iodo and ethyne components, and the usual requirement to purify reaction mixtures by chromatography, the iodo and ethyne porphyrins are typically employed in a ~1:1 ratio instead of using an excess of one species. Thus, a typical coupling reaction proceeds with 2.5 mM [ethyne] and 2.5 mM [iodo], ~0.375 mM $Pd_2(dba)_3$, and ~3.0 mM P(o-tol)$_3$ or $AsPh_3$ in toluene/triethylamine (5:1) at 35° C. under argon. The diphenylethyne-linked product is typically produced in ~60% yield upon reaction for a few hours under these conditions (Wagner, R. W. et al. *Chem. Mater.* 1999, 11, 2974–2983).

As the arrays become larger, chromatographic purification of the rod containing (n+1) porphyrinic units from the rod containing n porphyrinic units becomes more difficult. This feature is a general problem of iterative divergent routes. In contrast, the use of convergent routes typically results in joining smaller components to form a substantially larger component, which is more easily purified. Accordingly, routes employing convergence are sought to replace or augment the iterative divergent routes.

One approach toward multiporphyrin rods that employs convergence is shown in Scheme 2. A porphyrin building block bearing one N,N-diethyltriazene group and one trimethylsilylethyne group is split into two batches. One batch is reacted with methyl iodide, which results in replacement of the N,N-diethyltriazene group with the iodo group, forming the iodo/trimethylsilylethynyl porphyrin (I—$X^1$—CCTMS). The other batch is deprotected with base or fluoride, forming the N,N-diethyltriazene/ethynyl porphyrin ($Et_2N_3$—$X^1$—

CCH). Each porphyrin can be demetalated and/or metalated as desired. The two porphyrins are then subjected to a standard Sonogashira reaction, yielding the ethyne linkage joining the dyad.

Repetition of this cycle of divergent/convergent reactions (not shown) has been used to create a hexameric array of porphyrins (Mongin, O. et al. *Tetrahedron Lett.* 1999, 40, 8347–8350; Rucareanu, S. et al. *J. Org. Chem.* 2001, 66, 4973–4988).

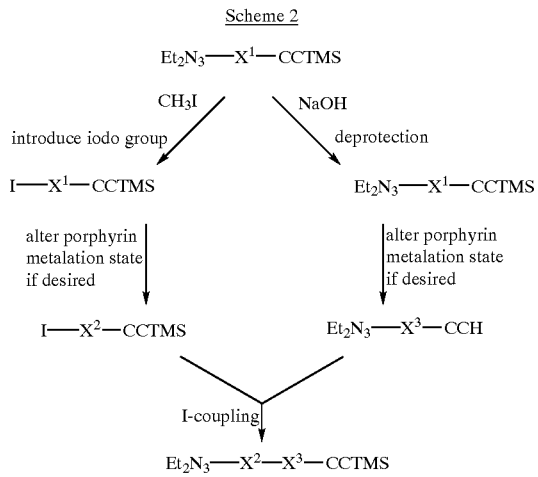

We have developed convergent routes for the preparation of linear multiporphyrin arrays. These routes take advantage of the availability of porphyrin building blocks bearing distinct patterns of substituents. The key finding is that under the standard conditions for the Sonogashira reaction with porphyrins, the coupling of an ethyne group+an iodo group occurs selectively in the presence of a bromo group (with only a small amount detected of bromo+ethyne coupling). Upon performing the iodo+ethyne coupling reaction at room temperature instead of 35° C., no coupling of the bromo group was detected. However, the coupling of an ethyne group+a bromo group occurs with good efficiency upon performing the same reaction at higher temperature, namely at 50–80° C. This difference in reactivity, which can be elicited by altering the reaction temperature, enables coupling of an iodo group+an ethyne group, followed by a bromo group+an ethyne group. The bromo group can be in the same molecule as either the iodo or ethyne group. The bromo+ethynyl coupling can be performed with addition of a second batch of Pd-coupling reagents during the course of the reaction to boost the yield. The selectivity of the successive coupling reactions provides the foundation for performing convergent syntheses of multiporphyrin arrays. Several examples are provided in Schemes 3–10.

In Scheme 3, an end-capped mono-ethynyl porphyrin dyad (E—$X^1$—$X^2$—CCH) is prepared by standard Sonogashira reaction (room temperature) of an iodo/CCTMS porphyrin and an ethynyl porphyrin. The reaction (room temperature) of an end-capped mono-iodo porphyrin (I—$X^4$—H) with a bromo/ethynyl porphyrin (Br—$X^3$—CCH) affords the dyad product of iodo+ethyne coupling (Br—$X^3$—$X^4$—H). Subsequent coupling (50–80° C.) of the latter with the mono-ethynyl porphyrin dyad affords the tetrad E—$X^1$—$X^2$—$X^3$—$X^4$—H. This route was employed in the Examples to prepare a diphenylethyne-linked porphyrin tetrad. This approach is more efficient than the iterative divergent procedure in Scheme 1, and avoids the use of methyl iodide at elevated temperature (a potent alkylating agent) to introduce an iodo group. Moreover, this route employs an initial set of building blocks and affords control over the nature of each porphyrin in the array (peripheral substituents, metal, etc.) whereas the iterative divergent-convergent procedure starts with one type of porphyrin and introduces variations in the nature of the metalloporphyrin as the synthesis proceeds.

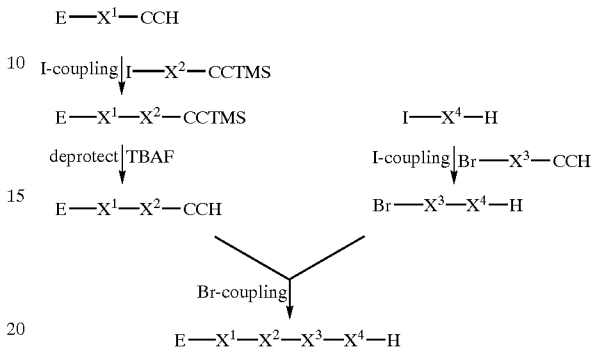

A related route is shown in Scheme 4. This route employs an iodo/bromo porphyrin building block rather than a bromo/ethynyl porphyrin building block as in Scheme 3. Both routes afford convergence in the synthesis of the target tetrad.

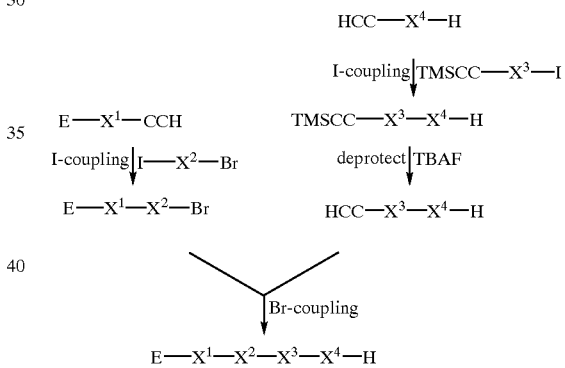

A route for preparing a porphyrin pentamer is shown in Scheme 5. Two selective iodo+ethyne couplings (room temperature) are performed in the presence of a bromo group, affording a bromo/end-capped triad (Br—$X^3$—$X^4$—$X^5$—H). The latter is coupled (50–80° C.) with an ethynyl/end-capped dyad (E—$X^1$—$X^2$—CCH) affording the target pentad. This route was used to prepare a diphenylethyne-linked porphyrin pentad (see Examples).

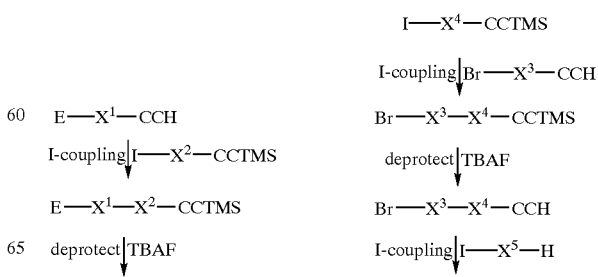

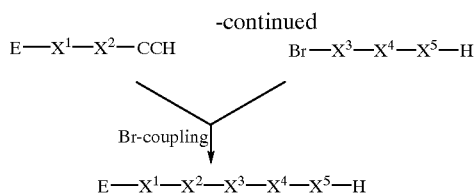

Yet another example of selective, successive coupling is shown in Scheme 6. A diethynyl porphyrin is bis-coupled (room temperature) with two equivalents of a bromo/iodo porphyrin, affording a dibromo triad (Br—$X^1$—$X^2$—$X^1$—Br). A diethynyl triad is prepared by a standard Sonogashira reaction. The two triads are then reacted in the presence of a template under the conditions for bromo+ethyne coupling (50–80° C.), affording a cyclic hexamer of porphyrins. This route was used to prepare a cyclic hexamer (see Examples).

Scheme 6

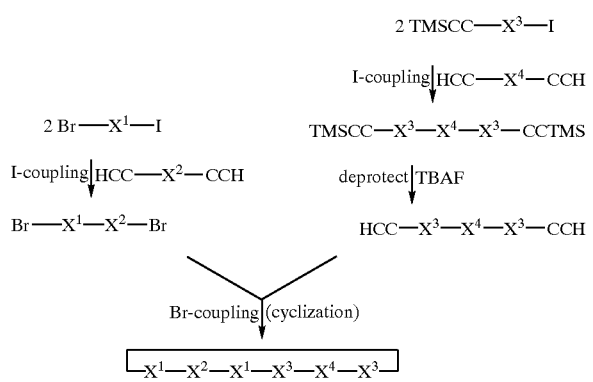

In summary, the use of successive iodo+ethyne and bromo+ethyne coupling reactions enables syntheses of multiporphyrin arrays to be achieved in a convergent manner. A variety of protecting groups can be employed for the ethyne unit (T. W. Greene and P. G. M. Wuts, "Protective Groups in Organic Synthesis," John Wiley & Sons, Inc. New York, 3rd Edition, 1999). Suitable protecting groups for the ethyne include the traditional silyl-based protecting groups such as trimethylsilyl (TMS), triethylsilyl (TES), t-butyldimethylsilyl (TBDMS), or triisopropylsilyl (TIPS); the more recent silyl-based protecting groups such as biphenyldimethylsilyl (BDMS), biphenyldiisopropylsilyl (BDIPS), or dimethyl[1,1-dimethyl-3-(tetrahydro-2 H-pyran-2-yloxy)propylsilyl (DOPS); and the 2-(2-hydroxylpropyl) protecting group. Note that the TMS group can be removed in the presence of the TIPS group or DOPS group by treatment with bases such as $K_2CO_3$ in methanol or KOH in methanol, while both groups can be removed by treatment with fluoride reagents such as tetra-n-butylammonium fluoride or KF. On the other hand, the DOPS group can be removed in the presence of the TMS group or TIPS group by treatment with acid followed by a catalytic amount of a strong base such as n-BuLi. Thus, the TMS (or TIPS) group and the DOPS group constitute a pair of orthogonal protecting groups for the ethyne.

The synthesis shown in Scheme 7 combines the use of selective, successive coupling reactions (iodo+ethyne, then bromo+ethyne) with the orthogonality of the TMS and DOPS to prepare a tetrad component that can be derivatized further. The tetrad bears one TMS group and one DOPS group, which can be removed sequentially. Each ethyne can then be derivatized independently. In one case, end-caps can be introduced. In another case, removal of the DOPS group followed by selective iodo+ethyne coupling (room temperature) with a bromo/iodo porphyrin affords the bromo/trimethylsilylethynyl porphyrin pentad. This bromo/trimethylsilylethynyl pentad can be used in sequential stepwise coupling reactions (bromo+ethyne) to create a monodisperse rod comprised of multiple segments.

Scheme 7

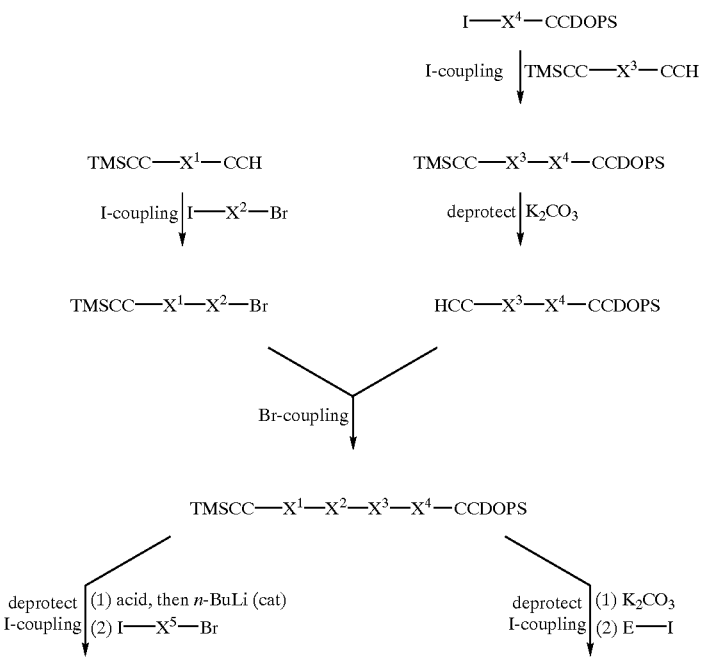

-continued

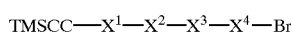

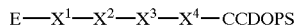

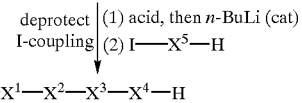

Light-harvesting rods wherein distinct segments have different energies (excited-state energy; one-electron oxidation potential) enables the directed flow of excited-state energy and/or ground-state holes. A design can be realized in which the porphyrinic units in a given segment have essentially identical energies, but the energies systematically change in moving from one segment to another along a rod. Rods designed with such cascade or cataract architectures are invaluable for use in solar cells. The availability of rod components with bromo/trimethylsilylethynyl end groups, in conjunction with the bromo+ethyne coupling conditions (50–80° C.), enables synthesis of such segmented rods. An example is shown in Scheme 8. A given rod segment, such as $Br-X^1-X^2-X^3-X^4-CCTMS$, is abbreviated $Br-A^1-CCTMS$ where $A^1$ refers to the multiple porphyrins in the segment. As shown, two couplings of bromo+ethyne afford a triply segmented rod with end caps, $E-A^1-A^2-A^3-H$. End-caps can be used for attachment to surfaces (cathode, anode) as required for the construction of a solar cell.

Scheme 8

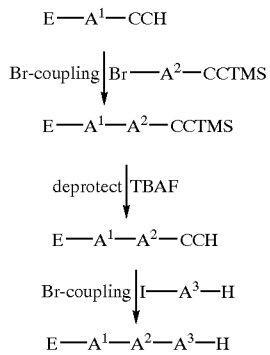

Polymerizations can also be performed to construct segmented rods wherein all porphyrinic units are identical but the linkers between segments are different. The synthesis shown in Scheme 9 employs selective, successive coupling reactions (iodo+ethyne, then bromo+ethyne) to achieve convergence in the synthesis of a diphenylethyne-linked tetrad bearing two identical end groups (TIPS-ethyne). The two TIPS groups can be removed to reveal the diethynyl tetrad. This tetrad can be used as a segment in the construction of longer rods. For example, the diethynyl tetrad ($HCC-X^1-X^2-X^3-X^4-CCH$, now defined as $HCC-A-CCH$) can be subjected to Glaser polymerization under mild conditions (CuI, $I_2$, $Pd(PPh_3)_2Cl_2$, N,N-diisopropylamine, room temperature), which creates butadiyne linkages from two terminal ethynes (Liu, Q. and Burton, D. J. *Tetrahedron Lett.* 1997, 38, 4371–4374). In so doing, a block polymer is constructed comprised of segments of the A rods. With iodophenyl, ethynylphenyl, and bromophenyl groups attached to the initial porphyrin building blocks, the resulting block polymer consists of diphenylethyne linkers between porphyrins within an A segment (tetrads, in this case) and diphenylbutadiyne linkers joining one A segment to another ($HCC-(A)_n-CCH$). The same Glaser polymerization can be carried out with the incorporation of suitable amounts of end-capping agents, namely mono-ethynyl end-caps. Incorporation of the appropriate amount of the end-capping agent yields the desired average length of the polydisperse rods.

Scheme 9

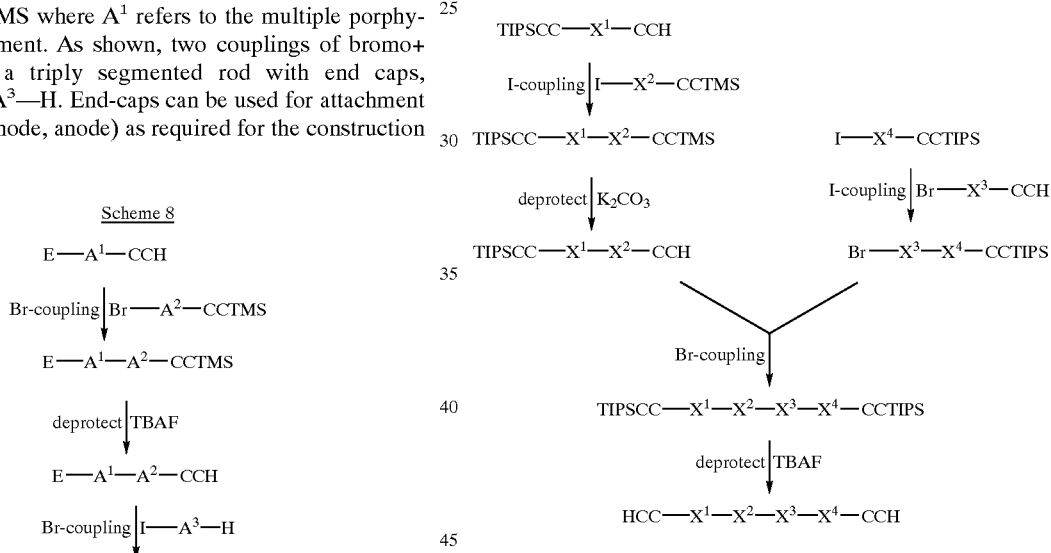

A rod bearing one bromo group and one ethyne group (e.g., $Br-A^1-CCH$) can be subjected to Sonogashira polymerization under the conditions of the bromo+ethyne reaction. In this manner, a block polymer can be constructed that bears ends identical to that in the starting dyad: one bromo group and one ethyne ($Br-(A^1)_n-CCH$). In this case, all porphyrins bear identical linkers. Agents for capping the two ends can be introduced in the polymerization as needed, or after the polymerization is over, affording the polydisperse rods with distinct end-caps. Alternatively, stepwise Sonogashira reactions can be performed on a surface for the in situ construction of monodisperse segmented rods of the following form: surface $-A^1-A^2-A^3-H$ (Scheme 10). One segment is attached to a surface with the trimethylsilylethyne unit distal from the surface. Deprotection unveils the free ethyne, which is then coupled (bromo+ethyne conditions) with a bromo/trimethylsilylethynyl rod segment. Multiple rod segments can be assembled in this manner. One advantage of such surface assembly processes is that unreacted materials can be washed away in each step of each cycle, thereby facilitating purification.

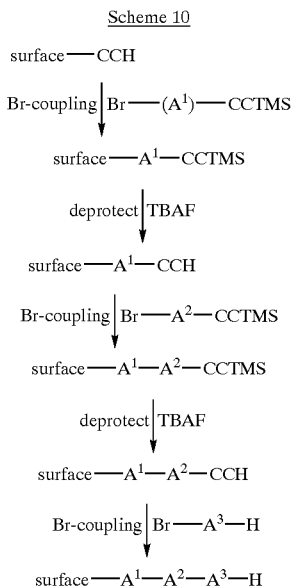

Scheme 10

Light harvesting rods of the present invention are useful for the production of light harvesting arrays and solar cells as described above. Solar cells of the present invention can be used in a variety of different electrical devices. Such devices typically comprise a solar cell as described above, and a circuit (e.g., a resistive load) electrically coupled to said solar cell (e.g., by providing a first electrical coupling of the circuit to one electrode of the solar cell, and a second electrical coupling of the circuit to the other electrode of the solar cell). The solar cell may provide the sole source of power to the circuit, may be a supplemental source, may be incorporated to charge a battery, etc. Any of a variety of different electrical devices may incorporate a solar cell of the invention, including but not limited to radios, televisions, computers (such as personal computers), processors, calculators, telephones, wireless communication devices such as pagers, watches, emergency location devices, electric vehicles, emergency power supplies, power generators, lights or lamps, and other illuminating devices, monitoring devices, inspection devices, radiation detectors, imaging devices, optical coupling devices.

The present invention is explained in greater detail in the following non-limiting Examples. In overview, an important feature of the molecular design is the ability to cause excited-state energy and ground-state holes to migrate in opposite directions along a given light-harvesting rod. Such intrinsic rectification is possible because the physics of the two processes are fundamentally different, as shown in FIG. 1. Energy transfer is an excited-state process. Excited-state energy transfer among neighboring pigments occurs reversibly with isoenergetic pigments and from donor to acceptor when the excited-state energy (ΔE) of the acceptor is lower than that of the donor. Thus, excited-state energy flows along a rod from pigment i+1 to pigment i with excited-state energies such that $$\Delta E_i \leq \Delta E_{i+1} \tag{1}$$

The migration of holes is a ground-state process and the direction of transfer depends on the value of the electrochemical midpoint potential ($E_{1/2}$) for the one-electron oxidation of the pigments in the rod. Ground-state hole transfer among neighboring pigments occurs reversibly with isoenergetic pigments and from (oxidized) pigment i to (non-oxidized) pigment i+1 when the electrochemical potentials are such that $$E_{1/2(i)} \geq E_{1/2(i+1)} \tag{2}$$

Thus, a light-harvesting rod comprised of a sequence of pigments which satisfies equations 1 and 2 should afford intrinsic rectification in the migration of excited-state energy and ground-state holes. This is illustrated pictorially in FIG. 1. Excited-state energy flows along the rod toward the anode while hole migration occurs along the rod from the anode toward the cathode.

In the following Examples, we describe the design of linear rods comprised of 3–5 porphyrins for intrinsic rectification of the migration of excited-state energy and ground-state holes. We then present the synthesis of porphyrin building blocks for construction of the linear rods. The porphyrins in the arrays are joined via diphenylethyne linkers, which are constructed in Pd-mediated coupling reactions of the porphyrin building blocks. Prior syntheses of linear multiporphyrin arrays have employed a divergent approach with iterative couplings of iodo and ethynyl substituents. To achieve convergence in the synthesis of the arrays, we performed a study of successive couplings of iodo+ethyne and bromo+ethyne groups with suitable porphyrin building blocks. The conditions identified for such successive couplings enabled the synthesis of the light-harvesting rods of 4 or 5 porphyrins to be carried out in a convergent manner.

In the Examples, $^1$H (300 MHz) and $^{13}$C (75 MHz) NMR spectra were recorded in CDCl$_3$ unless noted otherwise. Mass spectra of porphyrins were obtained by high resolution fast atom bombardment (FAB), by laser desorption mass spectrometry (LD-MS), or by LD-MS in the presence of the matrix POPOP (MALDI-MS). Absorption spectra were collected in toluene. Elemental analyses were performed by Atlantic Microlab, Inc. Melting points are uncorrected. Silica gel (Baker 40 μm average particle size) and alumina (Fisher, 80–200 mesh) were used for column chromatography. Preparative size exclusion chromatography (SEC) was performed using BioRad Bio-Beads SX-1 (200–400 mesh) beads. Analytical SEC was performed using an HP 1090 Liquid Chromatograph (column size=1000 Å; flow rate=0.800 mL/min; solvent=THF; quantitation at 420 nm; oven temperature 40° C.). Toluene and triethylamine were freshly distilled from CaH$_2$ and sparged of oxygen prior to use. Pd$_2$(dba)$_3$, P(o-tol)$_3$, and all other reagents were purchased from Aldrich and used as received. All Sonogashira reactions were performed using a Schlenk line. Room temperature was determined to be 21–22° C. using a calibrated thermometer (Fisher).

Compounds 2a–f (Littler, B. J. et al. *J. Org. Chem.* 1999, 64, 1391–1396); 3a–b (Rao, P. D. et al. *J. Org. Chem.* 2000, 65, 1084–1092); 4a, 5c, and 5e (Rao, P. D. et al. *J. Org. Chem.* 2000, 65, 7323–7344); 5f (Gryko, D. and Lindsey, J. S. *J. Org. Chem.* 2000, 65, 2249–2252); Mg-6h (Wagner, R. W. et al. *Chem. Mater.* 1999, 11, 2974–2983); Mg-6i' (Li, F. et al. *J. Mater. Chem.* 1997, 7, 1245–1262); Zn-6i' (Wagner, R. W. et al. *J. Am. Chem. Soc.* 1996, 118, 11166–11180);

Zn-6j (Li, J. et al. *J. Am. Chem. Soc.* 1999, 121, 8927–8940) were prepared as described in the literature. Compound Zn-1a was obtained commercially. Free base porphyrins 1c (Rao, P. D. et al. *J. Org. Chem.* 2000, 65, 1084–1092); 1d and 1e (Rao, P. D. et al. *J. Org. Chem.* 2000, 65, 7323–7344); and 1f (Nishino, N. et al. *J. Org. Chem.* 1996, 61, 7534–7544) were prepared as described in the literature and were metalated as needed.

EXAMPLES 1–52

Results and Discussion

I. Molecular Design

Achieving the directed flow of energy in an array of porphyrins has frequently been achieved with a metalloporphyrin and a free base porphyrin as the donor-acceptor pair, respectively. However, the cation radicals of free base porphyrins often are somewhat unstable, unlike the cation radicals of metalloporphyrins. A magnesium (Mg) porphyrin typically absorbs at ~10 nm longer wavelength than that of the corresponding zinc (Zn) porphyrin, enabling Mg porphyrins to serve as the energy acceptor with a Zn porphyrin as the energy donor. While a Mg porphyrin in general has a less positive $E_{1/2}$ value than that of the corresponding Zn porphyrin, the $E_{1/2}$ value of porphyrins can be tuned by incorporating electron-deficient or electron-rich substituents at the perimeter of the macrocycle with little change on the position of the long wavelength absorption band. Thus, the design we sought incorporated an electron-deficient Mg porphyrin as the charge-separation unit to be attached to a semiconductor. For attachment to a metal-oxide semiconductor, a carboxylic acid group was required on the Mg porphyrin. Zn porphyrins of less positive $E_{1/2}$ values (increasing electron-richness) could then be incorporated in the rod with increasing distance from the Mg porphyrin.

To identify suitable substituents with Zn or Mg porphyrins, an initial survey was performed on a small family of metalloporphyrins. The free base porphyrins had been prepared previously and were metalated as required under standard conditions. The results are shown in Table 1. The Mg porphyrin must have a more positive $E_{1/2}$ value and a lower energy long-wavelength absorption band than any of the Zn porphyrins in the array. Considering ZnTPP (Zn-1a) or ZnTMP as the least electron-rich of any Zn porphyrin that might be employed, a Mg porphyrin with two pentafluorophenyl groups (Mg-1e) satisfies both criteria whereas one pentafluorophenyl group yields a Mg porphyrin that is insufficiently electron-deficient (Mg-1d). We investigated the use of trifluoromethyl groups which cause a large positive shift in the $E_{1/2}$ value (e.g., Zn-1f) but were unable to obtain the magnesium chelate. The introduction of two p-methoxy groups to ZnTPP shifts the $E_{1/2}$ value to less positive values by ~90 mV. With these results in hand, we considered designs to be satisfactory comprised of the following sequence of pigments: a TMP-type Zn porphyrin bearing two alkoxy groups, a TMP-type Zn porphyrin bearing one alkoxy group, a TMP-type Zn porphyrin without other substituents, and a Mg porphyrin bearing two pentafluorophenyl groups. The presence of a p-carboxy group on the Mg porphyrin should not have adverse effect on the desired property of the array, only shifting the $E_{1/2}$ to a more positive value compared with the benchmark compound Mg-1e.

TABLE 1

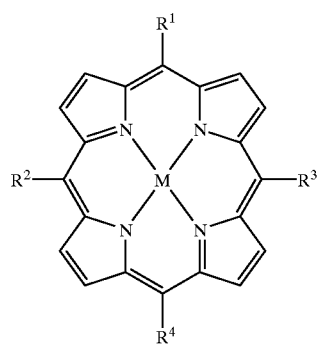

$Q_{(0,0)}$ Absorption Maxima and Electrochemical Data for Representative Metalloporphyrins.

| Porphyrin | R¹ | R² | R³ | R⁴ | M | $\lambda_{abs}$ $Q_{(0,0)}$ | $E_{1/2}$ (mV)[a] |
|---|---|---|---|---|---|---|---|
| Zn-1a | –C₆H₅ | –C₆H₅ | –C₆H₅ | –C₆H₅ | Zn | 590 | 0.510 |
| Zn-1c | –C₆H₄–OCH₃ | –C₆H₅ | –C₆H₄–OCH₃ | –C₆H₅ | Zn | 594 | 0.429 |

TABLE 1-continued

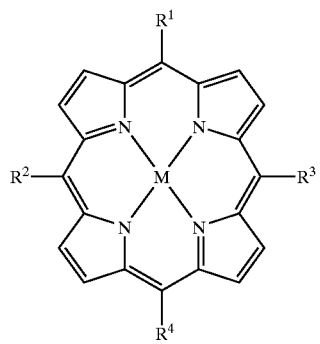

$Q_{(0,0)}$ Absorption Maxima and Electrochemical Data for Representative Metalloporphyrins.

| Porphyrin | R$^1$ | R$^2$ | R$^3$ | R$^4$ | M | $\lambda_{abs}$ $Q_{(0,0)}$ | $E_{1/2}$ (mV)$^a$ |
|---|---|---|---|---|---|---|---|
| Mg-1d | —C$_6$F$_5$ | —⟨C$_6$H$_4$⟩—CH$_3$ | —⟨C$_6$H$_5$⟩ | —⟨C$_6$H$_4$⟩—CH$_3$ | Mg | 604 | 0.424 |
| Mg-1e | —C$_6$F$_5$ | —⟨C$_6$H$_5$⟩ | —C$_6$F$_5$ | —⟨C$_6$H$_5$⟩ | Mg | 604 | 0.560 |
| Zn-1f | —CF$_3$ | -mesityl | —CF$_3$ | -mesityl | Zn | 588 | 0.865 |

$^a$vs Ag/Ag$^+$; scan rate 0.1 Vs$^{-1}$.

Two other points that bear on design are noteworthy. First, domains of adjacent isoenergetic pigments can be employed, affording reversible transfer processes. Second, we have shown that excited-state energy migration and ground-state hole-hopping can occur rapidly among non-nearest neighbor porphyrins. Thus, the presence of one pigment in a rod with slightly inappropriate energy will slow, but not cause termination of, the flow of excited-state energy or ground-state holes.

II. Synthesis of Porphyrin Building Blocks.

Many of the porphyrin building-blocks employed in the examples above were synthesized following a method for preparing porphyrins bearing up to four different meso-substituents. The starting point for such porphyrins begins with the synthesis of 5-substituted dipyrromethanes. Thus, the one-flask reaction of an aldehyde and excess pyrrole at room temperature affords analytically pure dipyrromethanes 2a–g (Scheme 11A) (Littler, B. J. et al., *J. Org. Chem.* 1999, 64, 1391–1396). Dipyrromethanes 2a–e were purified by distillation followed by recrystallization while dipyrromethanes 2f–g were purified by column chromatography followed by recrystallization. These dipyrromethanes are key precursors to the porphyrin building blocks used in this study.

Scheme 11A

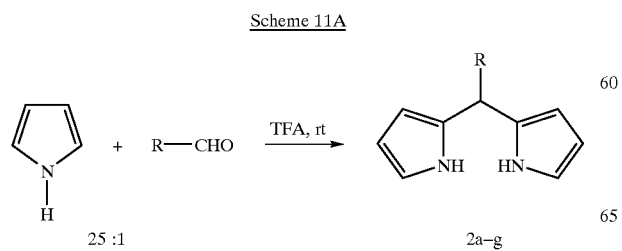

-continued

R

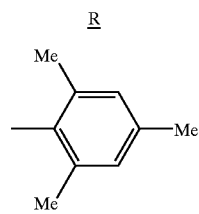 2a

 2c

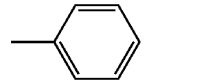 2d

 2e

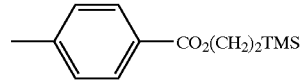 2f (40%)  2g

Dipyrromethane 2a serves as the key starting material in the synthesis of monoacyl dipyrromethanes 4a–b (Scheme 11B). Efficient monoacylation of 2a was achieved by treatment with EtMgBr followed by addition of S-2-pyridyl thioester 3a or 3b (Rao, P. D. et al., *J. Org. Chem.* 2000, 65, 1084–1092). Subsequent acylation of 4a–b was achieved by treatment with EtMgBr followed by reaction with an acid chloride (Rao, P. D. et al., *J. Org. Chem.* 2000, 65, 7323–7344), affording diacyldipyrromethanes 5a–c in good yields. These compounds are important precursors in the synthesis of trans-$AB_2C$ and ABCD porphyrin building blocks.

Scheme 11B

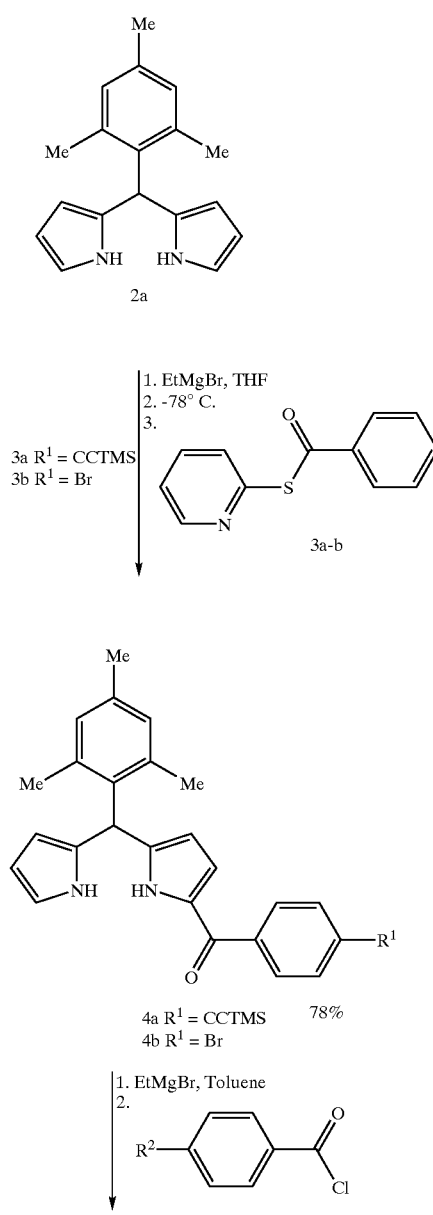

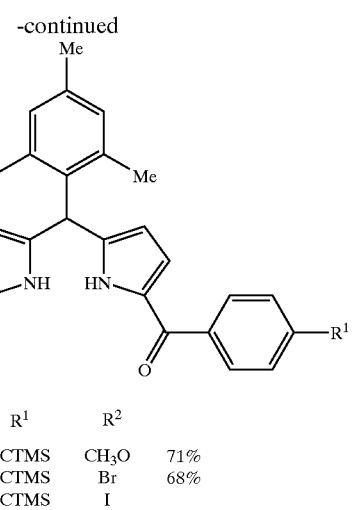

| | $R^1$ | $R^2$ | |
|---|---|---|---|
| 5a | CCTMS | $CH_3O$ | 71% |
| 5b | CCTMS | Br | 68% |
| 5c | CCTMS | I | |

Following a procedure to prepare trans-$AB_2C$-substituted porphyrins (Rao, P. D. et al., *J. Org. Chem.* 2000, 65, 7323–7344), dipyrromethane 2b,d–e were treated with EtMgBr and pentafluorobenzoyl chloride, affording diacyldipyrromethane 5d–f (Scheme 11C). Compounds 5d–e serve as direct precursors to trans-$AB_2C$ porphyrins while compound 5f is employed as a building block in the synthesis of an $A_3B$ porphyrin.

Scheme 11C

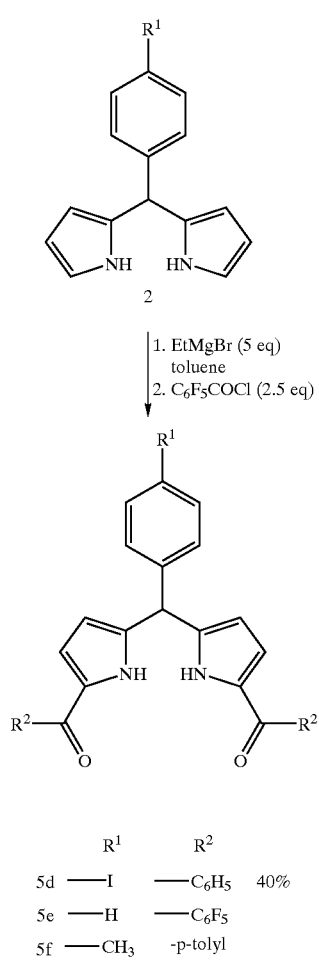

| | $R^1$ | $R^2$ | |
|---|---|---|---|
| 5d | —I | —$C_6H_5$ | 40% |
| 5e | —H | —$C_6F_5$ | |
| 5f | —$CH_3$ | -p-tolyl | |

The target porphyrin building blocks were prepared by reducing the desired diacyldipyrromethane (5a–f) to the corresponding dipyrromethane-dicarbinol using excess NaBH₄ (Rao, P. D. et al., *J. Org. Chem.* 2000, 65, 7323–7344). The dipyrromethane-dicarbinol was then condensed with the desired dipyrromethane (2a–g) under non-scrambling conditions (30 mM TFA in CH₃CN at room temperature) for a few minutes, followed by the addition of DDQ to achieve oxidation (Scheme 12) (Rao, P. D. et al., *J. Org. Chem.* 2000, 65, 7323–7344). Following this procedure, ABCD-porphyrins 6a–b, trans-AB₂C-porphyrins 6c–f, and A₃B-porphyrin 6g were prepared in yields ranging from 18–26%. In each case, analysis of the crude reaction mixture by LD-MS showed no detectable scrambling. The porphyrins were purified in the following manner: (1) filtration of the crude reaction mixture through alumina to remove quinone species, (2) removal of solvent under reduced pressure, (3) one silica gel chromatography procedure to remove non-porphyrinic pigments, and (4) sonication of the porphyrin product suspended in methanol followed by filtration.

Scheme 12

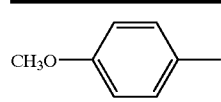

| R¹ | R² | R³ | R⁴ | Product | Yield |
|---|---|---|---|---|---|
| 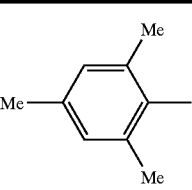 | 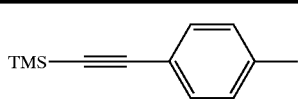 | 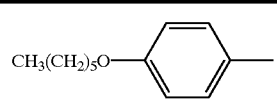 | 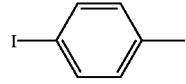 | 6a | 22% |
| 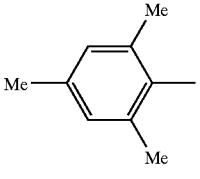 | 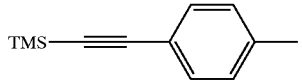 | 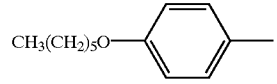 | 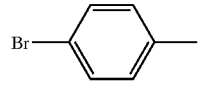 | 6b | 22% |
| 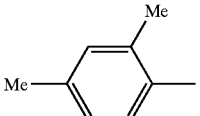 | 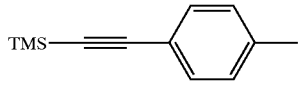 | 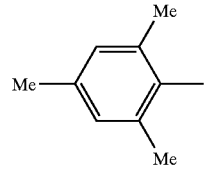 | 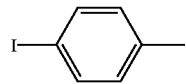 | 6c | 26% |
| 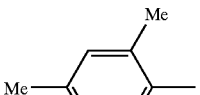 | 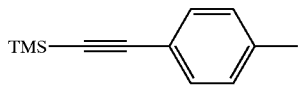 | 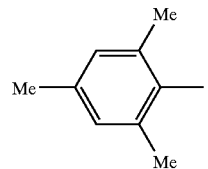 | | 6d | 22% |

-continued

Scheme 12

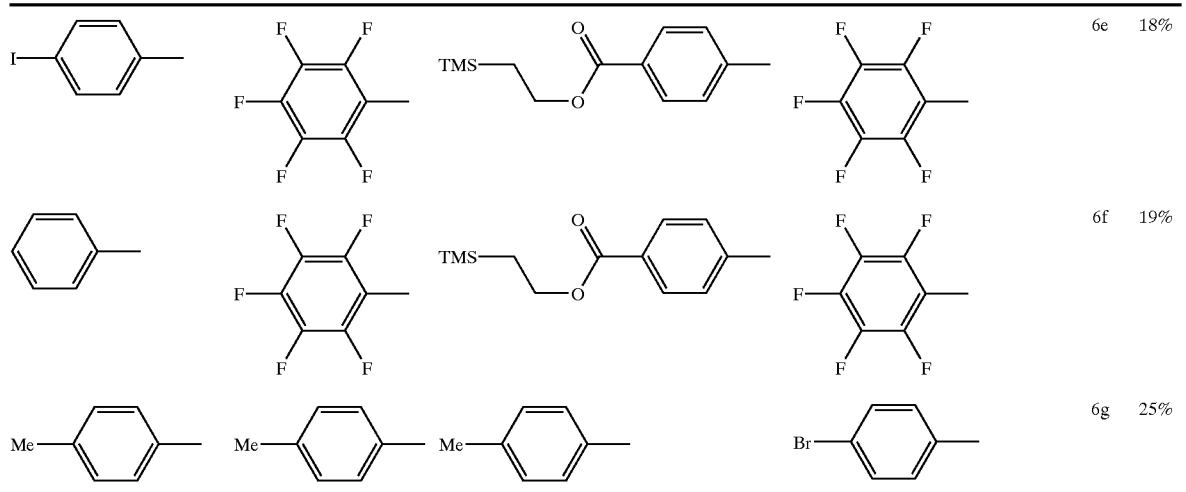

Porphyrins 6a–d and 6g were metalated using Zn(OAc)$_2$.2H$_2$O in CHCl$_3$ to afford the zinc chelates Zn-6a–d and Zn-6g in yields ranging from 75–94%. Porphyrins 6e–f were metalated using MgBr$_2$.O(Et)$_2$ and TEA in CH$_2$Cl$_2$ to afford the magnesium chelate Mg-6e in 88–91% yield. Porphyrin 6g was also metalated using MgI$_2$ and diisopropylethylamine in CH$_2$Cl$_2$ to afford the magnesium chelate Mg-6g in 81% yield (Lindsey, J. S., Woodford, J. N. *Inorg. Chem.* 1995, 34, 1063–1069). Removal of the trimethylsilyl protecting group of porphyrins Zn-6a and Zn-6c was achieved using TBAF in THF/CHCl$_3$ (2:1) to afford porphyrins Zn-6a' and Zn-6c' in 96% or 77% yield, respectively. Porphyrins Mg-6h, Mg-6i', and Zn-6i' were each obtained from a mixed-aldehyde condensation (Lindsey, J. S., Wagner, R. W. *J. Org. Chem.* 1989, 54, 828–836) followed by metal insertion and subsequent deprotection where required. These porphyrin building blocks were subsequently employed in the cross-coupling experiments and porphyrin array syntheses described below.

III. Demonstration of Successive I/Br Coupling

The synthesis of diphenylethyne-linked multiporphyrin arrays has been achieved by palladium-catalyzed cross-coupling of porphyrins bearing iodophenyl and/or ethynylphenyl substituents (Sharman, W. M., Van Lier, J. E. *J. Porphyrins Phthalocyanines* 2000, 4, 441–453). In a divergent, iterative approach, Sonogashira coupling of an ethynyl-porphyrin and a porphyrin bearing an iodo group and a trimethylsilyl-protected ethyne affords a porphyrin dyad (Note: The coupling of porphyrin building blocks requires reaction conditions for the Sonogashira reaction that are different in several regards from those typically employed: (1) mild conditions must be employed to avoid demetalation and transmetalation reactions of metalloporphyrins, and to avoid metalation of free base porphyrins; (2) copper cannot be employed, at least in the presence of free base porphyrins; (3) the limited solubility of porphyrins requires couplings to be performed at modest concentrations (0.01–0.001 M); and (4) the iodo-porphyrin and the ethynyl-porphyrin generally need to be employed in a 1:1 ratio given the value of both components and the necessity for chromatographic workup. Accordingly, the conditions we developed for coupling iodo-porphyrins and ethynyl-porphyrins employ Pd$_2$(dba)$_3$, and tri-o-tolylphosphine in toluene/triethylamine (5:1) at 35° C. in the absence of copper cocatalysts with equimolar amounts (2.5 mM each) of the two porphyrins.). Cleavage of the trimethylsilyl-protected ethyne (TMSE) sets the stage for a second Pd-mediated coupling reaction with another bifunctional iodo/TMSE porphyrin. This strategy works well for small arrays but lacks the power of convergence needed to gain entry into larger arrays. Extension of the Sonogashira reaction to include bromo-substituted porphyrins would add versatility in the synthesis, particularly if the lower degree of reactivity of the bromo versus iodo functionality enabled successive Sonogashira coupling. In this regard, several examples with smaller organic molecules have demonstrated selective coupling of the iodo functionality in the presence of the bromo functional group (Henze, O. et al. *Chem. Eur. J.* 2000, 6, 2362–2367; Nicoud, J.-F. and Wong, M. S. *Tetrahedron Lett.* 1994, 35, 6113–6116; Höger, S. et al. *Chem. Eur. J.* 1998, 4, 2423–2434; Tobe, Y. et al. *Angew. Chem. Int. Ed.* 1998, 37, 1285–1287). However, no attempts have been made to examine bromo-porphyrins in this capacity. Such bromo/iodo-substituted porphyrin building blocks should prove to be valuable components for achieving convergence in the synthesis of multiporphyrin arrays.

A. Chemoselectivity of Iodo versus Bromo Coupling. To identify conditions for performing successive Sonogashira couplings, we first examined the selectivity of cross-coupling of an iodo-porphyrin and an ethynyl-porphyrin in the presence of a bromo-porphyrin. In this competition experiment, equimolar quantities of Mg-6g, Mg-6h and Mg-6i' were subjected to Sonogashira coupling conditions developed previously for the synthesis of multiporphyrin arrays (Scheme 13) (Wagner, R. W. et al. *J. Org. Chem.* 1995, 60, 5266–5273; Wagner, R. W. et al. *Chem. Mater.* 1999, 11, 2974–2983). Briefly, the coupling of porphyrin building blocks requires reaction conditions for the Sonogashira reaction that are different in several regards from those typically employed (Sonogashira, K. et al. *Tetrahedron Lett.* 1975, 4467–4470; Takahashi, S. et al. *Synthesis* 1980, 627–630): (1) mild conditions must be employed to avoid demetalation and transmetalation reactions of metalloporphyrins, and to avoid metalation of free base porphyrins; (2) copper cannot be employed, at least in the presence of free base porphyrins; (3) the limited solubility of porphyrins requires couplings to be performed at modest concentrations (0.01–0.001 M); and (4) the iodo-porphyrin and the ethynyl-porphyrin generally need to be employed in a 1:1 ratio given the value of both components and the necessity for chromatographic workup. Accordingly, the conditions employed herein for coupling iodo-porphyrins and ethynyl-porphyrins employ $Pd_2(dba)_3$, and tri-o-tolylphosphine in toluene/triethylamine (5:1) at 35° C. in the absence of copper cocatalysts with equimolar amounts (~2.5 mM each) of the two porphyrins (Wagner, R. W. et al. *J. Org. Chem.* 1995, 60, 5266–5273; Wagner, R. W. et al. *Chem. Mater.* 1999, 11, 2974–2983). The progress of this reaction was monitored by analytical SEC and LD-MS. Tolyl and mesityl groups were employed in the bromo-porphyrin and iodo-porphyrin, respectively, to provide an adequate mass difference between dyads 7 and 8 allowing for analysis by LD-MS (MW of 7=1546; MW of 8=1464). Dyad 7 is the product from the desired iodo+ethyne coupling reaction; dyad 8 is the product from unwanted bromo+ethyne coupling.

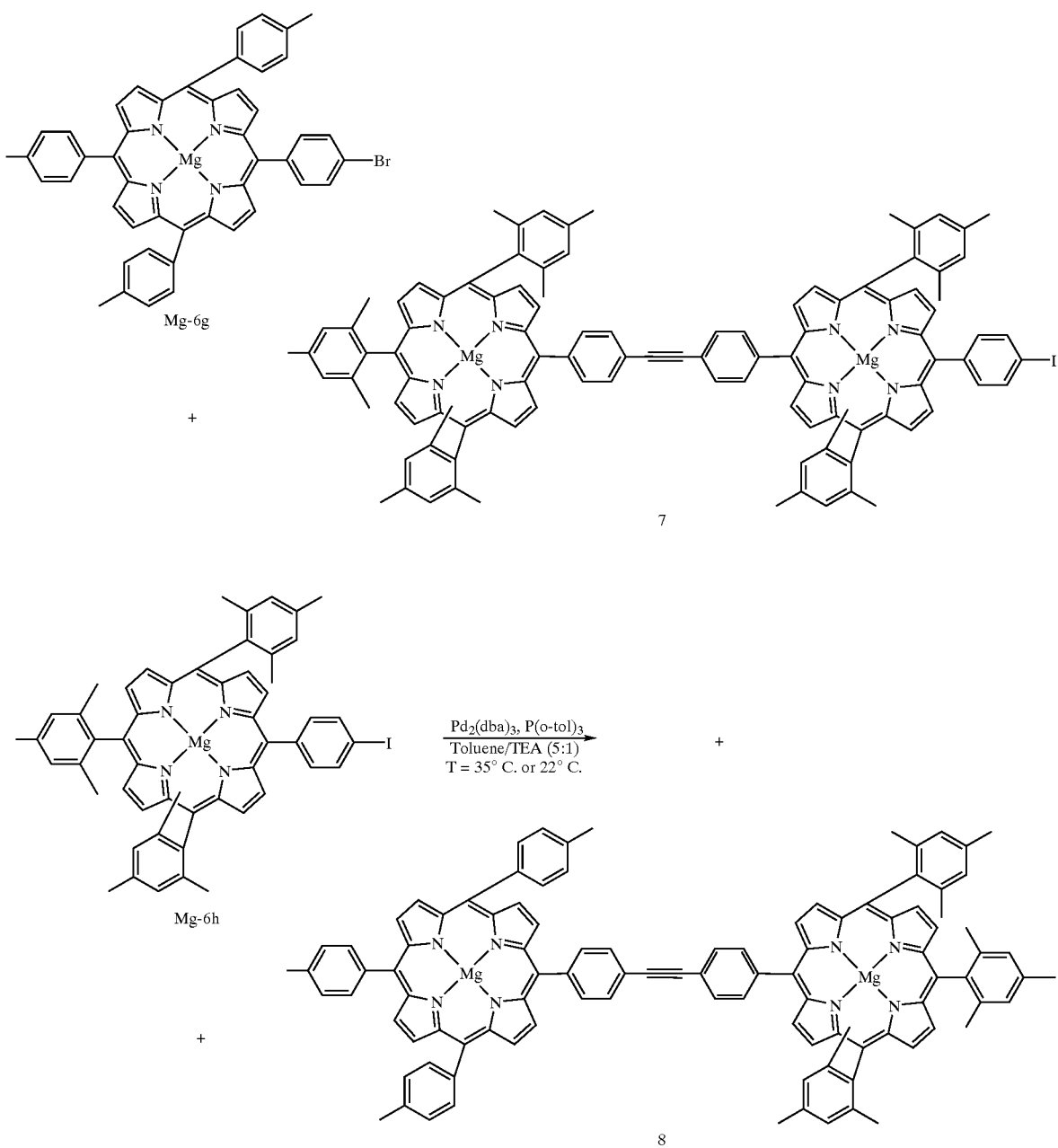

Scheme 13

-continued

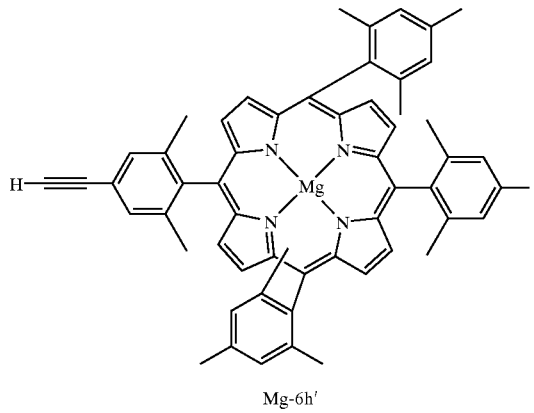

Mg-6h'

Figure 2:
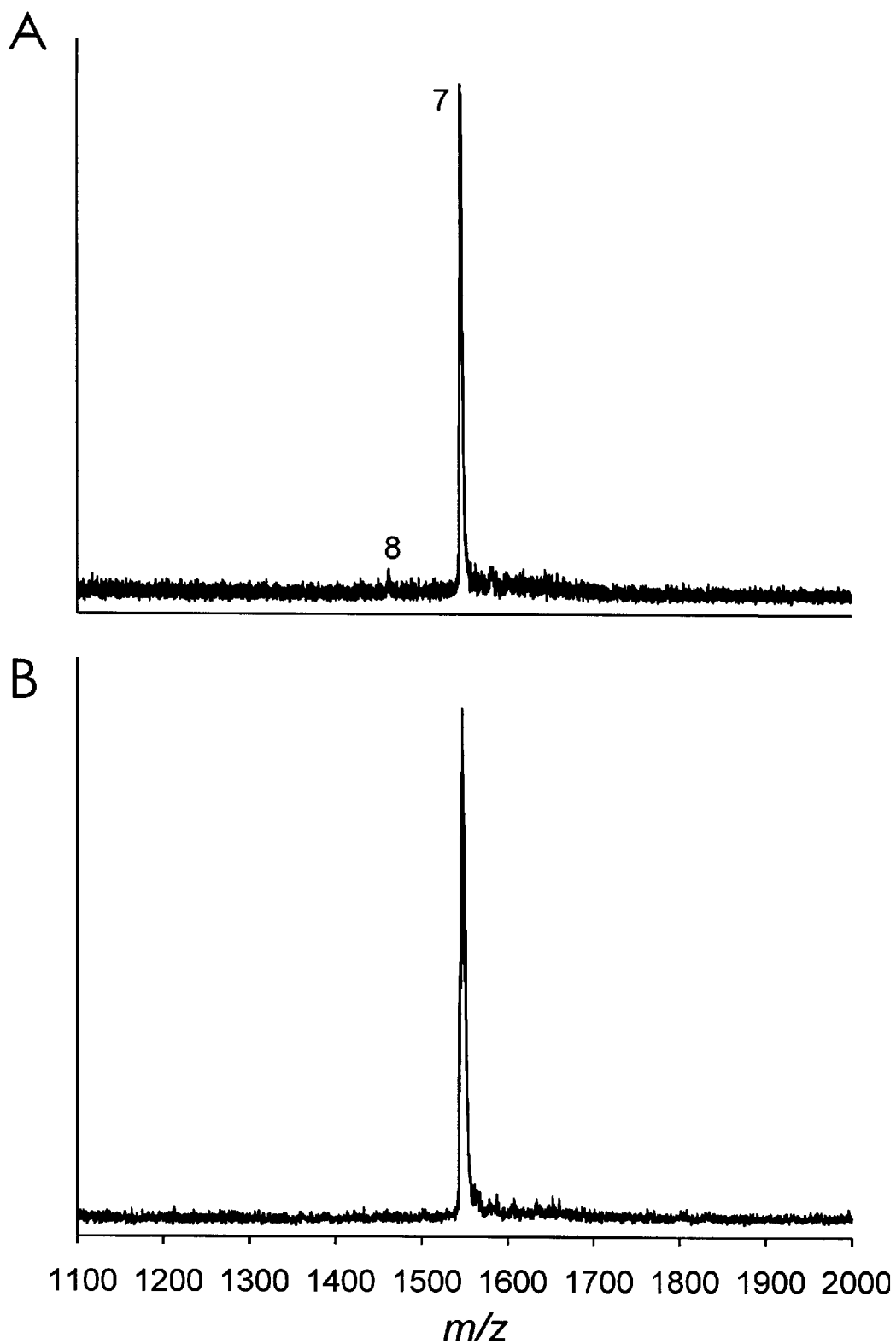
FIG. 2. (a) LD-MS of dyad fraction from competition experiments performed at 35° C. (b) MALDI-MS of dyad fraction from competition experiments performed at 22° C. Only dyad 7 is detected.

Analysis of both crude and purified samples by LD-MS showed a large mass envelope centered at 1546 amu corresponding to dyad 7, as well as a small peak centered at 1464 amu corresponding to dyad 8 (FIG. 2A). These results indicate preferential but not exclusive selectivity for Sonogashira coupling with the iodo-porphyrin versus bromoporphyrin. Upon reaction at room temperature (22° C.) instead of 35° C., both the MALDI (POPOP) and LD-MS spectra of the crude and purified samples showed a very clean dyad mass region. FIG. 2B shows the MALDI-MS (POPOP) spectrum of the purified dyad fraction. No detectable mass envelope corresponding to 8 could be detected. Thus, the lower reaction temperature reduces the amount of bromo+ethyne coupling to undetectable levels (by LD-MS analysis). However, the lower reaction temperature also slowed the rate of cross-coupling as evidenced by the analytical SEC data: after 2 h the percent conversion to dyad was nearly twice as high at 35° C. compared to 22° C. (63% vs. 34%, uncorrected). Nevertheless, the slightly lower reaction temperature does not produce detectable amounts of bromo coupling products, making it the preferred reaction condition.

Figure 3:
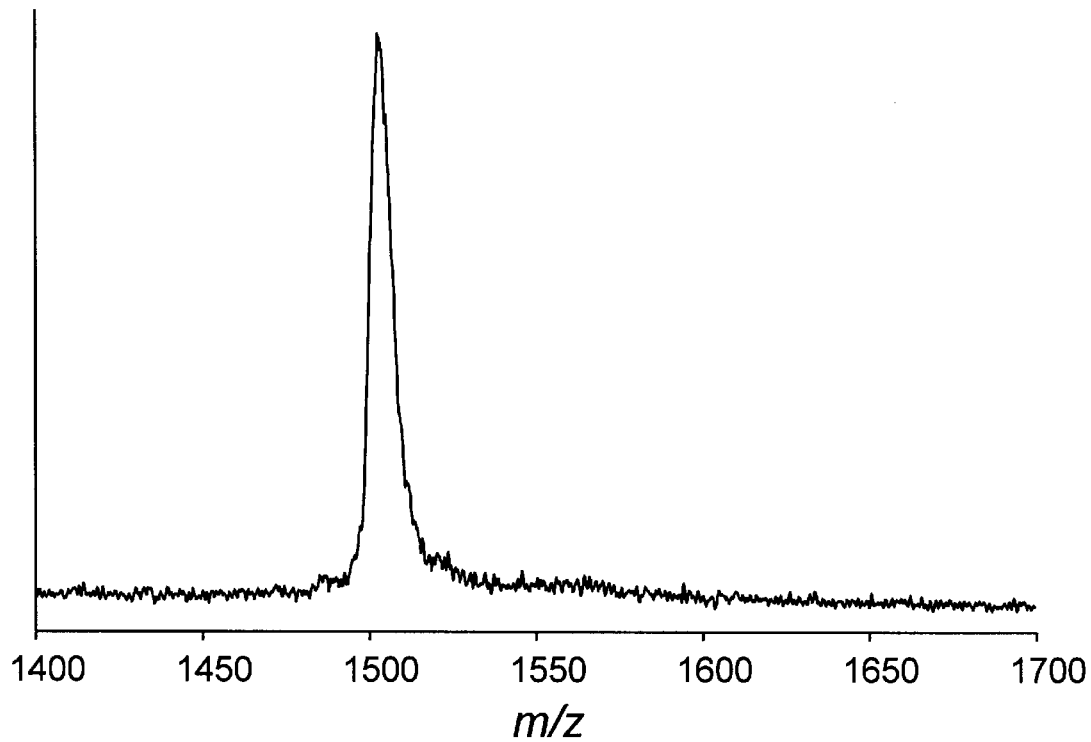
FIG. 3. LD-MS of purified dyad 9 (reaction temperature= 80° C.).

B. Sonogashira Coupling with Bromo-porphyrins. The ability to perform successive Sonogashira couplings with iodo and bromo groups requires satisfactory conditions for bromo coupling. In the first experiment, porphyrins Zn-6g and Zn-6i' were subjected to our standard Pd-coupling conditions with two modifications: (1) a 2:1 ratio of P(o-tol)$_3$:Pd was employed (a 2:1 ligand to catalyst ratio was employed instead of the usual 4:1 ratio to yield a more active catalytic system), and (2) the reaction temperature was 80° C. (Scheme 14). Aliquots were removed and analyzed at 1 and 3 h by SEC and LD-MS, then the crude reaction mixture was purified according to established procedures (Wagner, R. W. et al. *J. Org. Chem.* 1995, 60, 5266–5273; Wagner, R. W. et al. *Chem. Mater.* 1999, 11, 2974–2983). The analytical SEC data showed no change in the amount of dyad formation at 1 h and 3 h (60% dyad after 1 h; 62% dyad after 3 h). There was a significant amount of higher molecular weight material (HMWM) present at both timepoints (14% after 1 h; 17% after 3 h). The LD-MS data of purified 9 showed an intense peak centered at 1550 amu (FIG. 3). No observable peaks resulting from tolylation (m/z=1642 amu) or homocoupling (m/z=1512 amu) could be detected, indicating the cleanliness of this reaction.

Scheme 14

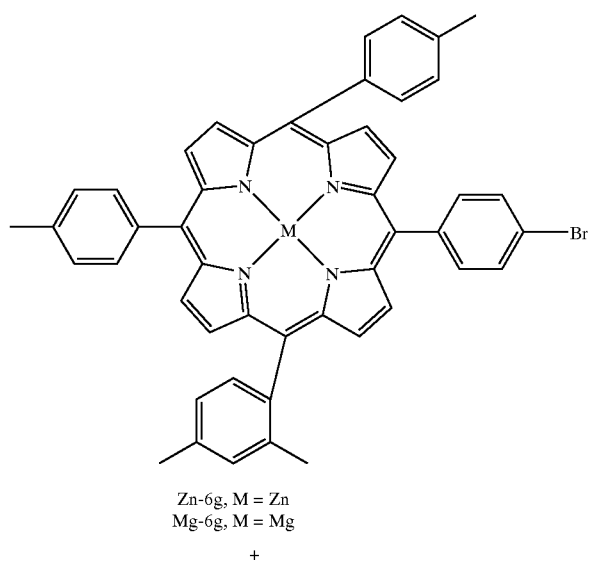

Zn-6g, M = Zn
Mg-6g, M = Mg

+

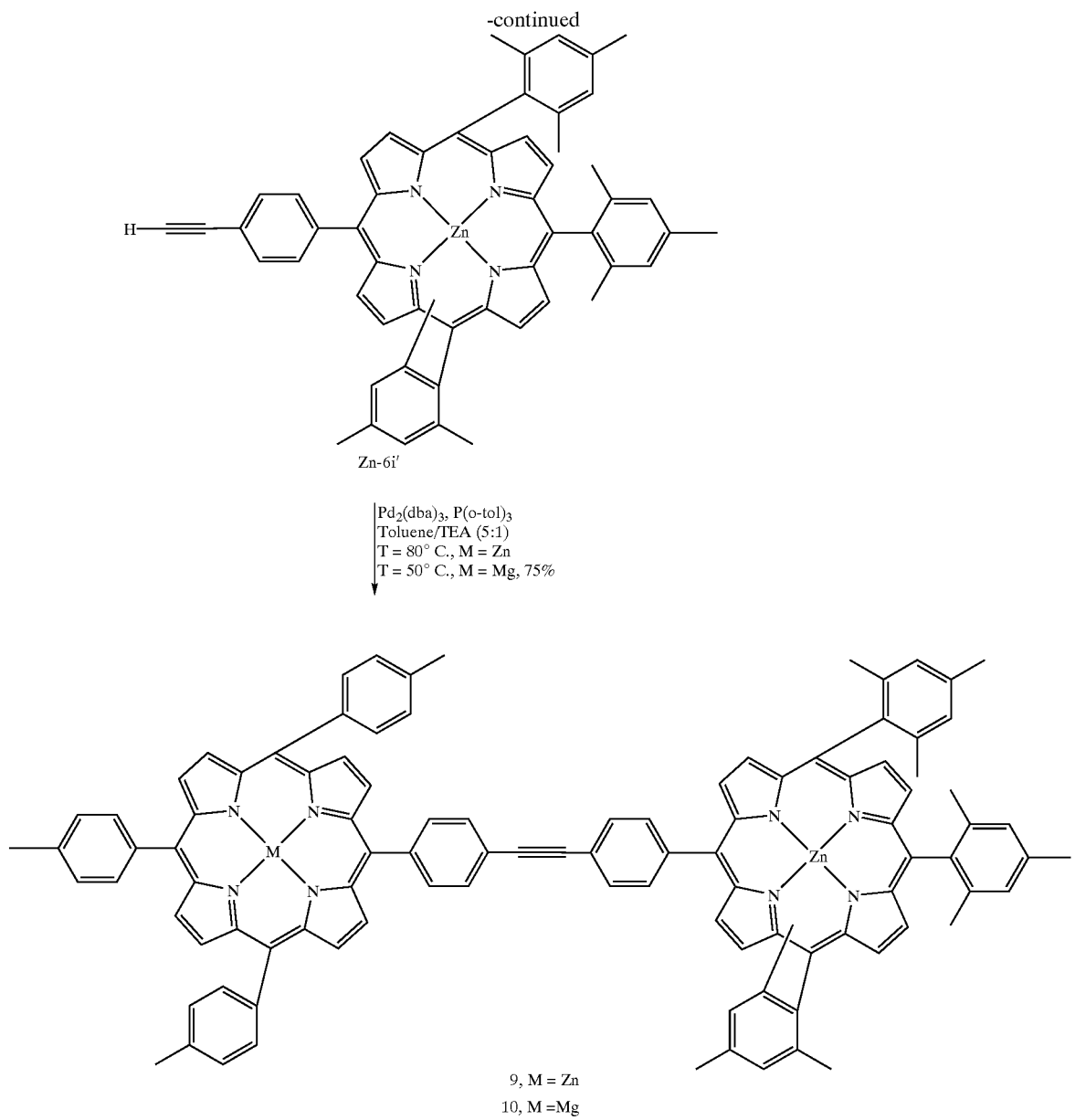

A second experiment was performed with the following modifications: (1) the reaction was carried out at 50° C., (2) a 4:1 ratio of P(o-tol)$_3$:Pd was employed, and (3) magnesium bromo-porphyrin Mg-6g was used in place of zinc bromo-porphyrin Zn-6g to test compatibility with the more labile magnesium (Scheme 14). SEC analysis showed 36% dyad formation within 1 h of reaction. This value increased to only 38% after 2 h, therefore a second batch of Pd$_2$(dba)$_3$ and P(o-tol)$_3$ was added. After a further 1 h (3.5 h total reaction time), the analytical SEC showed a 77% yield of dyad, a significant improvement compared to the 1 and 2 h timepoints. Importantly, the percentage of HMWM was much lower than the previous experiment, which is likely due to the reduced reaction temperature and/or the lower ratio of palladium to ligand employed. Chromatographic workup afforded dyad 10 in 75% yield. The $^1$H NMR and LD-MS spectra of dyad 10 showed no detectable impurities. Although additional amounts of palladium and phosphine ligand were employed to obtain the high yield, this procedure demonstrates clean Sonogashira coupling of bromo-porphyrins under gentle reaction conditions.

C. Sonogashira Coupling between Br/CCH and I/CCTMS Porphyrin Building Blocks. We applied the chemoselective Sonogashira conditions toward the synthesis of several porphyrin arrays. The reaction of bromo/ethynyl porphyrin Zn-6c' and iodo/TMS-ethynyl porphyrin Zn-6b was performed at room temperature (Scheme 15). After 1 h, SEC analysis showed approximately 27% conversion to dyad 11. A second batch of palladium and ligand was added to the reaction after 1.5 h; after 3.5 h total the analytical SEC showed nearly 70% dimer, 23% monomers and 8% of HMWM. Subsequent purification afforded the Br/TMS dyad 11 in 60% yield.

Scheme 15

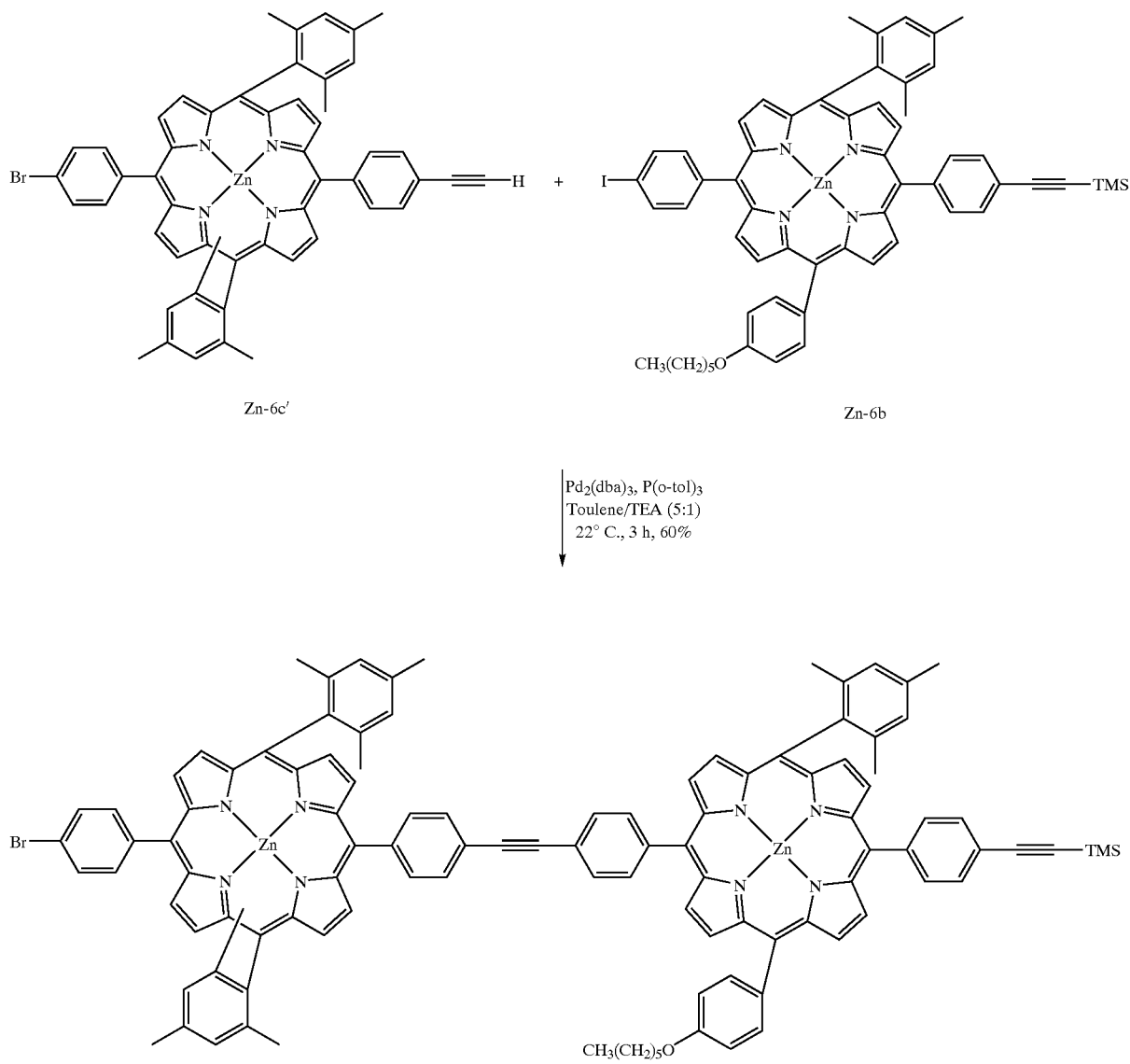

IV. Synthesis of Porphyrin Light-Harvesting Rods

A. Triad 13. We employed the procedures developed for successive Sonogashira coupling of iodo- and bromo-substituted porphyrin building blocks to prepare a series of porphyrin light-harvesting (LH) rods. These arrays are designed to meet the criteria for intrinsic rectification of the migration of excited-state energy and ground-state holes (vida supra). The synthesis of a linear triad does not offer the possibility for convergence; therefore we utilized stepwise Sonogashira coupling of iodo-porphyrin and ethynyl-porphyrin building blocks. The synthesis of triad 13 is shown in Scheme 16. Synthesis of triad 13 could be initiated from either terminus. Because of the increased lability of magnesium porphyrins, we decided to introduce porphyrin Mg-6e in the last coupling step to minimize the handling of magnesium porphyrins. Monoporphyrin building blocks Zn-6a' and Zn-6b were reacted under standard Pd-coupling conditions developed in our lab (Wagner, R. W. et al. *J. Org. Chem.* 1995, 60, 5266–5273; Wagner, R. W. et al. *Chem. Mater.* 1999, 11, 2974–2983). Under these conditions, the trimethylsilylethynyl-functionalized dimer was isolated in 57% yield. Removal of the TMS protecting group using TBAF in THF furnished porphyrin dyad 12' in 91% yield. Dyad 12' was then allowed to react with porphyrin Mg-6e to produce the desired porphyrin triad 13 in 75% yield. Triad 13 was purified according to a three column procedure: (1) an alumina column [CHCl$_3$/hexanes (4:1)] to remove palladium and most of the ligand, (2) an SEC column (THF) to recover the almost pure porphyrin triad, and (3) an alumina column [CHCl$_3$/hexanes (4:1) with slow enrichment with THF] for final purification. Triad 13 was found to be poorly soluble in CHCl$_3$ and CH$_2$Cl$_2$, but moderately soluble in THF and toluene.

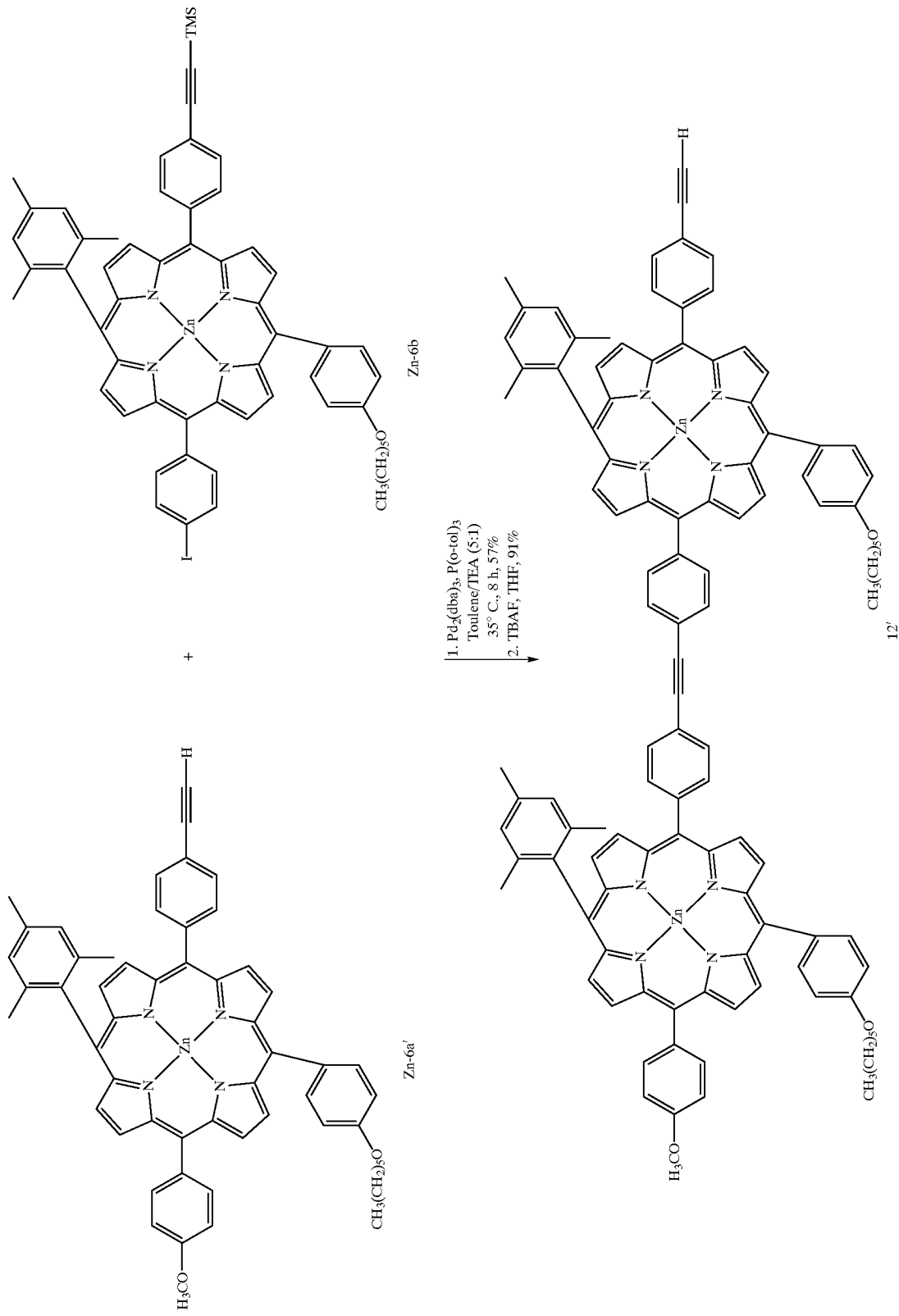

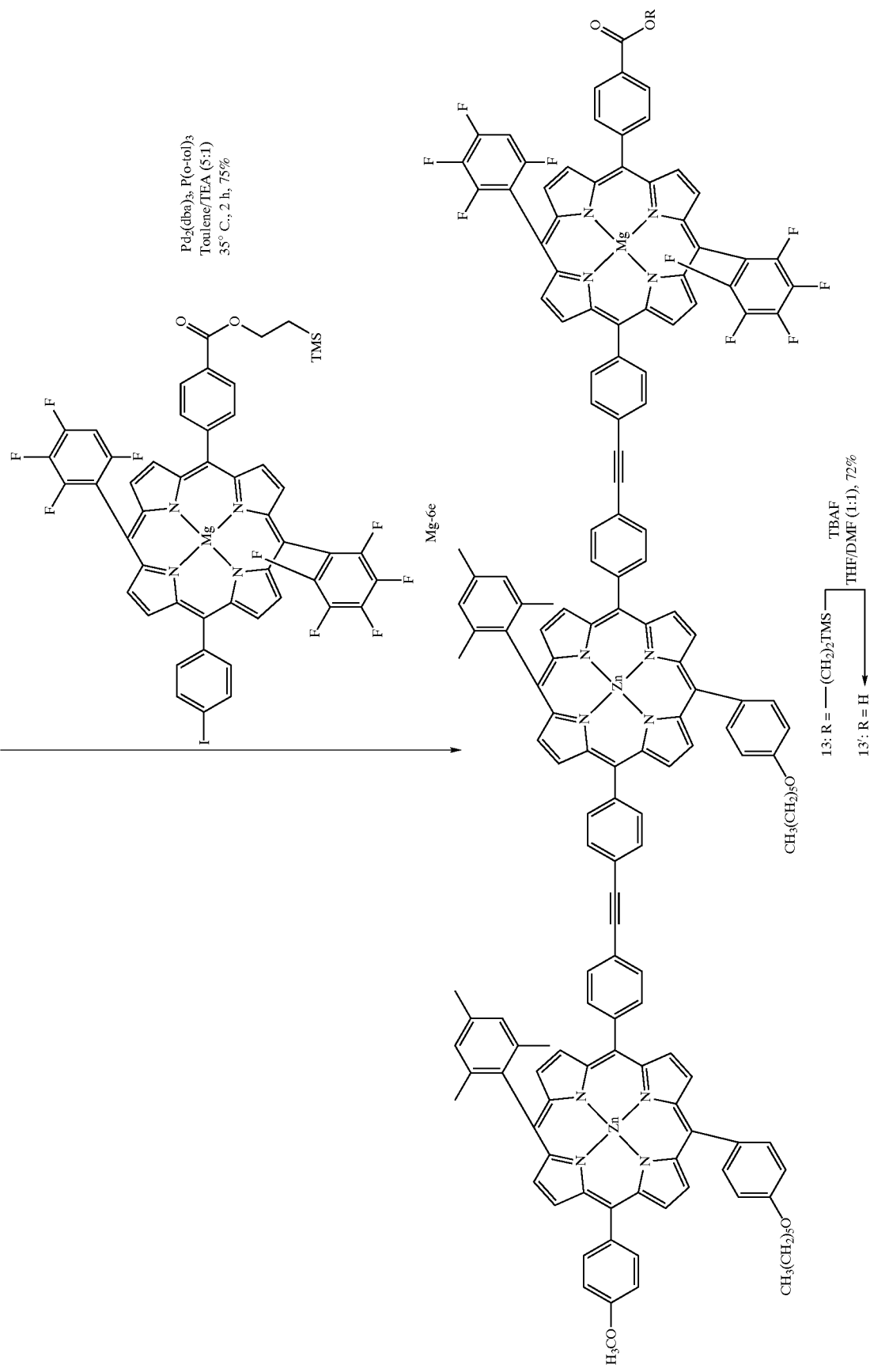

Deprotection of 13 was achieved using TBAF (1.0 M in THF) in DMF/THF (1:1) (Scheme 16). After 24 h, LD-MS showed no detection of the starting material. Isolation of the product was achieved by filtration followed by washing the solid with copious amounts of water, then methanol to yield 13' in 72% yield. The carboxy-terminated array has the ability to bind to $TiO_2$ as well as other semiconductor substrates, allowing for evaluation of solar cell performance.

B. Tetrad 15. As the size of the multiporphyrin array increases, so too does the number of possible synthetic routes. Specifically, to prepare a linear porphyrin tetrad, one possible approach is to perform a series of coupling and deprotection steps with suitable monomeric porphyrin building blocks. However, a more desirable approach lies in a convergent coupling of two porphyrin dimeric building blocks. The development of successive iodo/bromo Sonogashira coupling allows for the latter approach to be realized. Thus the convergent synthesis of tetrad 15 is outlined in Scheme 17. Selective Sonogashira coupling of bromo/ethynyl-porphyrin Zn-6c' and iodo-porphyrin Mg-6e at room temperature afforded bromo-porphyrin dyad 14 in 60% yield. Convergent Sonogashira coupling of 12' and 14 at 50° C. for 5 h yielded tetrad 15 in 43% yield. The solubility of 15 was poor in chlorinated solvents; the best solubility was observed with mixtures of toluene and THF. Tetrad 15' was prepared in 50% yield by deprotection of 15 using TBAF in THF/DMF (10:1) at 60° C. for 17 h.

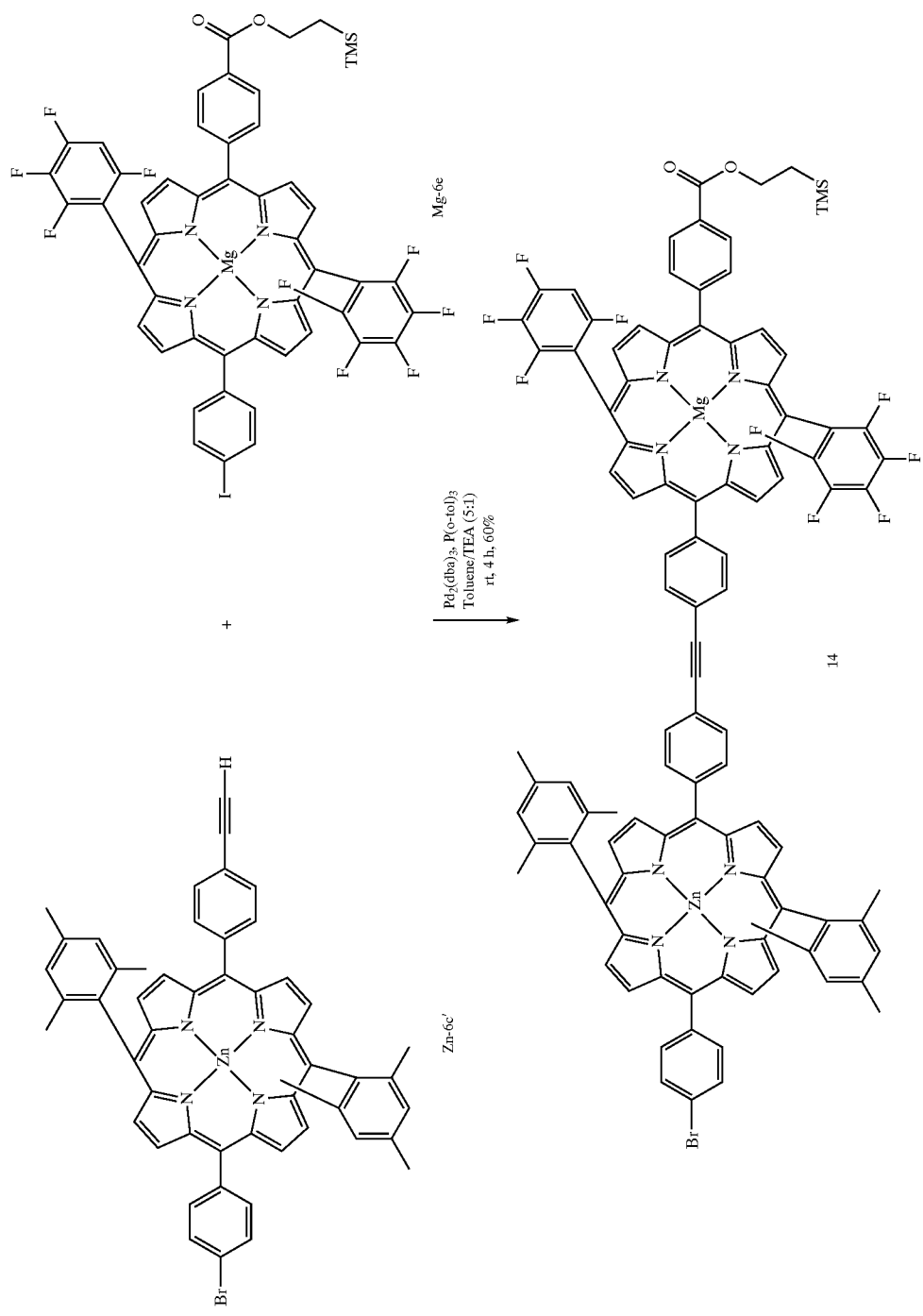

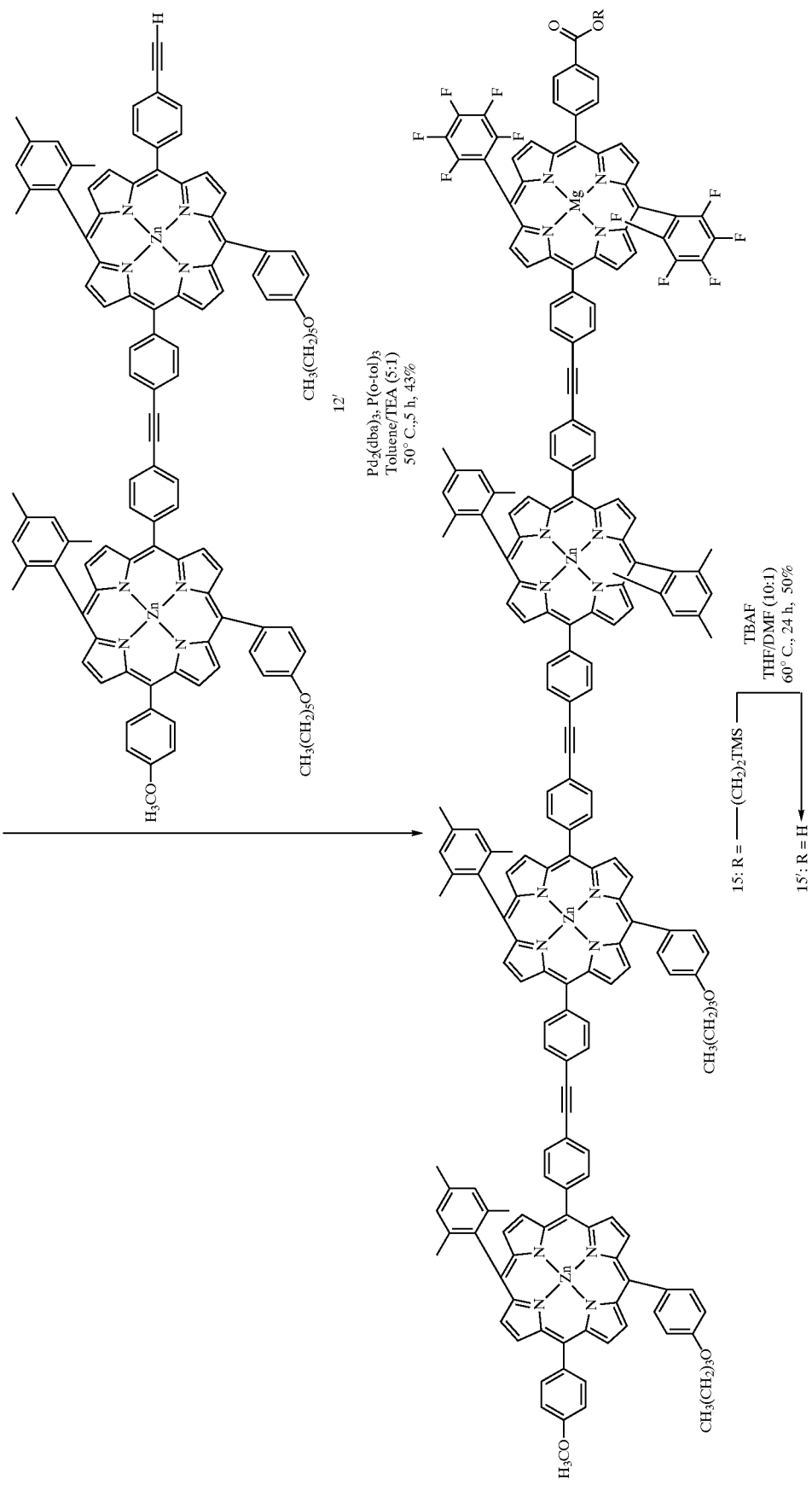

C. Pentad 19. The successive coupling procedures were employed in the convergent synthesis of a linear pentad. Dyad 16 was prepared by chemoselective Sonogashira coupling of Zn-6c' and Zn-6d in 60% yield (Scheme 18). Bromo-dyad 16 and ethynyl-dyad 12' were then reacted at 50° C. for 5 h to furnish tetrad 17 in 31% yield. Tetrad 17 proved to have poor solubility. Tetrad 17 was almost totally insoluble in $CH_2Cl_2$ and $CHCl_3$, only slightly soluble in toluene and moderately soluble in THF. The highest solubility was obtained with mixtures of toluene and THF. Second, slight heating was sometimes necessary to achieve full dissolution of 17, indicative of aggregate formation. Nonetheless, only one preparative SEC was necessary to achieve good separation between HMWM, product and dimeric starting materials. Characterization by $^1$H NMR spectroscopy proved difficult, but TLC analysis showed only one spot under a variety of solvent systems, analytical SEC showed a single sharp peak, and LD-MS analysis showed a strong molecule ion peak (m/z=3356). Because of the limited solubility, deprotection of 17 and subsequent coupling with Mg-6e was not attempted and another route to prepare pentad 19 was undertaken.

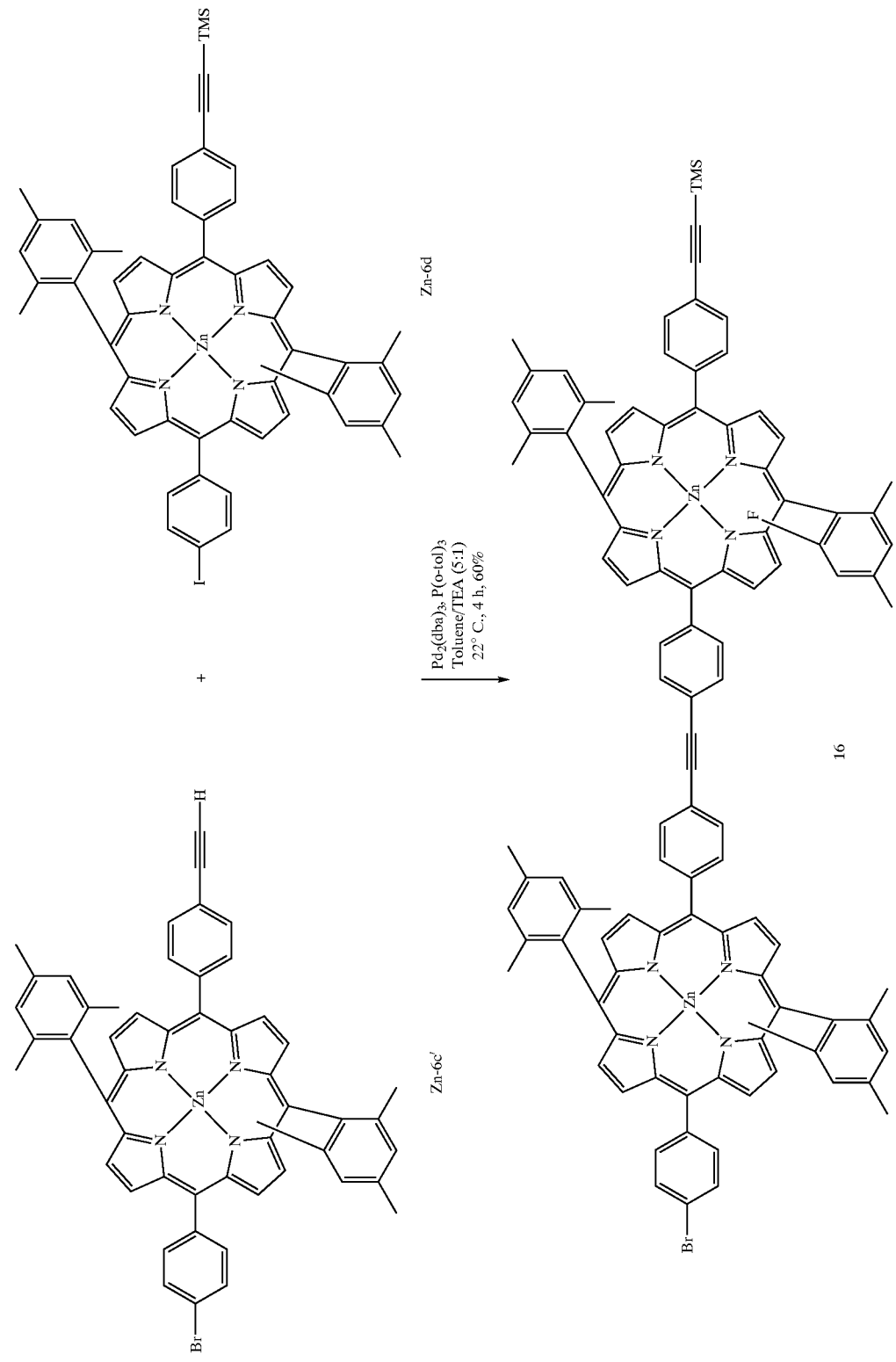

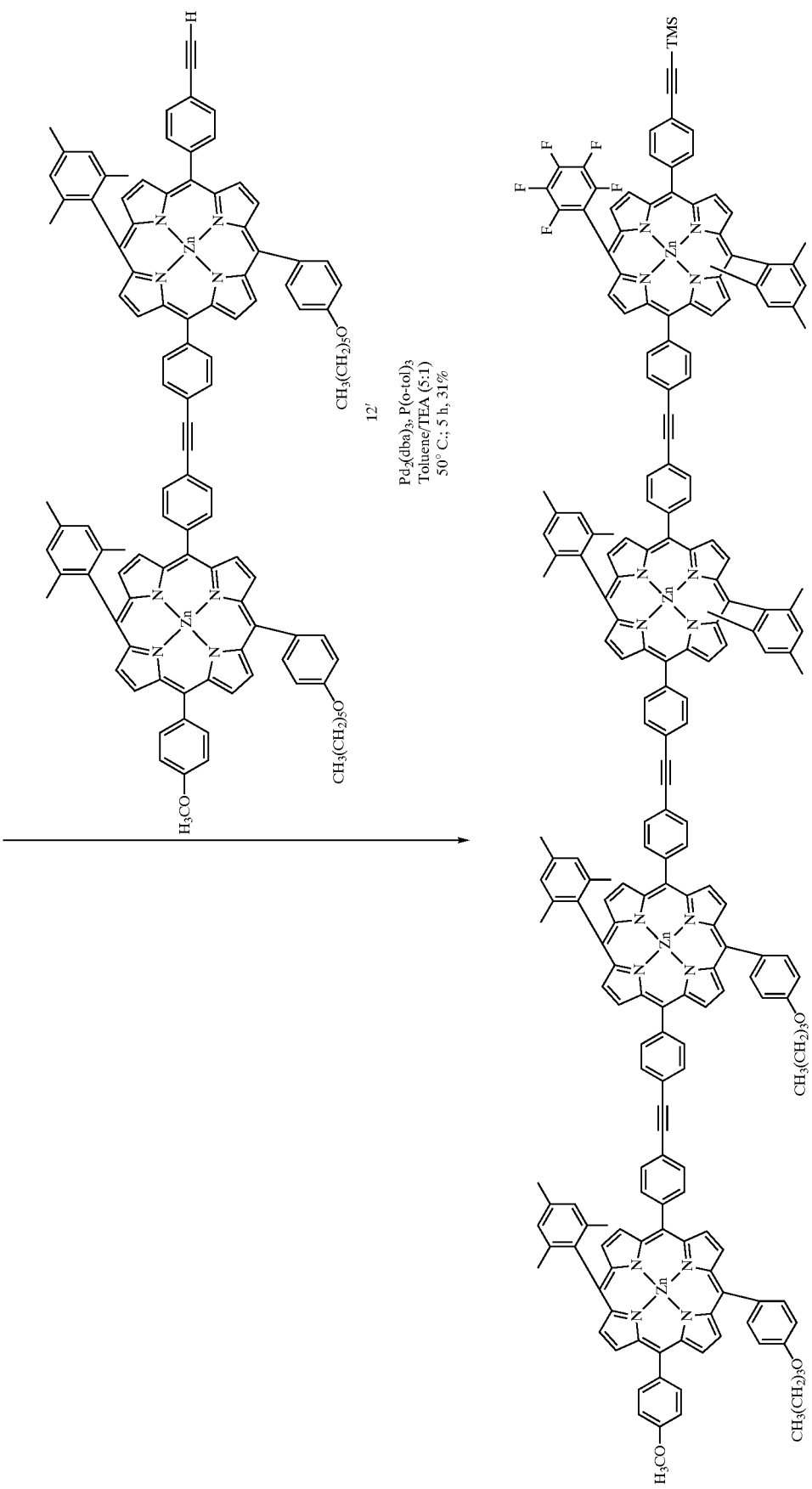

The outline for the synthesis of pentad 19 via a 3+2 route is shown in Scheme 19. Bromo/ethynyl-porphyrin dyad 16' was prepared in 84% yield by treatment of 16 with TBAF in THF at room temperature for 1 h. Dyad 16' was then reacted with Mg-6e at room temperature to achieve selective iodo+ethyne coupling yielding triad 18 in 51% yield after reaction for 4.5 h. Triad 18 and dyad 12' were then reacted in the presence of $Pd_2(dba)_3$ and $P(o\text{-tol})_3$ at 55° C. SEC analysis of an aliquot removed from the crude reaction mixture after 70 min showed 25% conversion to pentad. After another addition of catalyst and reaction for an additional 1.5 h (3 h total reaction time), analytical SEC revealed 38% conversion to pentad. The reaction mixture was no longer homogeneous at this point and the reaction was stopped after 5 h. Due to the poor solubility and complicated SEC trace (see Experimental Section), large material losses occurred upon workup and only a small amount of material (pure by SEC) was obtained.

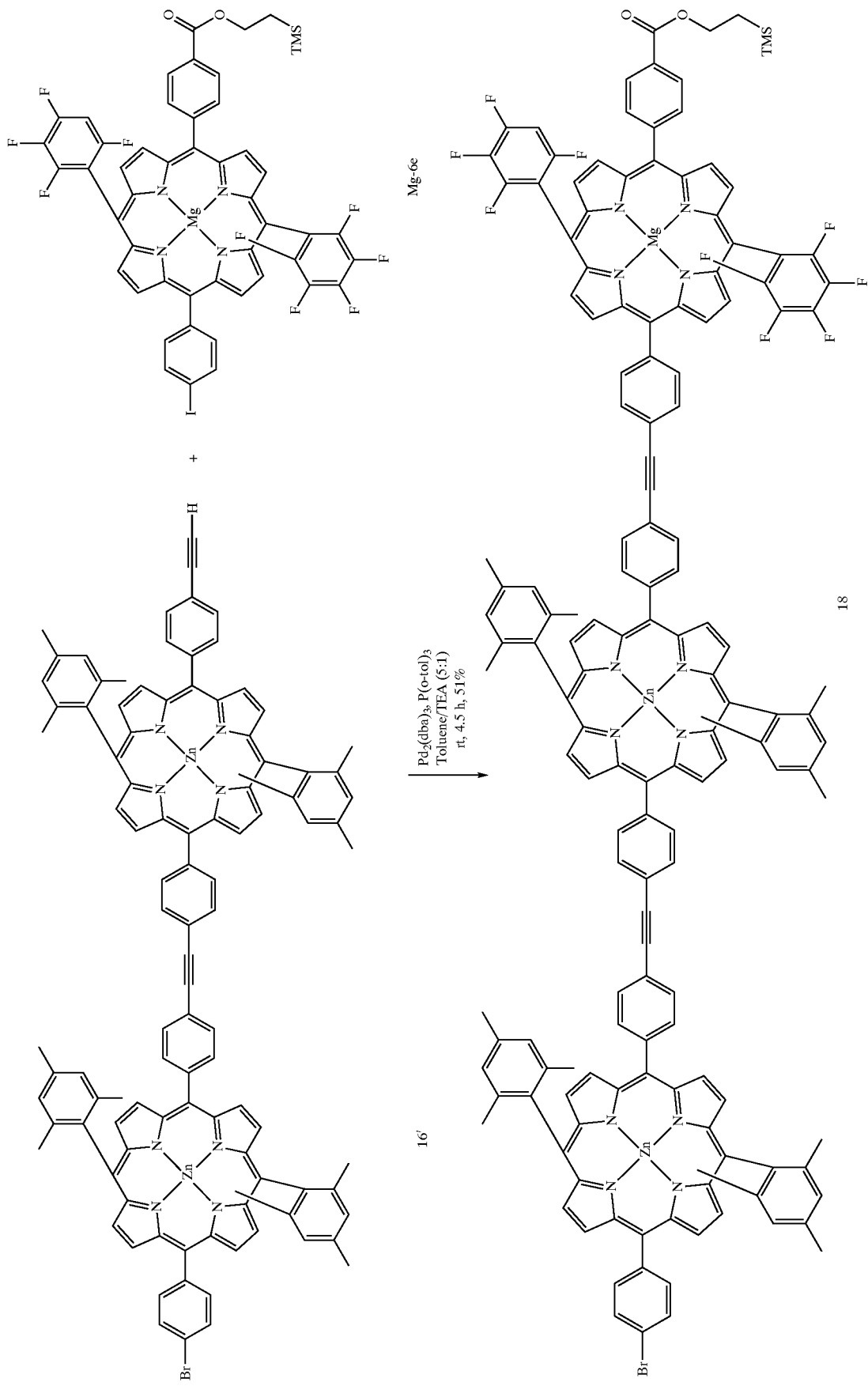

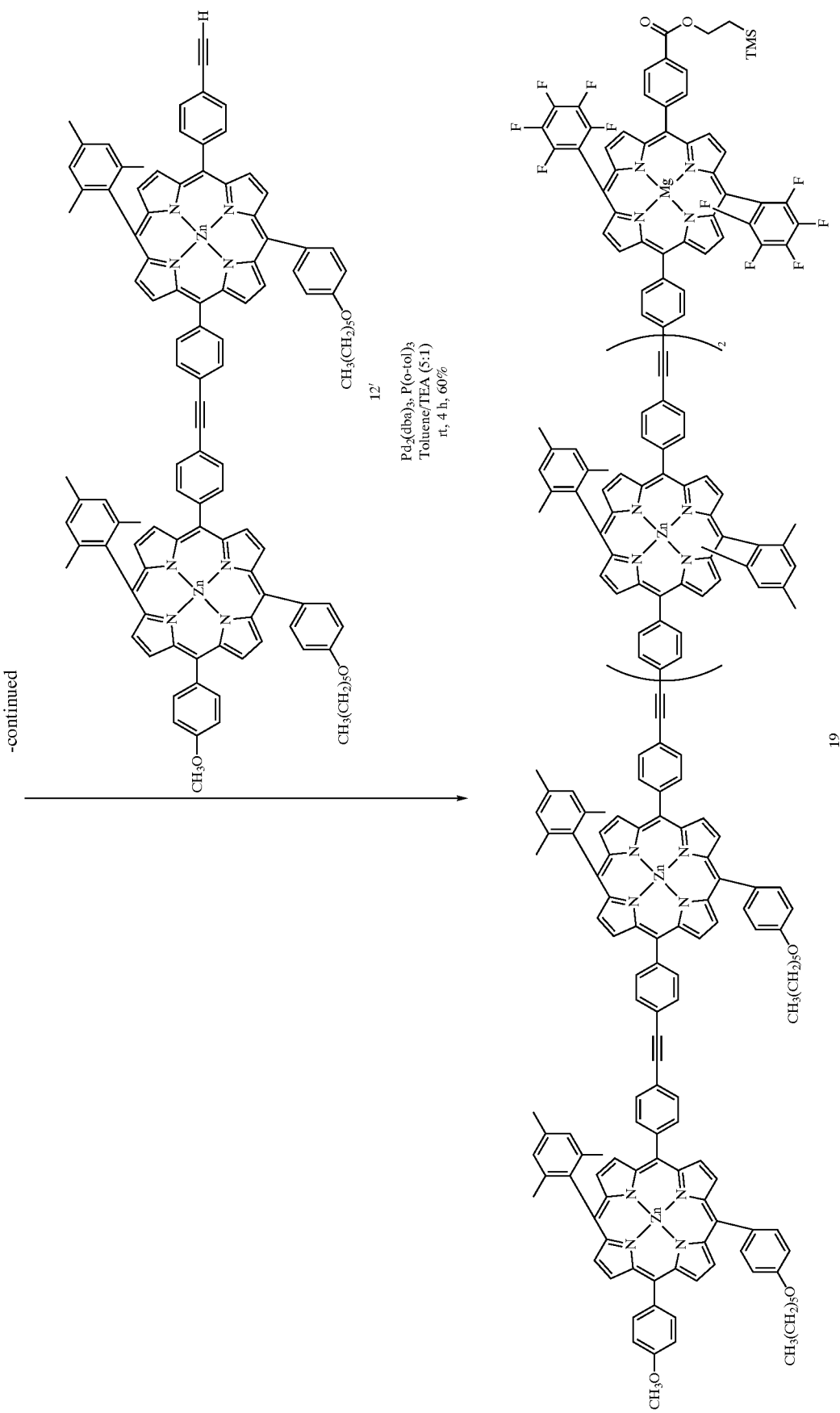

D. Benchmark compounds. The assessment of the photodynamic properties of the triad and tetrad requires suitable benchmark compounds for comparison purposes. A dyad which represents the carboxy terminus of the triad and tetrad was prepared as shown in Scheme 20. The Pd-mediated coupling of ethynyl porphyrin Zn-6i' and the iodo/ester porphyrin Mg-6f afforded the requisite ZnMg dyad 20. Several porphyrin monomers employed in the synthesis of the arrays proved to be suitable models for analogous components of the arrays. A trans-diethynyl zinc porphyrin (Zn-6j) was used as a model for the analogous Zn porphyrin in the tetrad. These porphyrins are displayed in Chart 1.

Chart 1

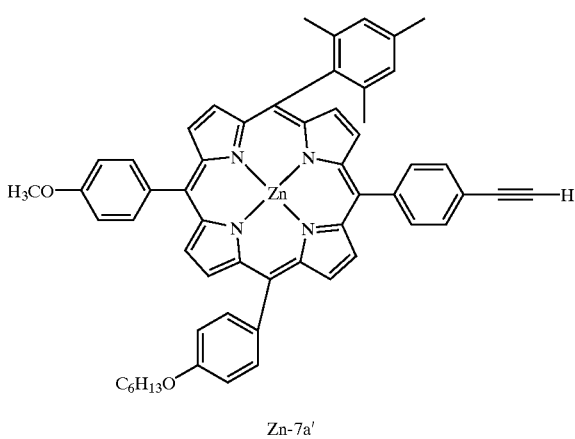

Zn-7a'

Scheme 20

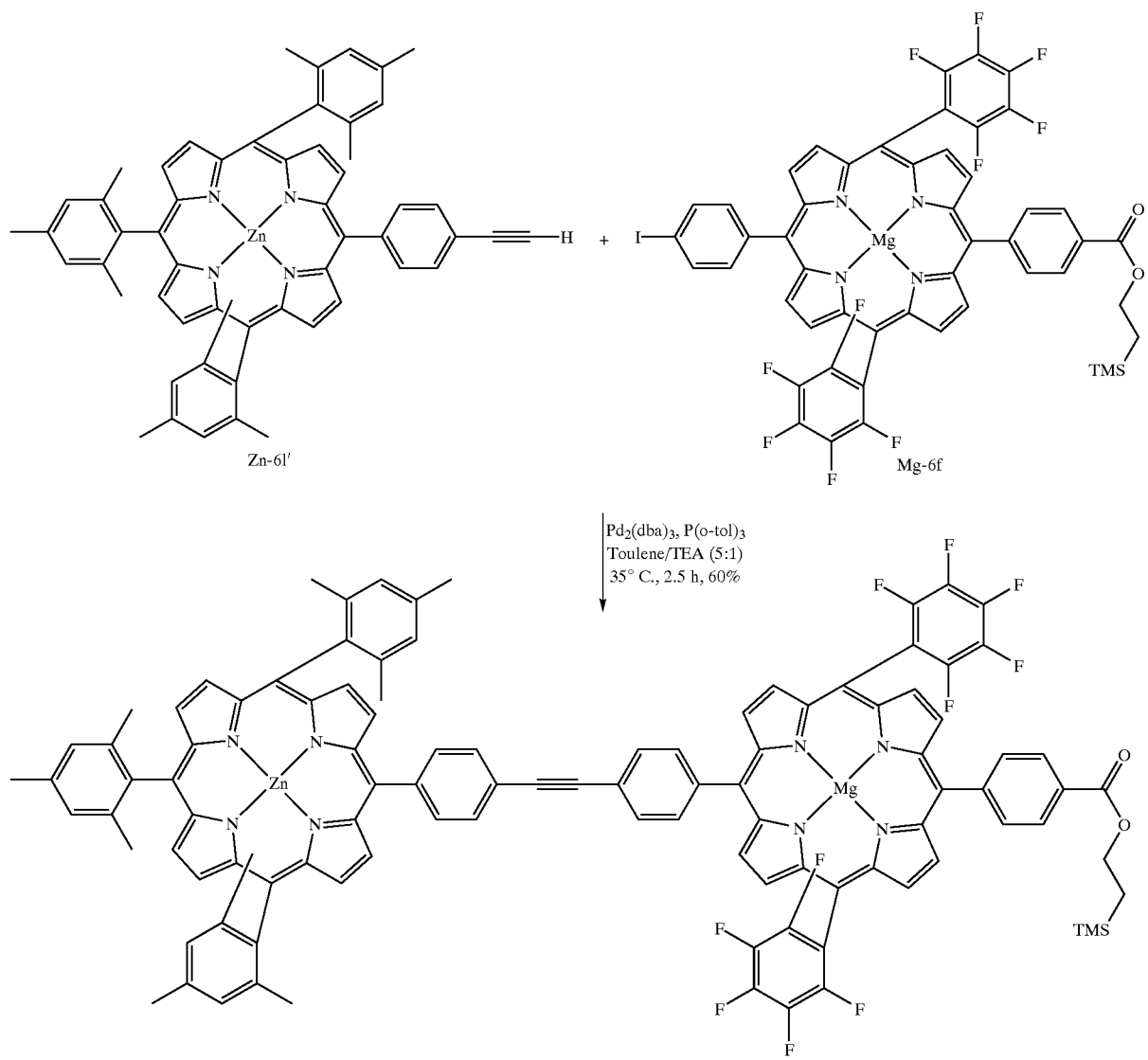

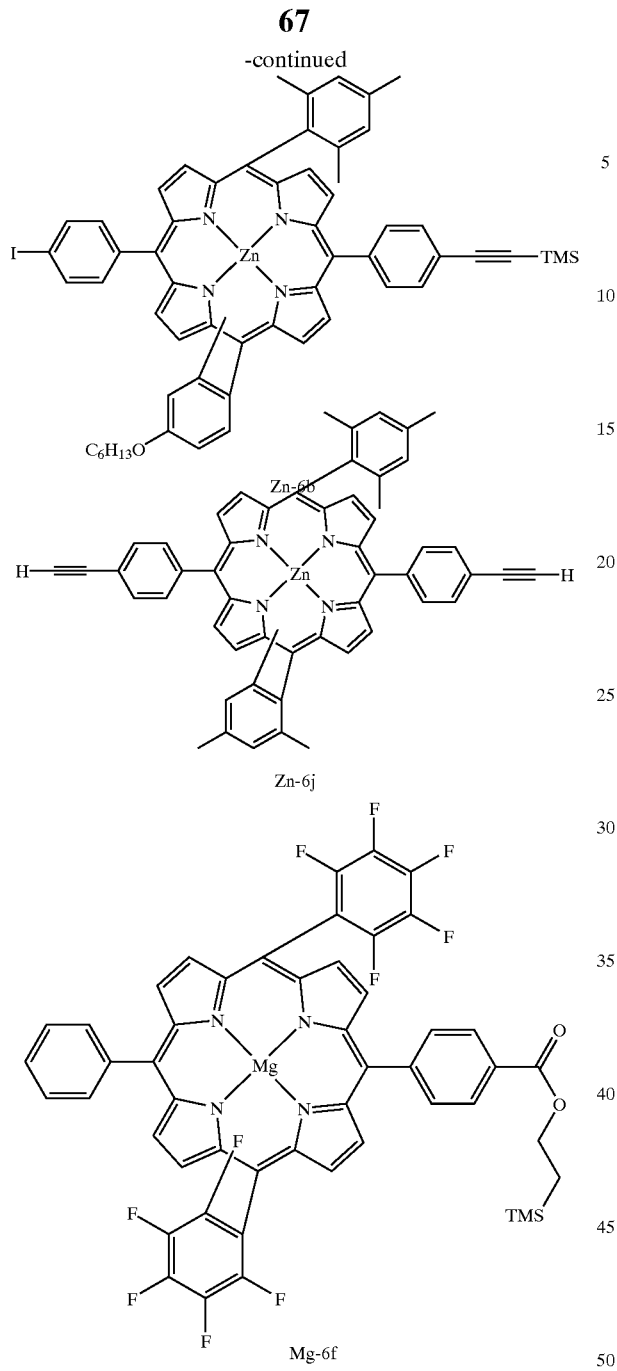

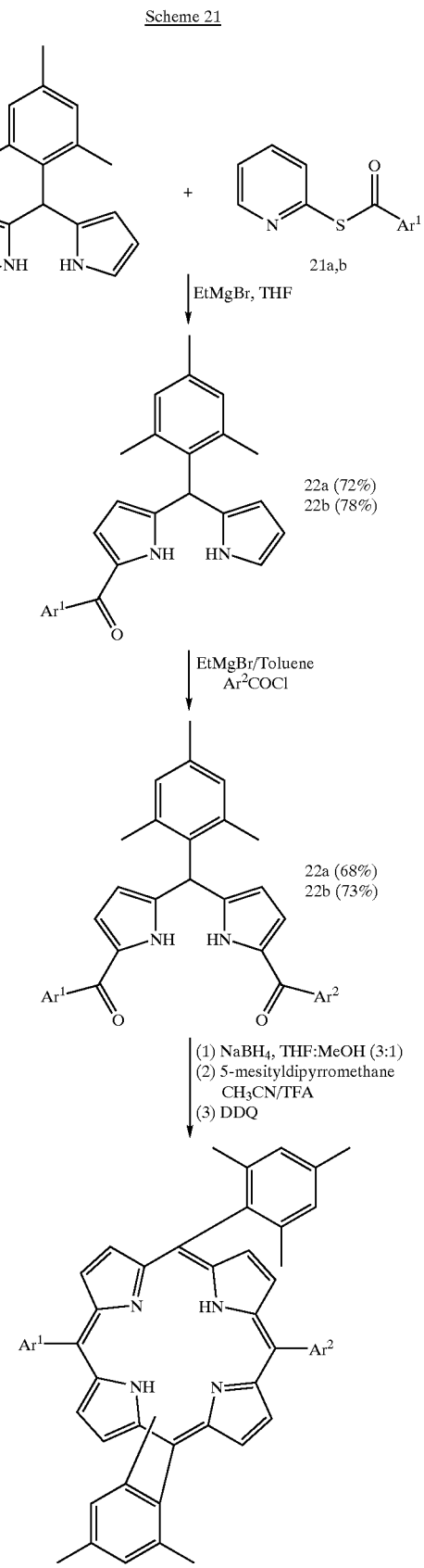

Scheme 21 rins were prepared with only minimal chromatography by this rational route.

E. Cyclic hexamer. Cyclic hexamers provide a useful architecture for fundamental studies of light harvesting (Li, J. et al. *J. Am. Chem. Soc.* 1999, 121, 8927–8940). The reaction of 5-mesityldipyrromethane with EtMgBr followed by a pyridyl-benzothioate (21a,b) gave the corresponding monoacyldipyrromethane 22a,b in good yield (Scheme 21). The second acyl group was introduced by reaction of a monoacyldipyrromethane (22a,b) with an iodobenzoyl chloride, affording the corresponding diacyldipyrromethane 23a,b. Treatment of a diacyldipyrromethane with NaBH$_4$ gives the corresponding dipyrromethane-dicarbinol (Rao, P. D. et al. *J. Org. Chem.* 2000, 65, 7323–7344). Condensation of 23a-dicarbinol and 5-mesityldipyrromethane under non-scrambling conditions (30 mM TFA in CH$_3$CN at room temperature) followed by oxidation with DDQ gave the single porphyrin product 24a. Metalation with zinc acetate gave Zn-24a. The analogous diacyldipyrromethane 23b was treated in the same manner, affording porphyrin 24b without scrambling. Sizable quantities (0.5–0.7 g) of pure porphy-

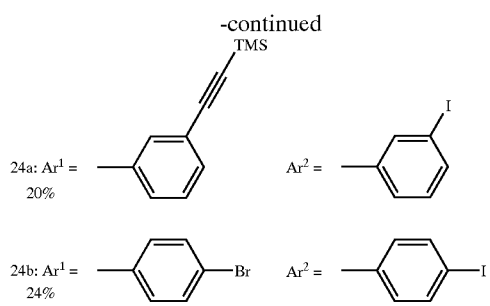

24a: Ar¹ = (3-ethynylphenyl, TMS), Ar² = (3-iodophenyl)
20%

24b: Ar¹ = (4-bromophenyl), Ar² = (4-iodophenyl)
24%

This route requires the preparation of two trimer precursors, a diethynyl trimer Zn₃-m/m-CCH and a dibromo trimer ZnFbZn-p/p-Br. The Sonogashira coupling of a p/p-diethynyl Fb porphyrin (25) with two equivalents of m/m-iodo/TMS-ethynyl Zn porphyrin Zn-24a was performed under the standard conditions for joining porphyrins (Scheme 22). The distribution of products observed by analytical SEC was typical, consisting of desired trimer, mono-coupled byproduct (dimer) and high molecular weight material (HMWM). Purification by one silica column, one preparative SEC column, and one silica column afforded the triad ZnFbZn-m/m-CCTMS in 47% yield. Deprotection of the TMS-ethynyl groups using TBAF (Wagner, R. W. et al. *J. Am. Chem. Soc.* 1996, 118, 11166–11180) gave the diethynyl triad ZnFbZn-m/m-CCH in 90% yield. Metalation with zinc acetate gave the all-zinc containing triad Zn₃-m/m-CCH in 91% yield.

The Sonogashira coupling of two molar equivalents of bromo/iodo porphyrin Zn-24b with diethynyl porphyrin 26 was performed at room temperature (Scheme 23). SEC analysis of an aliquot removed after 2.5 h showed the presence of 7% HMWM, 58% trimer, 7% dimer, and 28% monomers (uncorrected data). No additional catalyst was added for this reaction. Chromatographic workup (silica, SEC, silica) afforded the pure triad ZnFbZn-p/p-Br in 35% yield. This approach affords good selectivity for the iodo+ethyne reaction in the presence of a bromo group.

Scheme 22

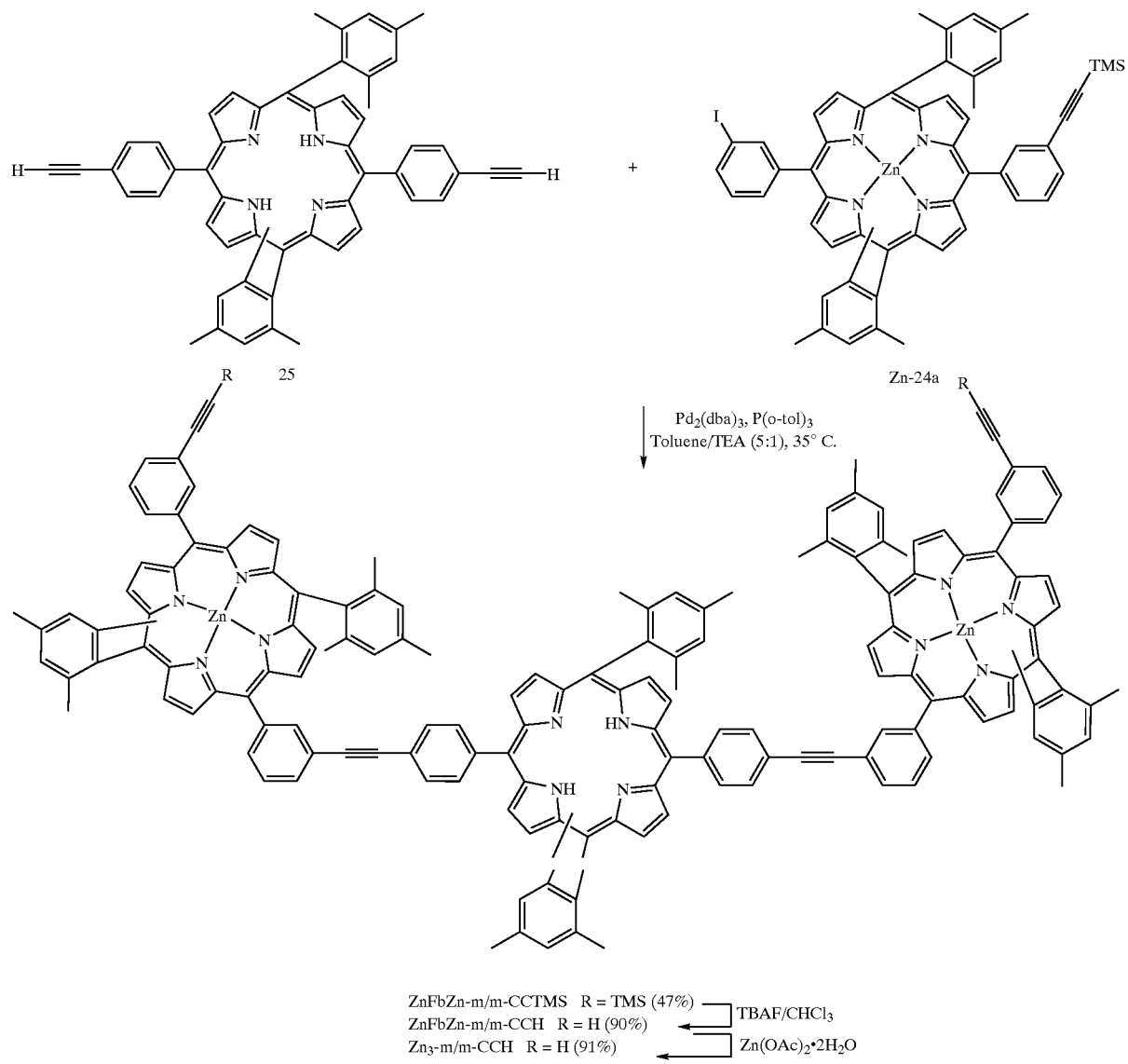

ZnFbZn-m/m-CCTMS R = TMS (47%) — TBAF/CHCl₃
ZnFbZn-m/m-CCH R = H (90%)
Zn₃-m/m-CCH R = H (91%) — Zn(OAc)₂·2H₂O

Scheme 23

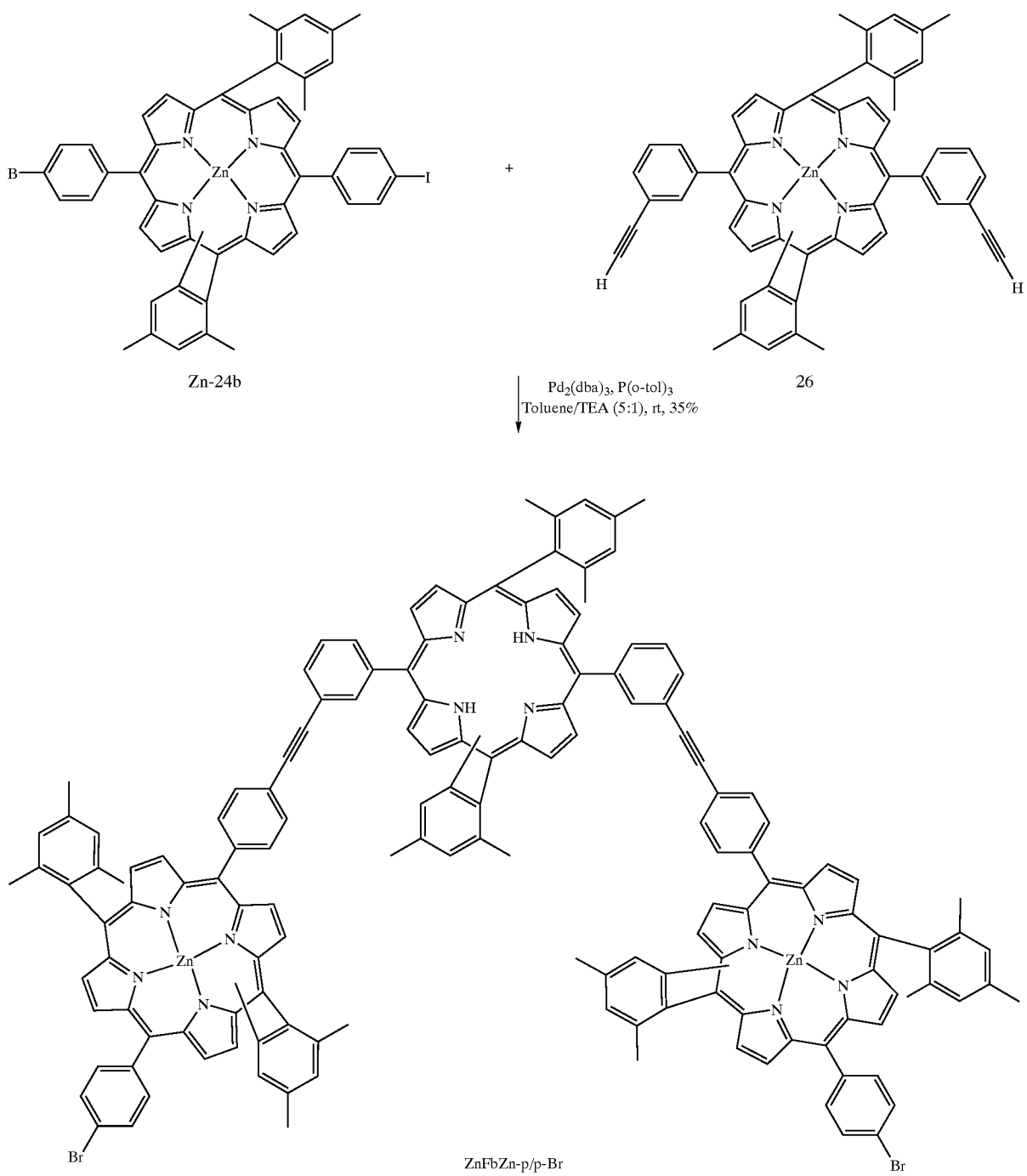

The 3+3 reaction of ZnFbZn-p/p-Br and Zn₃-m/m-CCH (Scheme 24) was carried out using the conditions for the bromo+ethyne coupling reaction, which are essentially identical to those of the iodo+ethyne reaction but with reaction at 80° C. Purification of this mixture required an SEC column (THF) to remove the un-dissolved Pd species and some of the HMWM, three preparative SEC columns to remove the remaining HMWM which chromatographed closely with the desired cyclic hexamer, and a final silica column chromatography. Some insoluble materials remained on top of the first short SEC column, which upon dissolution in pyridine and analysis by SEC were found to consist mostly of HMWM. The desired product cyclo-Zn₅FbU was obtained in 13.6% yield. This is the highest yield obtained to date for the formation of this type of cyclic hexamer. Thus, the use of selective, successive coupling reactions (iodo+ethyne, then bromo+ethyne) enabled the synthesis to be carried out in a convergent manner.

Scheme 24
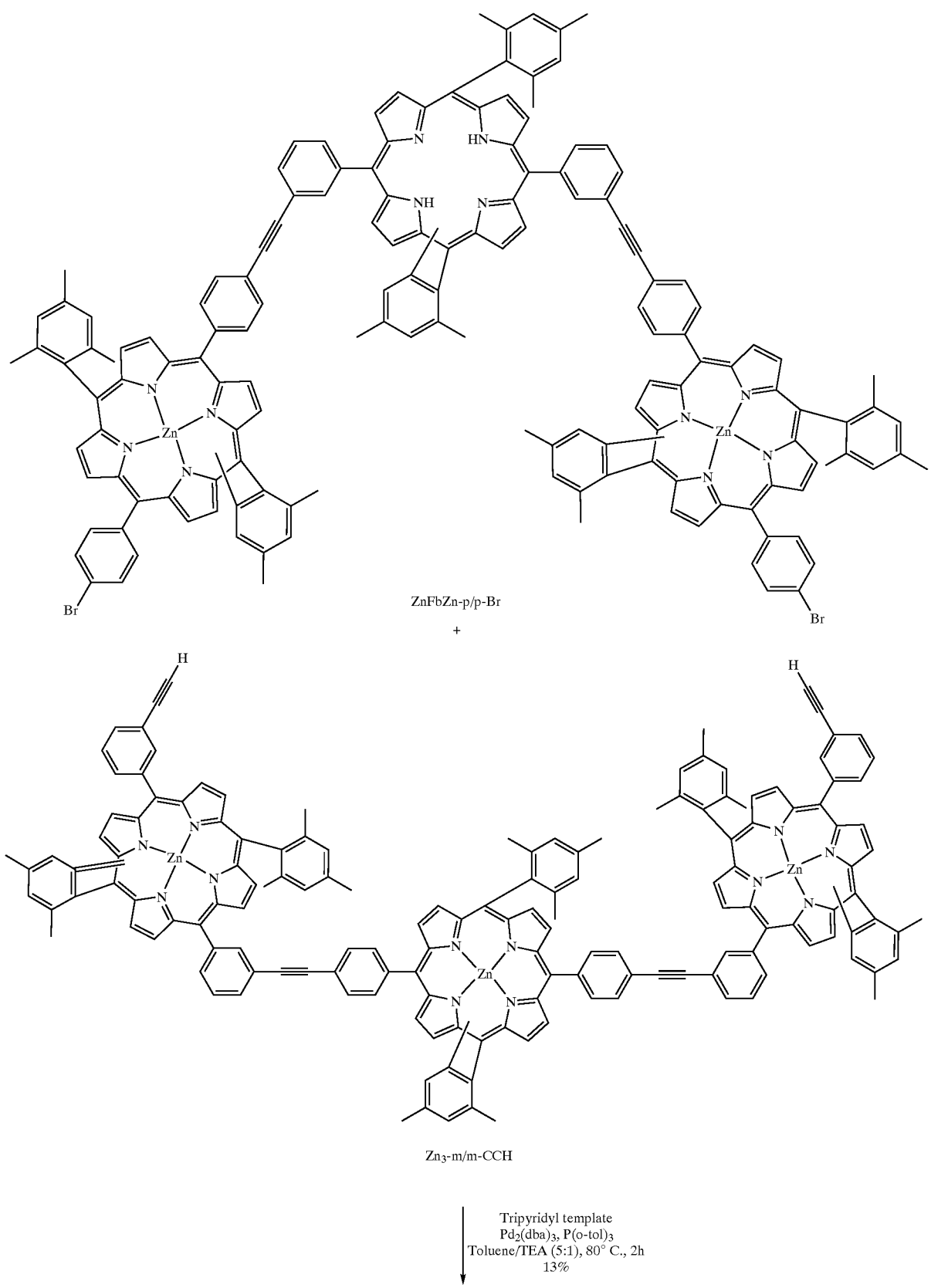

-continued

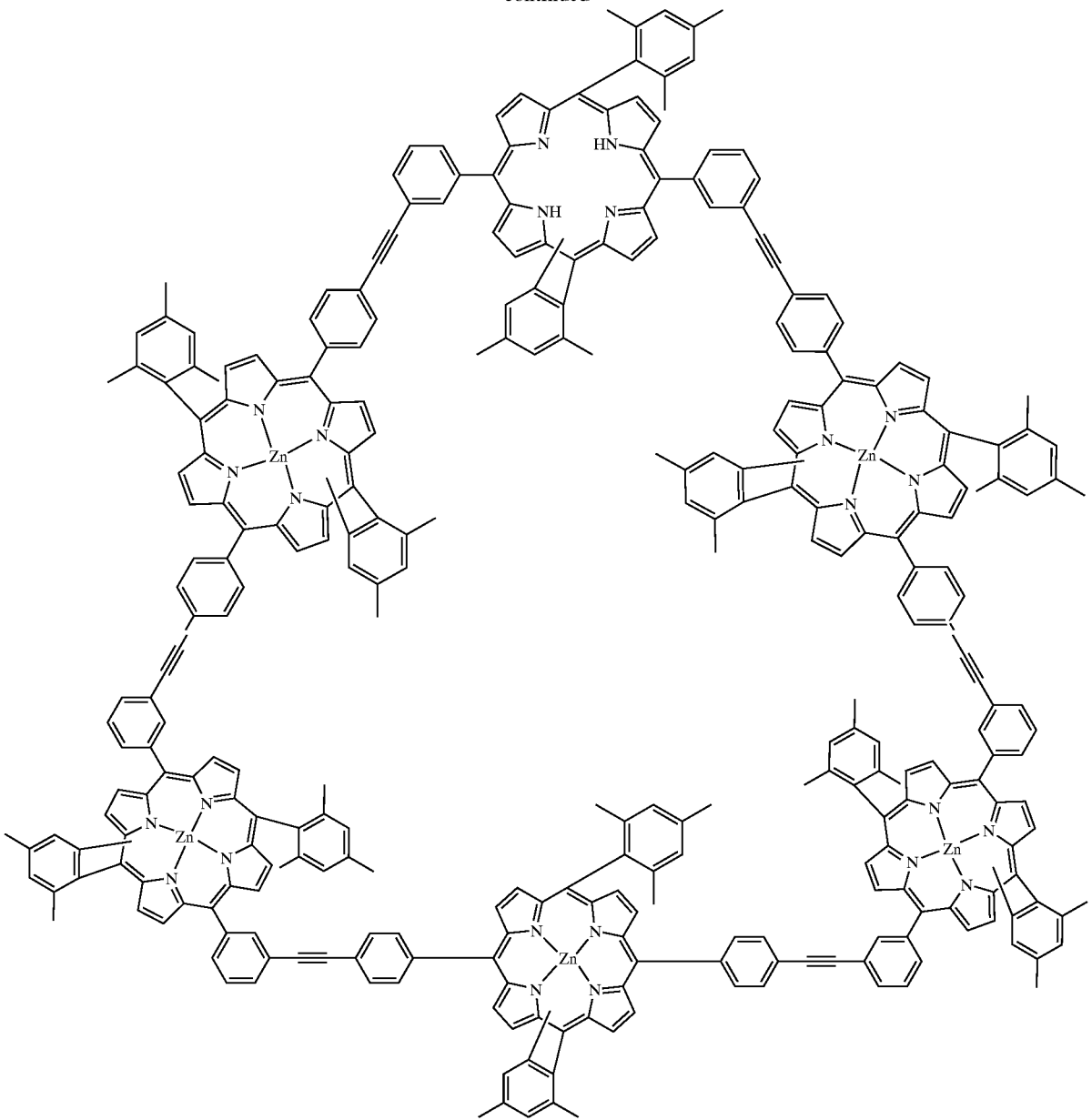

Cyclo-Zn₅FbU

Example 1

5-[4-(Hexyloxy)phenyl]dipyrromethane (2g)

Following a known general procedure (Littler, B. J. et al., *J. Org. Chem.* 1999, 64, 1391–1396), a mixture of pyrrole (65 mL, 1.0 mol) and 4-(hexyloxy)benzaldehyde (7.94 g, 38.5 mmol) was treated with TFA (0.296 mL, 3.84 mmol), and the mixture was stirred for 5 min. A solution of 0.1 M aq NaOH (70 mL) and ethyl acetate (70 mL) were added, and the layers were separated. The aqueous layer was washed with additional ethyl acetate (50 mL). The organic layers were collected, dried ($Na_2SO_4$), and concentrated. Column chromatography (silica, $CH_2Cl_2$) afforded a yellow, viscous oil which was recrystallized from ethanol/$H_2O$ (10:1), affording an amorphous, pale yellow solid (4.88 g, 40%): mp 58–60° C.; $^1$H NMR δ 0.91 (t, 3H), 1.33 (m, 4H), 1.46 (m, 2H), 1.77 (m, 2H), 3.94 (t, 2H), 5.42 (s, 1H), 5.92 (m, 2H), 6.15 (m, 2H), 6.69 (m, 2H), 6.85 (d, J=8.7 Hz, 2H), 7.11 (d, J=8.7 Hz, 2H), 7.91 (brs, 2H); $^{13}$C NMR δ 14.0, 22.6, 25.7, 29.2, 31.5, 43.0, 68.0, 107.0, 108.3, 114.5, 117.0, 129.3, 132.9, 133.9, 158.0; HRMS (FAB) obsd 322.2053, calcd 322.2045; Anal. Calcd for $C_{21}H_{26}N_2O$: C, 78.22; H, 8.13; N, 8.69. Found: C, 77.32; H, 8.08; N, 8.62.

Example 2

1-(4-Bromobenzoyl)-5-mesityldipyrromethane (4b)

Following a general procedure (Rao, P. D. et al., *J. Org. Chem.* 2000, 65, 1084–1092.), a solution of 2a (1.85 g, 7.00 mmol) in dry THF (10 mL) was treated with EtMgBr (15.4 mL, 15.4 mmol, 1.0 M in THF) for 10 min at room temperature under argon. The mixture was cooled to −78° C. and S-2-pyridyl 4-bromobenzothioate (2.06 g, 7.00 mmol) was added. The mixture was stirred at −78° C. for 10 min and then warmed to room temperature and stirred for 40 min. Standard workup and chromatography (silica, $CH_2Cl_2$) afforded a yellow foam-like solid (2.46 g, 78%): mp 120–122° C.; $^1H$ NMR δ 2.09 (s, 6H), 2.29 (s, 3H), 5.95 (s, 1H), 6.12–6.15 (m, 2H), 6.20–6.23 (m, 1H), 6.68–6.69 (m, 1H), 6.78–6.80 (m, 1H), 7.00 (s, 2H), 7.60 (d, J=8.1 Hz, 2H), 7.72 (d, J=8.1 Hz, 2H), 7.84 (brs, 1H), 9.24 (brs, 1H); $^{13}C$ NMR δ 20.7 38.6, 107.2, 108.9, 110.2, 116.9, 120.5, 126.3, 128.9, 129.5, 130.3, 130.5, 131.5, 132.9, 137.1, 137.2, 137.4, 141.3, 182.7; Anal Calcd for $C_{25}H_{23}BrN_2O$: C, 67.12; H, 5.18; N, 6.26. Found: C, 67.11; H, 5.23; N, 6.23.

Example 3

1-(4-Methoxybenzoyl)-5-mesityl-9[4[2-(trimethylsilyl)ethynyl]benzoyl]dipyrromethane (5a)

Following a general procedure (Rao, P. D. et al., *J. Org. Chem.* 2000, 65, 7323–7344), a solution of 4a (2.85 g, 6.13 mmol) in dry toluene (25 mL) was treated with EtMgBr (12.2 mL, 12.2 mmol, 1 M in THF) at room temperature under argon. After stirring for 10 min, 4-anisoyl chloride (1.04 g, 6.10 mmol) was added. After 10 min, the same process was repeated once. After stirring for 10 min, the mixture was treated with additional EtMgBr (6.1 mL, 6.1 mmol, 1 M in THF) followed by 4-anisoyl chloride (0.52 g, 3.1 mmol). The mixture was stirred at room temperature for 30 min; standard workup and chromatography [silica, $CH_2Cl_2$, followed by $CH_2Cl_2$/ethyl acetate (9:1)]; (silica, ethyl acetate) afforded a red solid (2.59 g, 71%): mp 136–138° C.; $^1H$ NMR δ 0.26 (s, 9H), 2.19 (s, 6H), 2.31 (s, 3H), 3.85 (s, 3H), 6.03 (m, 2H), 6.11 (s, 1H), 6.67 (m, 2H), 6.90 (d, J=8.1 Hz, 2H), 6.92 (s, 2H), 7.49 (d, J=8.7 Hz, 2H), 7.70 (d, J=8.1 Hz, 2H), 7.78 (d, J=8.7 Hz, 2H), 10.46 (brs, 2H); $^{13}C$ NMR δ −0.2, 20.9, 39.2, 55.3, 96.9, 104.3, 110.3, 110.5, 113.2, 120.2, 121.1, 126.1, 129.2, 130.1, 130.3, 130.4, 130.9, 131.4, 133.2, 136.9, 137.5, 137.9, 139.1, 140.7, 162.3, 182.6; Anal. Calcd for $C_{38}H_{38}N_2O_3Si$: C, 76.22; H, 6.40; N, 4.68. Found: C, 76.06; H, 6.53; N, 4.62.

Example 4

1-(4-Bromobenzoyl)-5-mesityl-9-[4-[2-(trimethylsilyl)ethynyl]benzoyl]dipyrromethane (5b)

Following a general procedure (Rao, P. D. et al., *J. Org. Chem.* 2000, 65, 7323–7344), reaction of 4a (2.79 g, 6.00 mmol) and 4-bromobenzoyl chloride (1.32 g, 6.00 mmol) followed by column chromatography (silica, $CH_2Cl_2$) and recrystallization from $CH_2Cl_2$/methanol afforded a yellow solid (2.66 g, 68%): mp 144–146° C.; $^1H$ NMR δ 0.26 (s, 9H), 2.19 (s, 6H), 2.32 (s, 3H), 6.06 (m, 2H), 6.11 (s, 1H), 6.68 (m, 2H), 6.93 (s, 2H), 7.49 (d, J=7.8 Hz, 2H), 7.55 (d, J=8.1 Hz, 2H), 7.63 (d, J=8.1 Hz, 2H), 7.69 (d, J=7.8 Hz, 2H), 10.43 (brs, 2H); $^{13}C$ NMR δ −0.2, 20.8, 39.2, 97.1, 104.3, 110.7, 121.2, 126.3, 129.2, 130.0, 130.3, 130.5, 130.8, 131.2, 131.4, 133.0, 136.9, 137.0, 137.4, 137.7, 140.3, 140.6, 182.4, 182.7. Anal. Calcd for $C_{37}H_{35}BrN_2O_2Si$: C, 68.61; H, 5.45; N, 4.33. Found: C, 68.88; H, 5.26; N, 4.08.

Example 5

1,9-bis(Pentafluorobenzoyl)-5-(4-iodophenyl)dipyrromethane (5d)

Following a general procedure (Rao, P. D. et al., *J. Org. Chem.* 2000, 65, 7323–7344), to a solution of 2b (2.00 g, 5.74 mmol) in dry toluene (95 mL) was added EtMgBr (11.5 mL, 11.5 mmol, 1 M in THF) at room temperature under argon. After stirring for 10 min, a solution of pentafluorobenzoyl chloride (1.34 g, 5.81 mmol) in toluene (6 mL) was added dropwise by addition funnel. After 10 min, the same process was repeated once. After stirring for 10 min, the mixture was treated with additional EtMgBr (5.7 mL, 5,7 mmol, 1 M in THF) followed by a solution of pentafluorobenzoyl chloride (0.66 g, 2.9 mmol) in toluene (3 mL). After stirring the contents for 30 min, saturated aqueous $NH_4Cl$ and ethyl acetate were added. The organic layer was separated, washed with brine, dried ($Na_2SO_4$), and concentrated. The mono and diacyl components were separated by column chromatography [silica, $CH_2Cl_2$/ethyl acetate (95:5)]. The crude diacyl dipyrromethane was dissolved in $CH_2Cl_2$ and hexanes were slowly added to precipitate the product. Filtration and washing with hexanes afforded a fluffy white powder (1.70 g, 40%): mp 138–140° C.; $^1H$ NMR δ 5.60 (s, 1H), 6.12 (m, 2H), 6.67 (m, 2H), 6.97 (d, J=8.1 Hz, 2H), 7.71 (d, J=8.1 Hz, 2H), 9.80 (brs, 2H); $^{13}C$ NMR δ 44.5, 94.3, 112.9, 114.3, 123.6, 130.9, 132.2, 138.8, 139.9, 140.0, 142.9, 143.2, 146.3, 173.1; Anal. Calcd: C, 47.31; H, 1.51; N, 3.80. Found: C, 47.49; H, 1.73; N, 3.64.

Example 6

5-Mesityl-10-[4-[2-(trimethylsilyl)ethynyl]phenyl]-15-[4-(hexyloxy)phenyl]-20-(4-methoxyphenyl)porphyrin (6a)

Following a general procedure (Rao, P. D. et al., *J. Org. Chem.* 2000, 65, 7323–7344), a solution of diacyl dipyrromethane 5a (2.00 g, 3.34 mmol) in dry THF/methanol (10:1, 132 mL) at room temperature was treated with $NaBH_4$ (2.53 g, 66.8 mmol) in small portions over a 15 min period. The reduction was judged complete after 1 h by TLC [alumina, $CH_2Cl_2$/ethyl acetate (3:2)]. The solution was poured into a stirred mixture of $CH_2Cl_2$ (300 mL) and saturated aqueous $NH_4Cl$ (150 mL) in a 1-L beaker. The organic phase was washed with water (2×150 mL), dried ($Na_2SO_4$), and placed in a 2-L round bottomed flask. The dipyrromethane-dicarbinol was recovered after rotary evaporation as a foam-like solid. To the dipyrromethane-dicarbinol was added dipyrromethane 2g (1.08 g, 3.34 mmol) and acetonitrile (1.34 L). The mixture was stirred for 5 min, then TFA (3.09 mL, 40.1 mmol) was added dropwise over 1 min. The reaction was monitored by absorption spectroscopy. After 4 min, DDQ (2.27 g, 10.0 mmol) was added and the mixture was stirred at room temperature for 1 h. Triethylamine (5.56 mL, 40.0 mmol) was added, and the mixture was filtered through a pad of alumina and eluted with $CH_2Cl_2$. The filtrate was concentrated by rotary evaporation. The resulting purple solid was passed through a short pad of silica ($CH_2Cl_2$ elution) to remove non-porphyrin products. The porphyrin-containing fractions were combined and concentrated to yield a purple solid. The solid was triturated with methanol, then filtered. The solid was dissolved in $CH_2Cl_2$, and the solvent was removed to yield a purple solid (662 mg, 22%): $^1H$ NMR δ −2.70 (brs, 2H), 0.38 (s, 9H), 0.99 (t, 3H), 1.53 (m, 4H), 1.63 (m, 2H), 1.84 (s, 6H), 1.99 (m, 2H), 2.63 (s, 3H), 4.10 (s, 3H), 4.25 (t, 2H), 7.26–7.29 (m, 6H), 7.87 (d, J=8.1 Hz, 2H), 8.09 (d, J=9.0 Hz, 2H), 8.13 (d, J=9.0 Hz, 2H), 8.17 (d, J=8.1 Hz, 2H), 8.7–8.9 (m, 8H); LD-MS obsd 881.6; HRMS (FAB) obsd 882.4367, calcd 882.4329 ($C_{59}H_{58}N_4O_2Si$); $\lambda_{abs}$ 423, 517, 553, 594, 651 nm.

Example 7

5-Mesityl-10-[4-[2-(trimethylsilyl)ethynyl]phenyl]-15-(4-hexyloxyphenyl)-20-(4-iodophenyl)porphyrin (6b)

Reduction of 5c (2.57 g, 3.70 mmol) followed by condensation with 2g (1.19 g, 3.70 mmol) for 3 min, oxidation with DDQ (2.52 g, 11.1 mmol), and standard workup furnished a purple solid (790 mg, 22%): $^1$H NMR δ −2.73 (brs, 2H), 0.38 (s, 9H), 1.00 (t, 3H), 1.47 (m, 4H), 1.65 (m, 2H), 1.84 (s, 6H), 1.99 (m, 2H), 2.64 (s, 3H), 4.26 (t, 2H), 7.29 (s, 4H), 7.87 (d, J=8.1 Hz, 2H), 7.95 (d, J=8.1 Hz, 2H), 8.09 (d, J=7.8 Hz, 4H), 8.17 (d, J=8.1 Hz, 2H), 8.7–8.9 (m, 8H); LD-MS obsd 979.8; HRMS (FAB) obsd 979.3278, calcd 979.3268 ($C_{58}H_{55}IN_4OSi$); $\lambda_{abs}$ 422, 516, 552, 594, 651 nm.

Example 8

5,15-Dimesityl-10-[4-[2-(trimethylsilyl)ethynyl]phenyl]-20-(4-bromophenyl)porphyrin (6c)

Reduction of 5b (1.40 g, 2.16 mmol), followed by condensation with 2a (0.57 g, 2.2 mmol) for 3 min, oxidation with DDQ (1.47 g, 6.47 mmol), and standard workup furnished a purple solid (484 mg, 26%): $^1$H NMR δ −2.68 (brs, 2H), 0.37 (s, 9H), 1.83 (s, 12H), 2.63 (s, 6H), 7.28 (s, 4H), 7.84–7.89 (m, 4H), 8.08 (d, J=8.1 Hz, 2H), 8.16 (d, J=8.1 Hz, 2H), 8.69–8.77 (m, 8H); LD-MS obsd 873.0; HRMS (FAB) obsd 872.2898, calcd, 872.2910 ($C_{55}H_{49}BrN_4Si$); $\lambda_{abs}$ 420, 515, 549, 592, 649 nm.

Example 9

5,15-Dimesityl-10-[4-[2-(trimethylsilyl)ethynyl]phenyl]-20-(4-iodophenyl)porphyrin (6d)

Reduction of 5c (2.30 g, 3.31 mmol), followed by condensation with 2a (0.87 g, 3.3 mmol) for 3 min, oxidation with DDQ (2.31 g, 9.93 mmol), and standard workup furnished a purple solid (0.66 g, 22%). The $^1$H NMR and LD-MS data were identical to samples prepared by a known mixed-aldehyde condensation.

Example 10

5,15-bis(Pentafluorophenyl)-10-(4-iodophenyl)-20-[4-[2-(trimethylsilyl)ethoxycarbonyl]phenyl]porphyrin (6e)

Reduction of 5d (2.21 g, 3.00 mmol) followed by condensation with 2f (1.10 g, 3.00 mmol) for 5 min, oxidation with DDQ (2.04 g, 9.00 mmol), and standard workup furnished a purple solid. A second column [silica, $CH_2Cl_2$/hexanes (1:1)] yielded a purple solid (562 mg, 18%): $^1$H NMR δ −2.89 (s, 2H), 0.18 (s, 9H), 1.30 (t, 2H), 4.62 (t, 2H), 7.95 (d, J=8.7 Hz, 2H), 8.13 (d, J=8.7 Hz, 2H), 8.30 (d, J=8.7 Hz, 2H), 8.46 (d, J=8.7 Hz, 2H), 8.8–9.0 (m, 8H); LD-MS obsd 1066.7; HRMS (FAB) obsd 1064.1105, calcd 1064.1101 ($C_{50}H_{31}F_{10}IN_4O_2Si$); $\lambda_{abs}$ 419, 512, 545, 589, 644 nm.

Example 11

5,15-bis(Pentafluorophenyl)-10-phenyl-20-[4-[2-(trimethylsilyl)ethoxycarbonyl]phenyl]porphyrin (6f)

Reduction of 5e (134 mg, 0.22 mmol) followed by condensation with 2f (80.6 mg, 0.22 mmol) for 7 min, oxidation with DDQ (150 mg, 0.66 mmol), and standard workup furnished a purple solid. A second column [silica, $CH_2Cl_2$/hexanes (1:1)] yielded a purple solid (39.2 mg, 19%): $^1$H NMR (400 MHz) δ −2.86 (s, 2H), 0.18 (s, 9H), 1.30 (t, 2H), 4.62 (t, 2H), 7.78–7.82 (m, 3H) 8.21 (d, J=8.0 Hz, 2H), 8.30 (d, J=8.4 Hz, 2H), 8.46 (d, J=7.2 Hz, 2H), 8.80–8.82 (m, 4H), 8.90 (d, J=4.4 Hz, 2H), 8.95 (d, J=4.4 Hz, 2H); LD-MS obsd 938.0; HRMS (FAB) obsd 1064.1105, calcd 1064.1101 ($C_{50}H_{32}F_{10}N_4O_2Si$); $\lambda_{abs}$ 418, 512, 544, 589, 643 nm.

Example 12

5,10,15-tri-p-Tolyl-20-(4-bromophenyl)porphyrin (6g)

Reduction of 5f (0.54 g, 1.2 mmol), followed by condensation with 2c (0.35 g, 1.2 mmol) for 3 min, oxidation with DDQ (0.79 g, 3.4 mmol), and standard workup furnished a purple solid (210 mg, 25%): $^1$H NMR δ −2.79 (s, 2H), 2.71 (brs, 9H), 7.56 (d, J=8.4 Hz, 6H), 7.89 (d, J=9.0 Hz, 2H), 8.08–8.11 (m, 8H), 8.80 (d, J=4.2 Hz, 2H), 8.87–8.90 (m, 6H); LD-MS obsd 734.3; HRMS (FAB) obsd 734.2083, calcd 734.2045 ($C_{47}H_{35}BrN_4$); $\lambda_{abs}$ 421, 516, 551, 593, 648 mm.

Example 13

Zinc-(II)-5-mesityl-10-[4-[2-(trimethylsilyl)ethynyl]phenyl]-15-[4-(hexyloxy)phenyl]-20-(4-methoxyphenyl)porphyrin (Zn-6a)

To a solution of 6a (147 mg, 0.166 mmol) in $CHCl_3$ (50 mL) was added a solution of $Zn(OAc)_2 \cdot 2H_2O$ (182 mg, 0.831 mmol) in methanol (6 mL). The reaction mixture was stirred at room temperature for 16 h. The reaction mixture was washed with water, dried ($Na_2SO_4$), and concentrated. Column chromatography (silica, $CH_2Cl_2$) afforded a purple solid (142 mg, 91%): $^1$H NMR δ 0.38 (s, 9H), 1.00 (t, 3H), 1.49 (m, 4H), 1.64 (m, 2H), 1.83 (s, 6H), 2.00 (m, 2H), 2.64 (s, 3H), 4.09 (s, 3H), 4.26 (t, 2H), 7.29 (s, 4H), 7.87 (d, J=8.1 Hz, 2H), 8.10 (d, J=8.7 Hz, 2H), 8.14 (d, J=8.7 Hz, 2H), 8.18 (d, J=8.1 Hz, 2H), 8.8–9.0 (m, 10H); LD-MS obsd 942.7; HRMS (FAB) obsd 944.3470, calcd 944.3464 ($C_{59}H_{56}N_4O_2SiZn$); $\lambda_{abs}$ 427, 552, 593 nm.

Example 14

Zinc(II)-5-mesityl-10-[4-[(2-trimethylsilyl)ethynyl]phenyl]-15-[4-(hexyloxy)phenyl]-20-(4-iodophenyl)porphyrin (Zn-6b)

A sample of 6b (160 mg, 0.163 mmol) was treated with $Zn(OAc)_2 \cdot 2H_2O$ (179 mg, 0.816 mmol) following the general procedure. Column chromatography (silica, $CH_2Cl_2$) afforded a purple solid (149 mg, 88%): $^1$H NMR δ 0.38 (s, 9H), 1.00 (t, 3H), 1.48 (m, 4H), 1.65 (m, 2H), 1.83 (s, 6H), 1.99 (m, 2H), 2.64 (s, 3H), 4.26 (t, 3H), 7.29 (s, 4H), 7.87 (d, J=8.1 Hz, 2H), 7.97 (d, J=8.7 Hz, 2H), 8.10 (m, 4H), 8.18 (d, J=8.1 Hz, 2H), 8.8–9.0 (m, 8H); LD-MS obsd 1040.7; HRMS (FAB) obsd 1040.2318, calcd 1040.2325 ($C_{58}H_{53}IN_4OSiZn$); $\lambda_{abs}$ 427, 552, 594 nm.

Example 15

Zinc-(II)-5,15-Dimesityl-10-[4-[2-(trimethylsilyl)ethynyl]phenyl]-20-(4-bromophenyl)porphyrin (Zn-6c)

A sample of 6c (262 mg, 300 μmol) was treated with $Zn(OAc)_2 \cdot 2H_2O$ (329 mg, 1.50 mmol) following the general procedure. Column chromatography [silica, $CHCl_3$/hexanes (7:3)] afforded a purple solid (265 mg, 94%). $^1$H NMR δ 0.37 (s, 9H), 1.82 (s, 12H), 2.63 (s, 6H), 7.28 (s, 4H), 7.84–7.89 (m, 4H), 8.10 (d, J=8.1 Hz, 2H), 8.18 (d, J=8.7 Hz, 2H), 8.77–8.79 (m, 4H), 8.84–8.86 (m, 4H); LD-MS obsd 936.5; HRMS (FAB) obsd 934.2055, calcd 934.2045 ($C_{55}H_{47}BrN_4SiZn$); $\lambda_{abs}$ 419, 550, 590 nm.

Example 16

Zinc-(II)-5,15-Dimesityl-10-[4-[2-(trimethylsilyl) ethynyl]phenyl]-20-(4-iodophenyl)porphyrin (Zn-6d)

A sample of 6d (0.38 g, 0.41 mmol) was treated with $Zn(OAc)_2 \cdot 2H_2O$ (0.45 g, 2.1 mmol) following the general procedure. Purification was achieved by suspension in methanol, followed by filtration to afford a purple solid (0.36 g, 90%): $^1$H NMR δ 0.37 (s, 9H), 1.82 (s, 12H), 2.63 (s, 6H), 7.28 (s, 4H), 7.86 (d, J=8.1 Hz, 2H), 7.97 (d, J=8.1 Hz, 2H), 8.08 (d, J=8.1 Hz, 2H), 8.18 (d, J=7.8 Hz, 2H), 8.77–8.79 (m, 4H), 8.84–8.87 (m, 4H); LD-MS obsd 983.1; HRMS (FAB) obsd 982.1943, calcd 982.1906 ($C_{55}H_{47}IN_4SiZn$); $\lambda_{abs}$ 425, 550, 592 nm.

Example 17

Magnesium-(II)-5,15-bis(pentafluorophenyl)-10-(4-iodophenyl)-20-[4-[2-(trimethylsilyl) ethoxycarbonyl]phenyl]porphyrin (Mg-6e)

Following a general procedure (Lindsey, J. S., Woodford, J. N. *Inorg. Chem.* 1995, 34, 1063–1069), to a solution of 6e (106 mg, 99.4 μmol) in $CH_2Cl_2$ (15 mL) was added TEA (690 μL, 4.92 mmol), followed by $MgBr_2 \cdot O(Et)_2$ (639 mg, 2.47 mmol). After 30 min, the mixture was diluted with $CH_2Cl_2$ (20 mL), washed with 5% $NaHCO_3$, dried ($Na_2SO_4$), and concentrated affording a purple solid. Column chromatography (alumina, $CH_2Cl_2$) afforded a purple solid (83 mg, 77%): $^1$H NMR (THF-$d_8$) δ 0.20 (s, 9H), 1.31 (t, 2H), 4.61 (t, 2H), 7.98 (d, J=8.1 Hz, 2H), 8.14 (d, J=8.1 Hz, 2H), 8.31 (d, J=8.1 Hz, 2H), 8.42 (d, J=8.1 Hz, 2H), 8.80–8.90 (m, 8H); LD-MS obsd 1085.0; HRMS (FAB) obsd 1086.077, calcd 1086.079 ($C_{50}H_{29}F_{10}IMgN_4O_2Si$); $\lambda_{abs}$ 427, 522, 561, 604 nm.

Example 18

Magnesium-(II)-5,15-bis(pentafluorophenyl)-10-phenyl-20-[4-[2-(trimethylsilyl)ethoxycarbonyl] phenyl]porphyrin (Mg-6f)

Following a general procedure (Lindsey, J. S., Woodford, J. N. *Inorg. Chem.* 1995, 34, 1063–1069), to a solution of 6f (16.0 mg, 17.0 μmol) in $CH_2Cl_2$ (5 mL) was added TEA (94 μL, 0.68 mmol), followed by $MgBr_2 \cdot O(Et)_2$ (88.0 mg, 0.34 mmol). The mixture was stirred at room temperature for 15 h. Column chromatography (silica, $CHCl_3$) afforded a purple solid (14.4 mg, 88%): $^1$H NMR (400 MHz) δ 0.00 (s, 9H), 0.79 (t, 2H), 3.40 (brs, 2H), 7.75–7.79 (m, 5H), 8.03 (d, J=8.4 Hz, 2H), 8.23 (d, J=6.8 Hz, 2H), 8.76 (d, J=4.8 Hz, 2H), 8.81–8.84 (m, 4H), 8.98 (d, J=4.4 Hz, 2H); LD-MS obsd 958.4; HRMS (FAB) obsd (submitted), calcd 960.1829 ($C_{50}H_{30}F_{10}MgN_4O_2Si$); $\lambda_{abs}$ 426, 522, 561, 604 nm.

Example 19

Zinc-(II)-5,10,15-tri-p-tolyl-20-(4-bromophenyl) porphyrin (Zn-6g)

A sample of 6g (54 mg, 74 μmol) was treated with $Zn(OAc)_2 \cdot 2H_2O$ (80 mg, 0.36 mmol) following the general procedure. Column chromatography (silica, $CHCl_3$) afforded a purple solid (44 mg, 75%): $^1$H NMR δ 2.72 (s, 9H), 7.56 (d, J=7.2 Hz, 6H), 7.89 (d, J=8.1 Hz, 2H), 8.11 (d, J=7.5 Hz, 8H), 8.89–8.96 (m, 8H); LD-MS obsd 797.7; HRMS (FAB) obsd 796.1185, calcd 796.1180 ($C_{47}H_{33}BrN_4Zn$); $\lambda_{abs}$ 424, 514, 551, 590 nm.

Example 20

Magnesium-(II)-5,10,15-tri-p-tolyl-20-(4-bromophenyl)porphyrin (Mg-6g)

Following a general procedure (Lindsey, J. S., Woodford, J. N. *Inorg. Chem.* 1995, 34, 1063–1069), a solution of 6g (100 mg, 136 μmol) in $CH_2Cl_2$ (30 mL) was added DIEA (1.18 mL, 6.80 mmol) and $MgI_2$ (1.89 g, 6.80 mmol). After 2 h, the mixture was washed with 5% $NaHCO_3$, dried ($Na_2SO_4$), and concentrated. Column chromatography (alumina, $CHCl_3$) afforded a purple solid (84 mg, 81%): $^1$H NMR δ 2.72 (s, 9H), 7.54 (d, J=7.2 Hz, 6H), 7.87 (d, J=8.1 Hz, 2H), 8.09–8.12 (m, 8H), 8.82 (d, J=5.1 Hz, 2H), 8.89–8.92 (m, 6H); LD-MS obsd 758.5; HRMS (FAB) obsd 756.1766, calcd 756.1739 ($C_{47}H_{33}BrMgN_4$); $\lambda_{abs}$ 428, 526, 565, 605 nm.

Example 21

Zinc(II)-5-Mesityl-10-(4-ethynylphenyl)-15-[4-(hexyloxy)phenyl]-20-(4-methoxyphenyl)porphyrin (Zn-6a')

A mixture of Zn-6a (138 mg, 0.146 mmol) and TBAF (175 μL, 175 μmol, 1.0 M in THF) in THF/$CHCl_3$ (12 mL, 2:1) was stirred at room temperature for 3 h. The solvent was removed and the residue was chromatographed (silica, $CH_2Cl_2$) yielding a purple solid (122 mg, 96%): $^1$H NMR δ 0.99 (t, 3H), 1.47 (m, 4H), 1.64 (m, 2H), 1.84 (s, 6H), 1.99 (m, 2H), 2.64 (s, 3H), 3.31 (s, 1H), 4.09 (s, 3H), 4.26 (t, 2H), 7.26–7.29 (m, 4H), 7.88 (d, J=8.1 Hz, 2H), 8.10 (d, J=8.7 Hz, 2H), 8.14 (d, J=8.7 Hz, 2H), 8.20 (d, J=8.1 Hz, 2H), 8.70–8.90 (m, 10 H); LD-MS obsd 870.7; HRMS (FAB) obsd 872.3070, calcd 872.3069 ($C_{56}H_{48}N_4O_2Zn$); $\lambda_{abs}$ 426, 552, 593 nm.

Example 22

Zinc(II)-5,15-Dimesityl-10-(4-ethynylphenyl)-20-(4-bromophenyl)porphyrin (Zn-6c')

A mixture of Zn-6c (123 mg, 131 μmol) and TBAF (157 μL, 157 μmol, 1.0 M in THF) in THF/$CHCl_3$ (12 mL, 2:1) was stirred at room temperature for 30 min. The solvent was removed and the residue was chromatographed [silica, $CH_2Cl_2$/hexanes (7:3)] yielding a purple solid (87 mg, 77%): $^1$H NMR δ 1.81 (s, 12H), 2.63 (s, 6H), 3.31 (s, 1H), 7.28 (s, 4H), 7.87 (d, J=8.1 Hz, 4H), 8.10 (d, J=8.1 Hz, 2H), 8.19 (d, J=8.7 Hz, 2H), 8.78 (d, J=6.0 Hz, 4H), 8.84 (d, J=3.6 Hz, 4H); LD-MS obsd 859.1; HRMS (FAB) obsd 862.1624, calcd 862.1650 ($C_{52}H_{39}BrN_4Zn$); $\lambda_{abs}$ 419, 550, 590 nm.

Example 23

Dyad 9

To samples of Zn-6g (10 mg, 13 μmol), Zn-6i' (10 mg, 12 μmol), $Pd_2(dba)_3$ (2.1 mg, 2.3 μmol), and $P(o-tol)_3$ (4.8 mg, 16 μmol) was added a degassed solution of toluene/ triethylamine (5:1, 6 mL). The mixture was placed in an oil bath at 80° C. Aliquots were removed at 1 h and 3 h and analyzed by analytical SEC and LD-MS. The reaction mixture was passed over a silica column (THF), then loaded onto a preparative SEC column (THF). The dimer fraction was concentrated and analyzed by analytical SEC and LD-MS (with or without added POPOP, see text).

Example 24

Dyad 10

To samples of Mg-6g (9.4 mg, 11.3 μmol), Zn-6i' (8.4 mg, 11.1 μmol), $Pd_2(dba)_3$ (1.6 mg, 1.7 μmol), and $P(o-tol)_3$ (3.7 mg, 12 μmol) was added a degassed solution of toluene/triethylamine (5:1, 6 mL). The reaction mixture was placed in an oil bath at 50° C. Aliquots were removed at 1 h and 2 h timepoints for analysis (LD-MS and SEC, 1 h timepoint, SEC, 2 h timepoint). After 2 h, the reaction had appeared to stop (based on SEC data); therefore, another batch of catalyst was added [1.8 mg Pd$_2$(dba)$_3$; 3.9 mg P(o-tol)$_3$]. After an additional 1 h, SEC analysis of a reaction aliquot indicated the reaction was complete. The mixture was filtered through a short alumina column (CHCl$_3$), chromatographed on SEC (THF) and filtered through a silica column (CHCl$_3$) affording a purple powder (12.6 mg, 75%): $^1$H NMR δ 1.88 (s, 18H), 2.65 (s, 9H), 2.73 (s, 9H), 7.28–7.30 (m, 6H), 7.55–7.58 (m, 6H), 8.06 (d, J=8.1 Hz, 4H), 8.12–8.15 (m, 6H), 8.30–8.33 (m, 4H), 8.72 (s, 4H), 8.80 (d, J=4.2 Hz, 2H), 8.91–8.96 (m, 10H); LD-MS obsd 1503.2; FAB-MS obsd 1505.555, calcd 1505.549 (C$_{102}$H$_{78}$MgN$_8$Zn); λ$_{abs}$ 431, 553, 564, 606 nm.

Example 25

Dyad 11

To samples of Zn-6c' (30.0 mg, 34.7 μmol), Zn-6b (36.1 mg, 34.7 μmol), Pd$_2$(dba)$_3$ (4.8 mg, 5.2 μmol), and P(o-tol)$_3$ (12.6 mg, 41.6 μmol) was added a degassed solution of toluene/triethylamine (5:1, 15 mL). The mixture was stirred at room temperature. After 3 h, the mixture was concentrated, then passed through an alumina column (CHCl$_3$). The porphyrin-containing fractions were concentrated, then loaded onto a preparative SEC column (THF). The dyad fraction was concentrated, then passed through a silica column [toluene/THF (95:5)] affording a purple solid (37.0 mg, 60%): $^1$H NMR δ 0.39 (s, 9H), 1.00 (t, 3H), 1.45 (m, 4H), 1.65 (m, 2H), 1.85 (s, 18H), 1.99 (t, 2H), 2.65 (s, 9H), 4.26 (t, 2H), 7.27 (s, 1H), 7.30 (s, 7H), 7.88 (d, J=8.7 Hz, 4H), 8.07 (d, J=8.1 Hz, 4H), 8.11 (d, J=8.7 Hz, 4H), 8.19 (d, J=8.1 Hz, 2H), 8.31 (dd, J$^1$=2.1 Hz, J$^2$=2.4 Hz, 4H), 8.81–8.92 (m, 10H), 8.97–9.05 (m, 6H); LD-MS calcd avg mass 1779.7 obsd 1779.4 (C$_{110}$H$_{91}$BrN$_8$OSiZn$_2$); λ$_{abs}$ 430, 514, 551, 592 nm.

Example 26

Dyad 12'

Following a general procedure (Wagner, R. W. et al., Chem. Mater. 1999, 11, 29742983), to samples of Zn-6a' (54.1 mg, 61.9 μmol), Zn-6b (62.5 mg, 60.0 μmol), Pd$_2$(dba)$_3$ (11.7 mg, 12.8 μmol), and P(o-tol)$_3$ (22.7 mg, 74.5 μmol) was added a degassed solution of toluene/triethylamine (20 mL, 5:1). The flask was placed in an oil bath at 35° C. The mixture was stirred for 3 h then concentrated to a purple/brown solid. The solid was filtered [silica, 4×8 cm, hexanes/CH$_2$Cl$_2$ (1:1)] to remove P(o-tol)$_3$, and the porphyrinic products were eluted upon enrichment with CH$_2$Cl$_2$. The porphyrinic fractions were passed through a preparative SEC column (THF). The dyad fraction was concentrated, dissolved in CHCl$_3$, and chromatographed [silica, 4×8 cm, CHCl$_3$/hexanes (4:1)]. The porphyrin fraction was concentrated, yielding a purple solid (61 mg, 57%): $^1$H NMR δ 0.38 (s, 9H), 1.00 (t, 6H), 1.48 (m, 8H), 1.65 (m, 4H), 1.87 (s, 12H), 2.00 (m, 4H), 2.65 (s, 6H), 4.10 (s, 3H), 4.27 (t, 4H), 7.26–7.31 (m, 8H), 7.90 (d, J=8.1 Hz, 2H), 8.06–8.23 (m, 14H), 8.32 (d, J=7.2 Hz, 4H), 8.80–9.06 (m, 16H); LD-MS obsd 1783.8; HRMS (FAB) obsd 1788.63, calcd 1788.63 (C$_{114}$H$_{100}$N$_8$O$_3$SiZn$_2$); λ$_{abs}$ 430, 516, 552, 593 nm.

The porphyrin (61 mg, 34 μmol) was then dissolved in THF/CHCl$_3$ (8 mL, 2:1). A solution of TBAF (40 μL, 40 μmol, 1.0 M in THF) was added. The mixture was stirred at room temperature for 2 h. The solvent was removed and the sample was redissolved in CHCl$_3$ (20 mL). The solution was washed with 10% aqueous NaHCO$_3$ (20 mL), water, dried (Na$_2$SO$_4$), filtered, and concentrated affording a purple solid. Purification by column chromatography [silica, 4×10 cm, CHCl$_3$/hexanes (4:1)] afforded a purple solid (53 mg, 91%): $^1$H NMR δ 1.00 (t, 6H), 1.48 (m, 8H), 1.65 (m, 4H), 1.87 (s, 12H), 2.00 (m, 4H), 2.65 (s, 6H), 3.32 (s, 1H), 4.10 (s, 3H), 4.27 (t, 4H), 7.26–7.31 (m, 8H), 7.90 (d, J=8.1 Hz, 2H), 8.06–8.23 (m, 14H), 8.32 (d, J=7.2 Hz, 4H), 8.80–9.06 (m, 16H); LD-MS obsd 1710.7; HRMS (FAB) obsd 1712.58, calcd 1712.59 (C$_{111}$H$_{92}$N$_8$O$_3$Zn$_2$); λ$_{abs}$ 430, 516, 553, 594 nm.

Example 27

Triad 13

To samples of 12' (35.5 mg, 20.7 μmol), Mg-6e (26.1 mg, 24.0 μmol), Pd$_2$(dba)$_3$ (5.2 mg, 5.7 μmol), and P(o-tol)$_3$ (8.9 mg, 29 μmol) was added a degassed solution of toluene/triethylamine (5:1, 7.0 mL). The flask was placed in an oil bath at 35° C. After 2 h, the reaction was judged complete by analytical SEC. The volatile components were removed and the solid was filtered through an alumina column (CHCl$_3$/hexanes, 4:1). Fractions containing porphyrin were concentrated and the porphyrin mixture was chromatographed (SEC, THF). Column chromatography [alumina, CHCl$_3$/hexanes (4:1) followed by slow enrichment with THF] afforded a purple solid (41.2 mg, 75%): $^1$H NMR (500 MHz) (THF-d$_8$) δ 0.17 (s, 9H), 0.99 (m, 6H), 1.28 (t, 2H), 1.60–1.75 (m, 8H), 1.80–1.90 (m, 4H), 1.85 (s, 6H), 1.88 (s, 6H), 1.97 (m, 4H), 2.59 (s, 3H), 2.61 (s, 3H), 4.04 (s, 3H), 4.26 (m, 4H), 4.59 (t, 2H), 7.26–7.31 (m, 12H), 8.04–8.11 (m, 12H), 8.28–8.32 (m, 8H), 8.40 (d, J=7.8 Hz, 4H), 8.65 (d, J=4.5 Hz, 2H), 8.71 (d, J=4.5 Hz, 2H), 8.74 (d, J=4.5 Hz, 4H), 8.81–8.95 (m, 16H); MALDI (POPOP) obsd 2676.2, calcd avg mass 2675.9 (C$_{161}$H$_{120}$F$_{10}$MgN$_{12}$O$_5$SiZn$_2$); λ$_{abs}$ 427, 435, 521, 558, 599 nm.

Example 28

Triad 13'

To a sample of 13 (15 mg, 5.6 μmol) in THF/DMF (4 mL, 1:1) was added TBAF (6.7 μL, 6.7 μmol, 1.0 M in THF). The mixture was stirred at room temperature until LD-MS showed no starting material (24 h). Additional THF (5 mL) was added and the solution was poured into 50 mL of water. The resulting solid was filtered, washed copiously with water, then methanol, yielding a purple solid (10.4 mg, 72%): LD-MS obsd 2571.46, calcd avg mass 2575.9 (C$_{156}$H$_{108}$F$_{10}$MgN$_{12}$O$_5$Zn$_2$); λ$_{abs}$ 427, 435, 520, 561, 602 nm.

Example 29

Dyad 14

To samples of Zn-6c' (90.0 mg, 104 μmol), Mg-6e (113.1 mg, 104 μmol), Pd$_2$(dba)$_3$ (14.3 mg, 15.6 μmol), and P(o-tol)$_3$ (38.0 mg, 125 μmol) was added a degassed solution of toluene/triethylamine (5:1, 40 mL). The mixture was stirred at room temperature for 1 h 45 min at which time additional Pd$_2$(dba)$_3$ (14.3 mg, 15.6 μmol) and P(o-tol)$_3$ (38.0 mg, 125 μmol) were added. After a total of 4 h 20 min, the reaction mixture was concentrated, then loaded onto an alumina column (CHCl$_3$). The porphyrin-containing fractions were then loaded onto a preparative SEC column (THF). The nearly pure dimer fraction was then loaded onto a silica column [CHCl$_3$/hexanes/TEA (95:5:1)]. Trituration with hexanes followed by filtration afforded a purple solid (115 mg, 60%): $^1$H NMR (THF-d$_8$) δ 0.20 (s, 9H), 1.31 (t, 2H), 1.86 (s, 12H), 2.62 (s, 6H), 4.61 (t, 2H), 7.32 (s, 4H), 7.91 (d, J=9.0 Hz, 2H), 8.05–8.14 (m, 6H), 8.31 (dd, J$^1$=2.1 Hz, J$^2$=1.5 Hz, 6H), 8.42 (d, J=7.8 Hz, 2H), 8.69 (d, J=4.2 Hz, 2H), 8.72 (d, J=4.2 Hz, 2H), 8.78 (d, J=4.5 Hz, 2H), 8.83 (d, J=5.1 Hz, 2H), 8.88–8.97 (m, 8H); LD-MS obsd 1824.7, calcd avg mass 1824.3 (C$_{102}$H$_{67}$BrF$_{10}$MgN$_8$O$_2$SiZn); λ$_{abs}$ 430, 554, 591 nm.

Example 30

Tetrad 15

To samples of 12' (50.0 mg, 29.1 μmol), 14 (53.1 mg, 29.1 μmol), Pd$_2$(dba)$_3$ (4.0 mg, 4.4 μmol), and P(o-tol)$_3$ (10.6 mg, 34.9 μmol) was added a degassed solution of toluene/triethylamine (5:1, 18 mL). The mixture was stirred at 50° C. for 2.5 h at which time additional Pd$_2$(dba)$_3$ (4.0 mg, 4.4 μmol) and P(o-tol)$_3$ (10.6 mg, 34.9 μmol) were added. After a total of 5 h, the reaction mixture was concentrated, then loaded onto an alumina column [toluene/THF (9:1)]. The porphyrin-containing fractions were then loaded onto a preparative SEC column (THF). Some streaking occurred during purification. A second SEC column was run (THF). The tetrad-containing fractions were passed over an alumina column [toluene/THF (9:1)] to afford a purple solid (43 mg, 43%): $^1$H NMR (THF-d$_8$) δ 0.22 (s, 9H), 1.01 (m, 6H), 1.83 (s, 8H), 1.88 (s, 16H), 2.63 (s, 4H), 2.65 (s, 8H), remaining aliphatic CH$_2$ resonances are broad and cannot be integrated with accuracy, 4.07 (s, 3H), 4.24 (m, 4H), 6.91 (s, 8H), 7.34 (m, 12H), 8.10 (m, 16H), 8.34–8.42 (m, 12H), 8.75–8.97 (m, 32H); MALDI (POPOP) obsd 3464.1, calcd avg mass 3460.2 (C$_{213}$H$_{158}$F$_{10}$MgN$_{16}$O$_5$SiZn$_3$); λ$_{abs}$ 436, 551, 592 nm.

Example 31

Tetrad 15'

To a solution of 15 (33.6 mg, 9.7 μmol) in THF/DMF (40 mL, 10:1) was added TBAF (14.6 μL, 14.6 μmol, 1.0 M in THF). The solution was stirred at 60° C. for 12 h. LD-MS still showed a significant amount of starting material, therefore another 15 μL of TBAF was added. The mixture was stirred for another 5 h (LD-MS did not detect any starting material). The mixture was concentrated to a purple solid and triturated with methanol. The suspension was filtered, then washed with methanol, H$_2$O, then methanol again to recover 16.3 mg (50%) of a purple solid: MALDI (POPOP) obsd 3362.1, calcd avg mass 3360.0 (C$_{208}$H$_{146}$F$_{10}$MgN$_{16}$O$_5$Zn$_3$); μ$_{abs}$ 435, 553, 594 mn.

Example 32

Dyad 16

To samples of Zn-6c' (52.5 mg, 60.6 μmol), Zn-6d (59.7 mg, 60.6 μmol), Pd$_2$(dba)$_3$ (8.3 mg, 9.1 μmol), and P(o-tol)$_3$ (22.1 mg, 72.7 μmol) was added a degassed solution of toluene/triethylamine (5:1, 20 mL). The mixture was stirred at room temperature. An aliquot was removed after 1 h and analyzed by SEC. Because of the modest conversion to dyad another identical batch of Pd$_2$(dba)$_3$ and P(o-tol)$_3$ was added after 1.5 h. After an additional 2 h (3.5 h total reaction time), an aliquot was removed and analyzed by SEC. After 4 h, the mixture was concentrated then passed through an alumina column (toluene). The porphyrin-containing fractions were concentrated, then loaded onto a preparative SEC column (THF). The dyad fraction was then passed through a silica column [toluene/THF (95:5)]. The purple solid was triturated with hexanes, filtered, then washed with hexanes, methanol, and then hexanes again. The solid was then dissolved in THF and concentrated affording a purple solid (62.1 mg, 60%): $^1$H NMR (THF-d$_8$) δ 0.36 (s, 9H), 1.87 (s, 24H), 2.62 (s, 12H), 7.32 (s, 8H), 7.83 (d, J=8.1 Hz, 2H), 7.91 (d, J=8.1 Hz, 2H), 8.06 (d, J=8.1 Hz, 4H), 8.12 (d, J=8.1 Hz, 2H), 8.19 (d, J=8.1 Hz, 2H), 8.31 (d, J=8.1 Hz, 4H), 8.68–8.73 (m, 8H), 8.78–8.80 (m, 4H), 8.89 (d, J=4.5 Hz, 4H); LD-MS calcd avg mass 1722.1, obsd 1722.1 (C$_{107}$H$_{85}$BrN$_8$SiZn$_2$); λ$_{abs}$ 429, 513, 550, 591 nm.

Example 33

Dyad 16'

Dyad 16 (65 mg, 38 μmol) was then dissolved in THF (7 mL). A solution of TBAF (45 μL, 45 μmol, 1.0 M in THF) was added. The mixture was stirred at room temperature for 1 h. The solvent was removed by rotary evaporation. Column chromatography (silica, toluene) afforded a purple solid (52 mg, 84%): $^1$H NMR δ (toluene-d8, 400 MHz) 2.11 (s, 24H) 2.55 (s, 12H), 2.93 (s, 1H), 7.27 (s, 8H), 7.58 (d, J=8.0 Hz, 2H), 7.72 (d, J=7.6 Hz, 2H), 7.78 (d, J=8.0 Hz, 2H), 7.94 (d, J=8.4 Hz, 2H), 8.00 (d, J=8.0 Hz, 4H), 8.12 (d, J=7.8 Hz, 4H), 8.84 (d, J=4.4 Hz, 2H), 8.86 (d, J=4.4 Hz, 2H), 8.90 (d, J=4.8 Hz, 2H), 8.92 (d, J=4.8 Hz, 2H), 8.95 (d, J=4.8 Hz, 4H), 9.02 (d, J=4.4 Hz, 4H); LD-MS obsd 1651.2; calcd avg mass 1649.5 (C$_{104}$H$_{77}$BrN$_8$Zn$_2$); λ$_{abs}$ 429, 513, 550, 591 nm.

Example 34

Tetrad 17

To samples of 16 (16.6 mg, 9.69 μmol), 12' (16.7 mg, 9.70 μmol), Pd$_2$(dba)$_3$ (1.3 mg, 1.4 μmol), and P(o-tol)$_3$ (3.5 mg, 12 μmol) was added a degassed solution of toluene/triethylamine (5:1, 6 mL). The mixture was placed in an oil bath at 50° C. The reaction mixture was not homogeneous. Analytical SEC after 1 h showed 23% conversion to tetrad. After 90 min, additional Pd$_2$(dba)$_3$ (1.3 mg, 1.4 μmol), and P(o-tol)$_3$ (3.5 mg, 12 μmol) were added. Analytical SEC after 4.5 h showed 51% conversion to tetrad. After 5 h, the reaction mixture was loaded directly onto an alumina column [toluene/THF (95:5)]. The porphyrin fractions were dissolved in THF/toluene (95:5) then loaded onto a preparative SEC column (THF). The tetrad fraction was triturated with hexanes, filtered, then washed with hexanes, methanol, and then hexanes again. The solid was then dissolved in THF and concentrated affording a purple solid (10.1 mg, 31%): $^1$H NMR (THF-d$_8$) δ 0.36 (s, 9H), 0.91 (t, 6H), 1.50 (m, 4H), 1.88 (d, 36H), 2.63 (d, 18H), remaining aliphatic CH$_2$ resonances are buried under the large THF signal and the mesityl resonances, 4.07 (s, 3H), 4.29 (m, 4H), 7.32 (m, 20H), 8.09 (m, 24H), 8.32 (m, 8H), 8.68–8.78 (m, 12H), 8.83–8.97 (m, 20H); LD-MS obsd 3355.9, calcd avg mass, 3357.48 (C$_{218}$H$_{176}$N$_{16}$O$_3$SiZn$_4$); λ$_{abs}$ 427, 435, 513, 552, 593 nm.

Example 35

Triad 18

To samples of 16' (46.6 mg, 28.2 μmol), Mg-6e (30.7 mg, 28.2 μmol), Pd$_2$(dba)$_3$ (3.9 mg, 4.2 μmol), and P(o-tol)$_3$ (7.7 mg, 25.4 µmol) was added a degassed solution of toluene/triethylamine (5:1, 18 mL). The mixture was stirred at room temperature for 2 h at which time additional Pd$_2$(dba)$_3$ (4.0 mg, 4.4 µmol) and P(o-tol)3 (7.7 mg, 25.4 µmol) were added. After a total of 4.5 h, the reaction mixture was concentrated, then loaded onto an alumina column [toluene/THF (9:1)]. The porphyrin-containing fractions were then loaded onto a preparative SEC column (THF). The triad-containing fractions were passed over an alumina column [toluene/THF (9:1)] to afford a purple solid (38 mg, 51%): $^1$H NMR (THF-d$_8$) δ 0.21 (s, 9H), 1.32 (t, 2H), 1.88 (s, 12H), 1.91 (s, 12H), 2.63 (s, 6H), 2.65 (s, 6H), 4.63 (t, 2H), 7.33 (s, 4H), 7.35 (s, 4H), 7.91 (d, J=8.1 Hz, 2H), 8.07–8.15 (m, 10H), 8.31–8.35 (m, 10H), 8.44 (d, J=8.1 Hz, 2H), 8.70–8.77 (m, 8H), 8.80 (d, J=4.2 Hz, 2H), 8.85 (d, J=4.5 Hz, 2H), 8.89–8.99 (m, 12H), multiplet centered at 7.15 and singlet at 2.33 are due to toluene; LD-MS obsd 2621.5. calcd avg mass 2608.6 (C$_{154}$H$_{105}$BrF$_{10}$MgN$_{12}$O$_2$SiZn$_2$); λ$_{abs}$ 435, 553, 594 nm.

Example 36

Pentad 19

To samples of 18 (19.5 mg, 11.4 µmol), 12' (27.0 mg, 10.4 µmol), Pd$_2$(dba)$_3$ (1.4 mg, 1.6 µmol), and P(o-tol)$_3$ (2.9 mg, 9.4 µmol) was added a degassed solution of toluene/triethylamine (5:1, 8.5 mL). The mixture was placed into an oil bath at 50° C. Because the solution was not homogeneous, THF (2 mL) was added (the reaction became homogeneous). An aliquot was removed after 70 min and analyzed by SEC which revealed 25% conversion to pentamer. After 1.5 h, another identical batch of catalyst was added. After 3 h, SEC revealed 38% conversion to pentad. The reaction was stopped after 5 h and directly passed through an alumina column [toluene/THF (8:2)]. Some purple material remained bound to the top of the column. The porphyrin-containing fractions were loaded onto a preparative SEC column (THF). Severe streaking occurred which severely hampered purification. Only a small fraction of pentad was recovered (~2 mg) and due to its very poor solubility, could not be completely analyzed for purity. LD-MS obsd 4249.8, calcd avg mass 4244.5 (C$_{265}$H$_{196}$F$_{10}$MgN$_{20}$O$_5$SiZn$_4$); λ$_{abs}$ 436, 563, 593 nm.

Example 37

Dyad 20

To samples of Zn-6I' (30.0 mg, 36.2 µmol), Mg-6f (39.4 mg, 36.2 µmol), Pd$_2$(dba)$_3$ (6.6 mg, 7.2 µmol), and P(o-tol)$_3$ (13.2 mg, 43.4 µmol) was added a degassed solution of toluene/triethylamine (5:1, 15 mL). The mixture was stirred for 2.5 h at 35° C. The mixture was passed through an alumina column (CHCl$_3$). Preparative SEC (THF) followed by column chromatography [silica, toluene/THF (98:2)] afforded a purple solid. Trituration with hexanes afforded a purple solid (38.7 mg, 60%): $^1$H NMR (400 MHz) δ 0.06 (s, 9H), 1.87 (s, 18H), 2.63 (s, 3H), 2.65 (s, 6H), 3.71 (brs, 2H), 7.27 (s, 2H), 7.30 (s, 4H), 7.54 (brs, 2H), 8.03–8.06 (m, 6H), 8.12 (d, J=7.6 Hz, 2H), 8.30 (d, J=7.6 Hz, 4H), 8.73 (s, 4H), 8.81–8.87 (m, 6H), 8.91 (d, J=4.4 Hz, 2H), 8.94 (d, J=4.4 Hz, 2H), 9.08 (d, J=4.4 Hz, 2H); LD-MS obsd 1790.16, calcd avg mass 1787.53 (C$_{105}$H$_{74}$F$_{10}$MgN$_8$O$_2$SiZn$_4$); λ$_{abs}$ 430, 554, 590, 604 nm.

Example 38

S-2-Pyridyl-3-[2-(trimethylsilyl)ethynyl]benzenethioate (21a)

Following a refined procedure (Rao, P. D. et al. *J. Org. Chem.* 2000, 65, 7323–7344), samples of S-2-pyridyl-3-iodobenzenethioate (Rao, P. D. et al. *J. Org. Chem.* 2000, 65, 1084–1092) (17.1 g, 50.0 mmol), Pd$_2$(dba)$_3$ (0.83 g, 0.90 mmol), PPh$_3$ (1.97 g, 7.50 mmol), and CuI (0.95 g, 5.0 mmol) were weighed into a 250 mL Schlenk flask. The flask was pump-purged with argon three times, then THF/triethylamine (140 mL, 3:1) and trimethylsilylacetylene (11.0 mL, 75.0 mmol) were added. The flask was sealed tightly and stirred for 2 h at 50° C., at which point TLC analysis [silica, hexanes/ethyl acetate (4:1)] showed incomplete consumption of S-2-pyridyl-3-iodobenzenethioate. The flask was cooled to room temperature and additional trimethylsilylacetylene (7.00 mL, 50.0 mmol) was added. Stirring was continued at 50° C. for another 1 h, affording complete reaction. The mixture was filtered and the filtered material was washed with ethyl acetate. The filtrate was concentrated and purified by chromatography [silica, hexanes/ethyl acetate (4:1)], affording a slightly brown solid. Recrystallization from hexanes/ethyl acetate gave pale yellow crystals (12.58 g, 81%): mp 90–92° C.; $^1$H NMR δ 8.70–8.68 (m, 1H), 8.10 (m, 1H), 7.96–7.93 (m, 1H), 7.84–7.78 (m, 2H), 7.73–7.68 (m, 2H), 7.44 (t, J=8.1 Hz, 1H), 7.38–7.33 (m, 1H), 0.27 (s, 9H); $^{13}$C NMR δ 188.6, 150.9, 150.5, 137.1, 136.8, 136.5, 130.8, 130.7, 128.7, 127.2, 124.0, 123.7, 103.3, 96.1, 0.3; FAB-MS obsd 312.0898, calcd 312.0878 (C$_{17}$H$_{17}$NOSSi). Anal. Calcd: C, 65.55; H, 5.50; N, 4.50. Found: C, 65.53; H, 5.55; N, 4.45.

Example 39

1-{3-[2-(Trimethylsilyl)ethynyl]benzoyl}-5-mesityldipyrromethane (22a)

Following a standard procedure (Rao, P. D. et al. *J. Org. Chem.* 2000, 65, 7323–7344), EtMgBr (44.0 mL, 44.0 mmol, 1.0 M in THF) was added to a solution of 5-mesityldipyrromethane (5.28 g, 20.0 mmol) in dry THF (20 mL) at room temperature under argon. The mixture was stirred for 10 min at room temperature and then cooled to −78° C. A solution of 21a (6.22 g, 20.0 mmol) in THF (30 mL) was then added. The mixture was stirred at −78° C. for 10 min and then allowed to warm to room temperature. TLC analysis [silica gel, CH$_2$Cl$_2$/ethyl acetate (98:2)] showed complete consumption of 21a after 40 min. The reaction mixture was poured into a mixture of CH$_2$Cl$_2$ (200 mL) and saturated aqueous NH$_4$Cl (100 mL). The organic phase was separated, washed with brine and water, dried (Na$_2$SO$_4$), and concentrated to give a dark foam-like solid. Chromatography [silica, CH$_2$Cl$_2$/ethyl acetate (98:2)] afforded an amorphous yellow solid (7.16 g, 72%): mp 95–97° C.; $^1$H NMR δ 9.21 (s, br, 1H), 7.92(m, 1H), 7.84 (s, br, 1H), 7.77 (d, J=8.1 Hz, 1H), 7.62 (d, J=8.1 Hz, 1H), 7.40 (t, J=8.1 Hz, 1H), 6.90 (s, 2H), 6.84–6.82 (m, 1H), 6.70–6.68 (m, 1H), 6.24–6.21 (m, 1H), 6.15–6.12 (m, 2H), 5.96 (s, 1H), 2.30 (s, 3H 2.09 (s, 6H), 0.26 (s, 9H); $^{13}$C NMR δ 183.0, 141.3, 138.5, 137.4, 137.1, 134.7, 132.9, 132.1, 130.5, 129.5, 128.9, 128.6, 128.2, 123.2, 120.8, 116.9, 110.1, 108.8, 107.1, 104.1, 95.1, 38.5, 20.7, 20.6, 0.2; FAB-MS obsd 464.2311, calcd 464.2284 (C$_{30}$H$_{32}$N$_2$OSi). Anal. Calcd: C, 77.54; H, 6.94; N, 6.03. Found: C, 77.39; H, 6.83; N, 5.91.

Example 40

1-(4-Bromobenzoyl)-5-mesityldipyrromethane (22b)

Following a standard procedure, the reaction of 5-mesityldipyrromethane (1.85 g, 7.00 mmol) in THF (10 mL) with EtMgBr (15.4 mL, 15.4 mmol, 1.0 M in THF) followed by S-2-pyridyl-4-bromobenzothioate (Rao, P. D. et al. *J. Org. Chem.* 2000, 65, 7323–7344) (2.06 g, 7.00 mmol)

afforded, upon standard workup and chromatography (silica, CH$_2$Cl$_2$), a yellow foam-like solid (2.46 g, 78%): mp 120–122° C.; $^1$H NMR δ 9.24 (s, br, 1H), 7.84 (s, br, 1H), 7.72 (d, J=8.1 Hz, 2H), 7.60 (d, J=8.1 Hz, 2H), 7.00 (s, 2H), 6.80–6.78 (m, 1H), 6.69–6.68 (m, 1H), 6.23–6.20 (m, 1H), 6.15–6.12 (m, 2H), 5.95 (s, 1H), 2.29 (s, 3H), 2.09 (s, 6H); $^{13}$C NMR δ 182.7, 141.3, 137.4, 137.2, 137.1, 132.9, 131.5, 130.5, 130.3, 129.5, 128.9, 126.3, 120.5, 116.9, 110.2, 108.9, 107.2, 38.6, 20.7; FAB-MS obsd 446.0979, calcd 446.0994 (C$_{25}$H$_{23}$BrN$_2$O). Anal Calcd: C, 67.12; H, 5.18; N, 6.26. Found: C, 67.11; H, 5.23; N, 6.23.

Example 41

1-(3-Iodobenzoyl)-5-mesityl-9-{3-[2-(trimethylsilyl) ethynyl]benzoyl}dipyrromethane (23a)

Following a standard procedure (Rao, P. D. et al. *J. Org. Chem.* 2000, 65, 7323–7344), a solution of monoacyldipyrromethane 22a (7.03 g, 14.2 mmol) in toluene (60 mL) was treated with EtMgBr (28.4 mL, 28.4 mmol, 1.0 M in THF) under argon. After stirring at room temperature for 5 min, a solution of 3-iodobenzoyl chloride (3.78 g, 14.2 mmol) in toluene (2 mL) was added under argon. Stirring was continued at room temperature for 10 min. EtMgBr (28.4 mL, 28.4 mmol) was again added followed by stirring for 5 min, then 3-iodobenzoyl chloride (3.78 g, 14.2 mmol) in toluene (2 mL) was added. After 15 min, TLC analysis [silica, CH$_2$Cl$_2$/ethyl acetate (98:2)] indicated complete consumption of 22a. The reaction mixture was poured into a mixture of saturated aqueous NH$_4$Cl (200 mL) and ethyl acetate (300 mL). The organic phase was separated, washed with brine and water, dried (Na$_2$SO$_4$) and concentrated. Chromatography (silica, CH$_2$Cl$_2$) followed by recrystallization (CH$_2$Cl$_2$/methanol) afforded a brown solid (6.76 g, 68%): mp 100–102° C.; $^1$H NMR δ 10.18 (s, br, 2H), 8.08 (m, 1 H), 7.86–7.83 (m, 2H), 7.75–7.69 (m, 2H), 7.59 (d, J=8.1 Hz, 1H), 7.36 (t, J=8.1 Hz, 1H), 7.17 (t, J=8.1 Hz, 1H), 6.94 (s, 2H), 6.77–6.72 (m, 2H), 6.12 (s, 1H), 6.10 (s, 2H), 2.32 (s, 3H), 2.19 (s, 6H), 0.25 (s, 9H); $^{13}$C NMR δ 182.5, 181.7, 140.8, 140.5, 140.1, 139.8, 138.4, 138.0, 137.4, 137.0, 134.0, 133.1, 133.0, 130.2, 130.0, 129.8, 129.6, 129.1, 128.2, 127.9, 122.9, 121.5, 121.4, 110.8, 110.7, 104.2, 94.8, 93.5, 39.2, 20.9, 0.2; FAB-MS obsd 694.1531, calcd 694.1513 (C$_{37}$H$_{35}$IN$_2$O$_2$Si). Anal. Calcd: C, 63.97; H, 5.08; N, 4.03. Found: C, 63.81; H, 5.18; N, 3.98.

Example 42

1-(4-Bromobenzoyl)-5-mesityl-9-(4-iodobenzoyl) dipyrromethane (23b)

Following a standard procedure, a solution of monoacyldipyrromethane 22b (2.46 g, 5.50 mmol) in toluene (25 mL) was treated with EtMgBr (11.0 mL, 11.0 mmol, 1.0 M in THF) under argon for 5 min at room temperature. Then 4-iodobenzoyl chloride (1.47 g, 5.50 mmol) was added under argon and the mixture was stirred for 10 min at room temperature. This procedure was repeated twice [EtMgBr (11.0 mL, 11.0 mmol), 4-iodobenzoyl chloride (1.47 g, 5.50 mmol); EtMgBr (5.5 mL, 5.5 mmol), 4-iodobenzoyl chloride (0.74 g, 2.78 mmol)]. The mixture was stirred at room temperature for 30 min, followed by standard workup and chromatography [silica, CH$_2$Cl$_2$/ethyl acetate (98:2)]. Precipitation of the product from CH$_2$Cl$_2$/methanol afforded a yellow solid (2.21 g, 73%): mp 233–235° C. (dec.); $^1$H NMR δ 10.35 (s, br, 2H), 7.78 (d, J=8.7 Hz, 2H), 7.63 (d, J=8.7 Hz, 2H), 7.56 (d, J=8.7 Hz, 2H), 7.48 (d, J=8.7 Hz, 2H), 6.93 (s, 2H), 6.70–6.68 (m, 2H), 6.10–6.07 (m, 3H), 2,32 (s, 3H), 2.18 (s, 6H); $^{13}$C NMR δ 182.7, 182.4, 140.5, 137.4, 137.2, 136.9, 132.9, 131.2, 130.8, 130.3, 130.0, 126.4, 121.1, 110.7, 98.9, 39.2, 20.8; FAB-MS obsd 676.0245, calcd 676.0222 (C$_{32}$H$_{26}$BrIN$_2$O$_2$). Anal Calcd: C, 56.74; H, 3.87; N, 4.14. Found: C, 56.96; H, 4.08; N, 3.94.

Example 43

5,15-Dimesityl-10-{3-[2-(trimethylsilyl)ethynyl] phenyl}-20-(3-iodophenyl)porphyrin (24a)

Following a standard procedure (Rao, P. D. et al. *J. Org. Chem.* 2000, 65, 7323–7344), a solution of diacyldipyrromethane 23a (2.78 g, 4.00 mmol) in dry THF/methanol (176 mL, 10:1) was treated with NaBH$_4$ (3.02 g, 80.0 mmol) in portions and the mixture was stirred at room temperature. TLC analysis [alumina, ethyl acetate/CH$_2$Cl$_2$ (1:1)] showed that the reduction was complete after 30 min. The reaction mixture was poured into a mixture of saturated aqueous NH$_4$Cl (200 mL) and CH$_2$Cl$_2$ (300 mL). The organic phase was washed with brine and water, dried (Na$_2$SO$_4$) and concentrated. The resulting residue was dried under vacuum for 15 min. To the freshly prepared dipyrromethane-dicarbinol (4.00 mmol) was added 5-mesityldipyrromethane (1.06 g, 4.00 mmol) and CH$_3$CN (1600 mL) at room temperature. TFA (3.68 mL, 48.0 mmol, 30 mM) was added. The solution instantly turned dark. After 3.5 min, the spectroscopic yield of porphyrin had leveled off. Then DDQ (2.72 g, 12.0 mmol) was added and the mixture was stirred for 1 h at room temperature. Triethylamine (6.80 mL, 48.0 mmol) was then added. The mixture was filtered through a pad of alumina (eluted with CH$_2$Cl$_2$). Removal of the solvent gave a dark solid which was redissolved in CH$_2$Cl$_2$ (30 mL) and chromatographed (silica, CH$_2$Cl$_2$), affording a purple solid (0.75 g, 20%). The $^1$H NMR data were identical to those reported for the product obtained from a mixed aldehyde condensation (Ravikanth, M. et al. *Tetrahedron* 1998, 54, 7721–7734).

Example 44

5,15-Dimethyl-10-(4-bromophenyl)-20(4-iodophenyl)porphyrin (24b)

Following a standard procedure, a solution of 1-(4-bromobenzoyl)-9-(1-iodobenzoyl)dipyrromethane (1.90 g, 2.80 mmol) in THF/methanol (160 mL, 3:1) was treated with NaBH$_4$ (5.18 g, 140 mmol). Standard workup and condensation with 5-mesityldipyrromethane (0.74 g, 2.80 mmol) in CH$_3$CN (1120 mL) using TFA (2.60 mL, 30 mM) was followed by oxidation with DDQ (1.93 g, 8.4 mmol). The standard workup, including chromatography (silica, CH$_2$Cl$_2$) followed by sonication with methanol afforded a purple solid (513 mg, 24%): $^1$H NMR δ 8.78–8.76 (m, 4H), 8.70 (d, J=4.5 Hz, 4H), 8.08 (d, J=8.1 Hz, 4H), 7.95 (d, J=8.7 Hz, 2H), 7.88 (d, J=8.1 Hz, 2H), 7.29 (s, 4H), 2.63 (s, 6H), 1.82 (s, 12H), −2.68 (s, br, 2H); LD-MS obsd 902.8; FAB-MS obsd 902.1478, calcd 902.1481 (C$_{50}$H$_{40}$BrIN$_4$); λ$_{abs}$ 420, 515, 548, 592, 648 nm; λ$_{em}$ (λ$_{ex}$=520 nm), 650, 719 nm.

Example 45

Zn(II)-5,15-Dimesityl-10-{3-[2-(trimethylsilyl) ethynyl]phenyl}-20-(3iodophenyl)porphyrin (Zn-24a)

A solution of 24a (0.71 g, 0.77 mmol) in CHCl$_3$ (150 mL) was treated with a solution of Zn(OAc)$_2$.2H$_2$O (0.85 g, 3.85 mmol) in methanol (5 mL) at room temperature for 3 h. The standard workup afforded a purple solid (0.72 g, 95%): $^1$H NMR δ 8.86–8.83 (m, 4H), 8.80–8.77 (m, 4H), 8.60–8.59 (m, 1H), 8.35 (m, 1H), 8.16 (m, 2H), 8.11 (d, J=8.7 Hz, 1H), 7.88 (d, J=8.1 Hz, 1H), 7.67 (t, J=8.1 Hz, 1H), 7.47 (t, J=8.1 Hz, 1H), 7.29 (s, 4H), 2.64 (s, 6H), 1.82 (m, 12H), 0.25 (s, 9H); LD-MS obsd 985.9; FAB-MS obsd 982.1916, calcd 982.1906 ($C_{55}H_{47}IN_4SiZn$); λabs 424, 550, 590 nm; $\lambda_{em}$ ($\lambda_{ex}$=550 nm) 645, 595 nm.

Example 46

Zn(II)-5,15-Dimethyl-10-(4-bromophenyl)-20(4-iodophenyl)porphyrin (Zn-24b)

A solution of porphyrin 24b (506 mg, 0.56 mmol) in $CHCl_3$ (140 mL) was treated with $Zn(OAc)_2 \cdot 2H_2O$ (613 mg, 2.80 mmol) overnight at room temperature. Standard workup and sonication with methanol afforded a purple solid (515 mg, 95%): $^1$H NMR δ 8.86 (d, J=4.5 Hz, 2H), 8.85 (d, J=4.5 Hz, 2H), 8.78 (d, J=4.5 Hz, 4H), 8.10 (d, J=6.6 Hz, 2H), 8.07 (d, J=6.6 Hz, 2H), 7.97 (d, J=8.1 Hz, 2H), 7.87 (d, J=8.1 Hz, 2H), 7.28 (s, 4H), 2.63 (s, 6H), 1.82 (s, 12H); LD-MS obsd 964.0; FAB-MS obsd 964.0646, calcd 964.0616 ($C_{50}H_{38}BrIN_4Zn$); $\lambda_{abs}$ 423, 549, 589 nm; $\lambda_{em}$ ($\lambda_{ex}$=550 nm) 594, 645 nm.

Example 47

5,15-Dimesityl-10,20-bis(3-ethynylphenyl)porphyrin (26)

A solution of 5,15-dimesityl-10,20-bis[3-(2-trimethylsilylethynyl)phenyl]porphyrin (Ravikanth, M. et al. *Tetrahedron* 1998, 54, 7721–7734) (1.20 g, 1.34 mmol) in $CHCl_3$ (150 mL) was treated with TBAF (2.68 g, 2.68 mmol, 1.0–1.5 mmol F$^-$/g resin) at room temperature for 2 h. The mixture was washed with 10% aqueous $NaHCO_3$ and water. The organic layer was dried ($Na_2SO_4$) and concentrated. Chromatography [silica, $CHCl_3$/hexanes (1:1)] afforded a purple solid (0.84 g, 84%): $^1$H NMR δ 8.76 (d, J=5.1 Hz, 4H), 8.70 (d, J=5.1 Hz, 4H), 8.35 (d, J=1.5 Hz, 2H), 8.20 (d, J=7.5 Hz, 2H), 7.91 (d, J=8.1 Hz, 2H), 7.70 (d, J=8.1 Hz, 2H), 7.28 (s, 4H), 3.16 (s, 2H), 2.63 (s, 6H), 1.83 (s, 12H), −2.68 (s, 2H), LD-MS obsd 747.7; FAB-MS obsd 746.3442, calcd 746.3409 ($C_{54}H_{42}N_4$); $\lambda_{abs}$ 420, 514, 548, 591, 647 nm; $\lambda_{em}$ ($\lambda_{ex}$=520 nm) 649, 717 nm.

Example 48

ZnFbZn-m/m-CCTMS

Following the refined Pd-coupling procedure for the preparation of multiporphyrin arrays (Wagner, R. W. et al. *Chem. Mater.* 1999, 11, 2974–2983), samples of 5,15-dimesityl-10,20-bis(4-ethynylphenyl)porphyrin (25) (Li, J. et al. *J. Am. Chem. Soc.* 1999, 121, 8927–8940) (243 mg, 0.32 mmol), Zn-24a (640 mg, 0.65 mmol), $Pd_2(dba)_3$ (90 mg, 0.098 mmol), and P(o-tol)$_3$ (241 mg, 0.78 mmol) were weighed into a 250 mL Schlenk flask which was then pump-purged three times with argon. Toluene/triethylamine (132 mL, 5:1) was added and the flask was stirred at 35° C. Monitoring by analytical SEC and LD-MS showed the reaction had leveled off after 7 h. The solvent was removed and the residue was chromatographed [silica, hexanes/$CHCl_3$ (1:2)] affording unreacted porphyrin monomers followed by a mixture of mono-coupled dimer, desired trimer and high molecular weight materials (HMWM). The mixture of porphyrins was concentrated to dryness, dissolved in 20 mL of THF, and chromatographed in two equal portions (SEC, THF). Gravity elution afforded four major components (in order of elution): HMWM, desired trimer, mono-coupled byproduct (dimer, LD-MS obsd m/z at 1604.5, calcd for $C_{109}H_{88}N_8SiZn$ m/z=1604.0) and unreacted monomeric porphyrins. The trimer-containing fractions were combined and chromatographed [silica, hexanes/$CHCl_3$ (1:1)], affording the title compound as a purple solid (373 mg, 47%). Similar purification of the dimer fraction gave the byproduct TMS-dimer as a purple solid (33 mg, 6%). Data for the title compound: $^1$H NMR δ 8.97 (d, J=4.5 Hz, 4H), 8.85–8.83 (m, 8H), 8.80–8.78 (m, 8H), 8.68 (d, J=4.5 Hz, 4H), 8.56 (d, J=5.5 Hz, 2H), 8.35 (d, J=7.0 Hz, 2H), 8.27–8.26 (m, 2H), 8.20–8.17 (m, 2H), 8.08 (d, J=7.8 Hz, 2H), 7.93 (d, J=8.1 Hz, 4H), 7.88 (d, J=8.1 Hz, 2H), 7.80 (t, J=8.1 Hz, 2H), 7.68 (t, J=8.1 Hz, 2H), 7.30 (s, 12H), 2.64 (s, 12H), 2.60 (s, 6H), 1.85 (s, 24H), 1.80 (s, 12H), 0.25 (s, 18H), −2.65 (s, br, 2H); LD-MS obsd 2459.6; calcd avg mass 2459.9 ($C_{164}H_{134}N_{12}Si_2Zn_2$); $\lambda_{abs}$ 423, 514, 550, 589, 648 nm; $\lambda_{em}$ ($\lambda_{ex}$=550 nm) 653, 720 nm. Data for the TMS-dimer (byproduct): $^1$H NMR δ 8.96 (d, J=4.7 Hz, 2H), 8.84–8.82 (m, 4H), 8.80–8.78 (m, 4H), 8.76 (d, J=4.5 Hz, 2H), 8.69 (d, J=4.7 Hz, 4H), 8.56 (d, J=6.0 Hz, 1H), 8.36 (d, J=6.0 Hz, 1H), 8.28–8.25 (m, 1H), 8.20 (d, J=8.1 Hz, 2H), 8.18 (d, J=7.9 Hz, 2H), 8.08 (d, J=7.9 Hz, 1H), 7.94 (d, J=7.9 Hz, 2H), 7.89–7.86 (m, 4H), 7.80 (t, J=7.8 Hz, 1H), 7.67 (t, J=7.8 Hz, 1H), 7.30 (s, 4H), 7.26 (s, 4H), 3.30 (s, 1H), 2.64 (s, 6H), 2.61 (s, 6H), 1.86 (s, 12H), 1.82 (s, 12H), 0.26 (s, 9H), −2.65 (s, br, 2H); LD-MS obsd 1602.6; FAB-MS obsd 1600.63, calcd 1600.62 ($C_{109}H_{88}N_8SiZn$); $\lambda_{abs}$ 421, 515, 549, 592, 648 nm; $\lambda_{em}$ ($\lambda_{ex}$=550 nm) 652, 720 nm.

Example 49

ZnFbZn-m/m-CCH

A solution of ZnFbZn-m/m-CCTMS (370 mg, 0.15 mmol) in $CHCl_3$/THF (44 mL, 10:1) was treated with tetrabutylammonium fluoride (TBAF) on silica gel (1.20 g, 1.0–1.5 mmol F$^-$/g resin) and the mixture was stirred at room temperature. After 2 h, LD-MS and TLC analysis [silica, $CHCl_3$/hexanes (1:1)] showed the deprotection was complete. The reaction mixture was washed with water, dried ($Na_2SO_4$) and the solvent was removed. Chromatography (silica, $CHCl_3$/hexanes 1:1) afforded a purple solid, which was washed (by sonication) with methanol, filtered, and dried, affording a purple solid (312 mg, 90%): $^1$H NMR δ 8.96 (d, J=4.5 Hz, 4H), 8.86–8.83 (m, 8H), 8.80–8.78 (m, 8H), 8.68 (d, J=4.5 Hz, 4H), 8.56 (s, 2H), 8.38 (d, J=7.0 Hz, 2H), 8.28 (d, J=7.0 Hz, 2H), 8.23 (t, J=7.0 Hz, 2H), 8.19 (d, J=8.1 Hz, 4H), 8.08 (d, J=7.8 Hz, 2H), 7.93 (d, J=8.1 Hz, 4H), 7.90 (d, J=7.8 Hz, 2H), 7.81 (t, J=7.5 Hz, 2H), 7.71 (t, J=7.5 Hz, 2H), 7.30 (s, 8H), 7.25 (s, 4H), 3.15 (s, 2H), 2.65 (s, 12H), 2.60 (s, 6H), 1.85 (s, 24H), 1.80 (s, 12H), −2.65 (s, br, 2H); LD-MS obsd 2315.8; FAB-MS obsd 2314.85, calcd 2314.82 ($C_{158}H_{118}N_{12}Zn_2$); $\lambda_{abs}$ 421, 515, 549, 592, 648 nm; $\lambda_{em}$ ($\lambda_{ex}$=550 nm) 652, 720 nm.

Example 50

Zn$_3$-m/m-CCH

A solution of ZnFbZn-m/m-CCH (119 mg, 0.051 mmol) in $CHCl_3$ (10 mL) was treated with a solution of $Zn(OAc)_2 \cdot 2H_2O$ (56.0 mg, 0.26 mmol) in methanol (0.5 mL) overnight at room temperature. Standard workup and chromatography [silica, $CHCl_3$/hexanes (2:1)] afforded a purple solid (110 mg, 91%): $^1$H NMR δ 8.97 (d, J=5.1 Hz, 4H), 8.88–8.83 (m, 12H), 8.80 (d, J=5.4 Hz, 4H), 8.76 (d, J=5.4

Hz, 4H), 8.57 (m, 2H), 8.39–8.37 (m, 2H), 8.27 (d, J=8.7 Hz, 4H), 8.20 (d, J=8.1 Hz, 4H), 8.08 (d, J=8.1 Hz, 2H), 7.95–7.89 (m, 6H), 7.81 (t, J=8.1 Hz, 2H), 7.71 (t, J=8.1 Hz, 2H), 7.30 (s, 12H), 3.14 (s, 2H), 2.64 (s, 12H), 2.60 (s, 6H), 1.85 (s, 24H), 1.79 (s, 12H); LD-MS obsd 2376.8, calcd avg mass 2378.9 ($C_{158}H_{116}N_{12}Zn_3$); $\lambda_{abs}$ 422, 550, 590 nm, $\lambda_{em}$ ($\lambda_{ex}$=550 nm) 603, 650 nm.

Example 51

ZnFbZn-p/p-Br

Samples of Zn-24b (493 mg, 0.51 mmol) and 26 (174 mg, 0.23 mmol) were coupled using $Pd_2(dba)_3$ (63 mg, 0.069 mmol) and $P(o\text{-tol})_3$ (168 mg, 0.55 mmol) in toluene/triethylamine (96 mL, 5:1) at room temperature under argon. Analytical SEC and LD-MS analysis showed the reaction was complete after 3 h. Standard workup and chromatography (silica, $CHCl_3$) afforded a mixture of porphyrins. Further purification by chromatography (preparative SEC, THF) afforded four major bands (in order of elution): HMWM, desired trimer, mono-coupled by product (dimer) and monomeric species. The trimer-containing fraction was chromatographed [silica, $CHCl_3$/hexanes (3: 1)], affording a purple solid (195 mg, 35%): $^1$H NMR δ 8.93 (d, J=4.5 Hz, 4H), 8.91 (d, J=2.7 Hz, 2H), 8.89 (d, J=2.7 Hz, 2H), 8.86 (d, J=2.7 Hz, 2H), 8.85 (d, J=2.7 Hz, 2H), 8.81–8.78 (m, 2H), 8.60–8.58 (m, 2H), 8.34–8.28 (m, 2H), 8.26 (d, J=2.4 Hz, 2H), 8.23 (d, J=2.4 Hz, 2H), 8.13–8.09 (m, 6H), 7.97 (dd, $J^1$=1.5 Hz, $J^2$=8.1 Hz, 4H), 7.88 (dd, $J^1$=2.4 Hz, $J^2$=7.8 Hz, 4H), 7.83 (d, J=8.1 Hz, 2H), 7.34 (s, 4H), 7.29 (s, 4H), 7.28 (s, 4H), 2.68 (s, 6H), 2.64 (s, 6H), 2.63 (s, 6H), 1.91 (s, 12H), 1.83 (s, 12H), 1.82 (s, 12H), −2.54 (s, br, 2H); LD-MS obsd 2420.5, calcd avg mass 2425.2 ($C_{154}H_{116}Br_2N_{12}Zn_2$); $\lambda_{abs}$ 423, 515, 550, 591, 649 nm; $\lambda_{em}$ ($\lambda_{ex}$=550 mn) 601 (w), 649, 718 nm.

Example 52

Cyclo-$Zn_5$FbU via the 3+3 Route

Samples of $Zn_3$-m/m-CCH (35.7 mg, 0.015 mmol) and ZnFbZn-p/p-Br (40.0 mg, 0.015 mmol) were coupled using $Pd_2(dba)_3$ (4.6 mg, 0.0045 mmol), $P(o\text{-tol})_3$ (10.9 mg, 0.036 mmol), and the template 1,3,5-tris{4-[2-(4-pyridyl)ethynyl]phenyl}benzene (9.2 mg, 0.015 mmol) in toluene/triethylamine (9.0 mL, 5:1) at 80° C. under argon. Analytical SEC and LD-MS analysis showed the reaction was complete after 2 h. The reaction mixture was loaded directly on a short SEC column (THF) and all the porphyrin-containing fractions were collected. Chromatography (silica, $CHCl_3$) gave a porphyrin mixture, which was purified by preparative SEC (THF), removing most of the HMWM. Repetitive preparative SEC chromatography (three columns) gave a purple solid. Final chromatography [silica, $CHCl_3$/hexanes (4:1)] and washing with methanol gave a purple solid (9.5 mg, 13.6%): $^1$H NMR δ 8.97 (d, J=4.5 Hz, 8H), 8.88 (d, J=5.1 Hz, 4H), 8.84 (d, J=5.1 Hz, 20H), 8.76 (d, J=5.1 Hz, 4H), 8.73 (d, J=5.1 Hz, 12H), 8.53–8.50 (m, 4H), 8.32 (d, J=7.5 Hz, 6H), 8.18 (d, J=8.7 Hz, 12H), 8.08 (d, J=7.5 Hz, 6H), 7.91 (d, J=7.8 Hz, 12H), 7.82 (t, J=8.1 Hz, 8H), 7.31 (s, br, 12H), 7.22 (s, br, 12H), 2.65 (s, br, 12H), 2.58 (s, 24H), 1.88 (s, 12H), 1.86 (s, 12H), 1.76 (s, 48H), −2.61 (s, br, 2H); LD-MS obsd 4645.4, calcd avg mass 4642.3 ($C_{312}H_{230}N_{24}Zn_5$); $\lambda_{abs}$ (log ε) 428 (6.45), 512 (4.71), 550 (5.23), 591 (4.47), 649 nm; $\lambda_{em}$ ($\lambda_{ex}$=550 nm) 599, 651, 719 nm ($\Phi_f$=0.085). The LD-MS, $^1$H NMR, UV-Vis and fluorescence spectral data were identical with those obtained by a 5+1 route that employed successive iodo+ethyne coupling reactions.

The foregoing is illustrative of the present invention, and is not to be construed as limiting thereof. The invention is defined by the following claims, with equivalents of the claims to be included therein.

What is claimed is:

1. A light harvesting array, comprising:
   (a) a first substrate comprising a first electrode; and
   (b) a layer of light harvesting rods electrically coupled to said first electrode, said light harvesting rods in said layer consisting essentially of an oligomer of Formula I:

$$A^1(A^{b+1})_b \quad (I)$$

wherein:
   (i) b is at least 1;
   (ii) $A^1$ through $A^{b+1}$ are covalently coupled rod segments, which segments are different and which segments have sequentially less positive electrochemical potentials; and
   (iii) each segment $A^1$ through $A^{1+b}$ comprises a compound of Formula II:

$$X^1(X^{m+1})_m \quad (II)$$

and wherein:
   m is at least 1; and $X^1$ through $X^{m+1}$ are covalently coupled porphyrinic macrocycles.

2. The light harvesting array according to claim 1, wherein each porphyrinic macrocycle $X^1$ through $X^{m+1}$ is the same within each individual rod segment.

3. The light harvesting array according to claim 1, wherein $X^1$ through $X^{m+1}$ are selected from the group consisting of chlorins, bacteriochlorins, and isobacteriochlorins.

4. The light harvesting array according to claim 1, wherein b is from 1 to 5 and m is from 1 to 20.

5. The light harvesting array according to claim 1, wherein b is from 1 to 2 and m is from 1 to 5.

6. The light harvesting array according to claim 1, wherein at least one of $X^1$ through $X^{m+1}$ comprises a meso-linked porphyrinic macrocycle.

7. The light harvesting array according to claim 1, wherein at least one of $X^1$ through $X^{m+1}$ comprises a trans meso-linked porphyrinic macrocycle.

8. The light harvesting array according to claim 1, wherein $X^1$ through $X^{m+1}$ consist of meso-linked porphyrinic macrocycles.

9. The light harvesting array according to claim 1, wherein $X^1$ through $X^{m+1}$ consist of trans meso-linked porphyrinic macrocycles.

10. The light harvesting array according to claim 1, wherein at least one of $X^1$ through $X^{m+1}$ comprises a β-linked porphyrinic macrocycle.

11. The light harvesting array according to claim 1, wherein at least one of $X^1$ through $X^{m+1}$ comprises a trans β-linked porphyrinic macrocycle.

12. The light harvesting array according to claim 1, wherein $X^1$ through $X^{m+1}$ consist of β-linked porphyrinic macrocycles.

13. The light harvesting array according to claim 1, wherein $X^1$ through $X^{m+1}$ consist of trans β-linked porphyrinic macrocycles.

14. The light harvesting array according to claim 1, wherein said light harvesting rods are oriented substantially perpendicularly to said first electrode.

15. The light harvesting array according to claim 1, wherein said light harvesting rods are linear.

16. The light harvesting array according to claim 1, wherein said light harvesting rods are not greater than 500 nanometers in length.

17. The light harvesting array according to claim 1, wherein said light-harvesting rods are intrinsic rectifiers of excited-state energy.

18. The light harvesting array according to claim 1, wherein said light harvesting rods are intrinsic rectifiers of ground-state holes.

19. The light harvesting array according to claim 1, wherein said substrate is rigid.

20. The light harvesting array according to claim 1, wherein said substrate is flexible.

21. The light harvesting array according to claim 1, wherein said substrate is transparent.

22. The light harvesting array according to claim 1, wherein said substrate is opaque.

23. The light harvesting array according to claim 1, wherein said substrate is reflective.

24. The light harvesting array according to claim 1, wherein said substrate is substantially planar in shape.

25. The light harvesting array according to claim 1, wherein said electrode comprises a metallic conductor.

26. The light harvesting array according to claim 1, wherein said electrode comprises a nonmetallic conductor.

27. A solar cell, comprising:
the light harvesting array according to claim 1, and
a second substrate comprising a second electrode, with said first and second substrate being positioned to form a space therebetween, and with at least one of (i) said first substrate and said first electrode and (ii) said second substrate and said second electrode being transparent; and
an electrolyte in said space between said first and second substrates.

28. The solar cell according to claim 27, wherein said electrolyte comprises an aqueous electrolyte.

29. The solar cell according to claim 27, wherein said electrolyte comprises a nonaqueous electrolyte.

30. The solar cell according to claim 27, wherein said electrolyte comprises a polymer electrolyte.

31. The solar cell according to claim 27, wherein said electrolyte comprises a solid.

32. The solar cell according to claim 27, wherein said solar cell is devoid of liquid in said space between said first and second substrates.

33. The solar cell according to claim 27, wherein said light harvesting rods are electrically coupled to said second electrode.

34. The solar cell according to claim 27, further comprising a mobile charge carrier in said electrolyte.

35. An electrical device, comprising,
the solar cell according to claim 27, and
a circuit electrically coupled to said solar cell.

36. The electrical device according to claim 35, wherein said circuit comprises a resistive load.

37. A composition of light harvesting rods, said light harvesting rods in said composition consisting essentially of an oligomer of Formula I:

$$A^1(A^{b+1})_b \quad (I)$$

wherein:
(i) b is at least 1;
(ii) $A^1$ through $A^{b+1}$ are covalently coupled rod segments, which segments are different and which segments have sequentially less positive electrochemical potentials; and (iii) each segment $A^1$ through $A^{1+b}$ comprises a compound of Formula II:

$$X^1(X^{m+1})_m \quad (II)$$

and wherein:
m is at least 1; and
$X^1$ through $X^{m+1}$ are covalently coupled porphyrinic macrocycles.

38. The composition according to claim 37, wherein each porphyrinic macrocycle $X^1$ through $X^{m+1}$ is the same within each individual rod segment.

39. The composition according to claim 37, wherein $X^1$ through $X^{m+1}$ are selected from the group consisting of chlorins, bacteriochlorins, and isobacteriochlorins.

40. The composition according to claim 37, wherein b is from 1 to 5 and m is from 1 to 20.

41. The composition according to claim 37, wherein b is from 1 to 2 and m is from 1 to 5.

42. The composition according to claim 37, wherein at least one of $X^1$ through $X^{m+1}$ comprises a meso-linked porphyrinic macrocycle.

43. The composition according to claim 37, wherein at least one of $X^1$ through $X^{m+1}$ comprises a trans meso-linked porphyrinic macrocycle.

44. The composition according to claim 37, wherein $X^1$ through $X^{m+1}$ consist of meso-linked porphyrinic macrocycles.

45. The composition according to claim 37, wherein $X^1$ through $X^{m+1}$ consist of trans meso-linked porphyrinic macrocycles.

46. The composition to claim 37, wherein at least one of $X^1$ through $X^{m+1}$ comprises a β-linked porphyrinic macrocycle.

47. The composition according to claim 37, wherein at least one of $X^1$ through $X^{m+1}$ comprises a trans β-linked porphyrinic macrocycle.

48. The composition according to claim 37, wherein $X^1$ through $X^{m+1}$ consist of β-linked porphyrinic macrocycles.

49. The composition according to claim 37, wherein $X^1$ through $X^{m+1}$ consist of trans β-linked porphyrinic macrocycles.

50. The composition according to claim 37, wherein said light harvesting rods are linear.

51. The composition according to claim 37, wherein said light harvesting rods are not greater than 500 nanometers in length.

52. The composition according to claim 37, wherein said light-harvesting rods are intrinsic rectifiers of excited-state energy.

53. The composition according to claim 37, wherein said light harvesting rods are intrinsic rectifiers of ground-state holes.

54. A method of making a composition of light harvesting rods, said light harvesting rods comprising an oligomer of Formula I:

$$A^1(A^{b+1})_b \quad (I)$$

wherein:
(i) b is at least 1;
(ii) $A^1$ through $A^{b+1}$ are covalently coupled rod segments, which segments are different and which segments have sequentially less positive electrochemical potentials; and (iii) each segment $A^1$ through $A^{1+b}$ comprises a compound of Formula II:

$$X^1(X^{m+1})_m \qquad (II)$$

and wherein:

m is at least 1; and $X^1$ through $X^{m+1}$ are covalently coupled porphyrinic macrocycles; said method comprising the steps of:
(a) providing a first rod segment of Formula III and a second rod segment of Formula IV:

$$E[X^1(X^{m+1})_m]^1 f \qquad (III)$$

$$G[X^1(X^{m+1})_m]^2 T \qquad (IV)$$

wherein:
E is an end group;
one of f or G is an ethynyl group;
the other of f or G is a halo group; and
T is an end group; and then
(b) coupling said segment of Formula III to said segment of Formula IV to produce a compound of Formula I.

55. The method according to claim 54, wherein
f is an ethynyl group; and
G is a halo group.

56. The method according to claim 54, wherein
E is a bromo group;
f is an ethynylphenyl group;
G is an iodo group; and
T is a protected ethynyl group.

57. The method according to claim 54, wherein E is a halo group and said providing step further comprises providing a compound of Formula V:

$$Z[X^1(X^{m+1})_m]^3 J \qquad (V)$$

wherein:
Z is an end group; and
J is an ethynyl group; said method further comprising the step of:
(c) coupling said segment of Formula V to the product of said coupling step (b) to produce a compound of Formula I.

58. A rod segment useful for the production of light harvesting rods, said rod segment comprising a compound of Formula III:

$$E[X^1(X^{m+1})_m]^1 f \qquad (III)$$

wherein:
E is selected from the group consisting of bromo, chloro, and fluoro;
f is a protected or unprotected ethynyl group;
m is at least 1;
$X^1$ through $X^{m+1}$ are covalently coupled porphyrinic macrocycles; and
each porphyrinic macrocycle $X^1$ through $X^{m+1}$ is the same.

59. A rod segment according to claim 58, wherein:
E is a bromo group; and
f is a protected or unprotected ethynylphenyl group.

60. A rod segment according to claim 59, wherein f is a trimethylsilyl-protected ethynylphenyl group.

* * * * *